United States Patent
Tada et al.

(10) Patent No.: US 10,329,285 B2
(45) Date of Patent: Jun. 25, 2019

(54) SALTS OF QUINAZOLINE DERIVATIVE OR CRYSTALS THEREOF, AND THE PROCESS FOR PRODUCING THEREOF

(71) Applicant: Shionogi & Co., Ltd., Osaka (JP)

(72) Inventors: Yukio Tada, Osaka (JP); Yuusuke Tamura, Osaka (JP); Shuji Yonezawa, Osaka (JP); Kenichi Ishibashi, Hyogo (JP)

(73) Assignee: SHIONOGI & CO., LTD., Osaka (JP)

( * ) Notice: Subject to any disclaimer, the term of this patent is extended or adjusted under 35 U.S.C. 154(b) by 0 days.

(21) Appl. No.: 15/748,283

(22) PCT Filed: Jul. 28, 2016

(86) PCT No.: PCT/JP2016/072129
§ 371 (c)(1),
(2) Date: Jan. 29, 2018

(87) PCT Pub. No.: WO2017/018476
PCT Pub. Date: Feb. 2, 2017

(65) Prior Publication Data
US 2018/0215744 A1    Aug. 2, 2018

(30) Foreign Application Priority Data

Jul. 29, 2015 (JP) ................................ 2015-149259
Nov. 9, 2015 (JP) ................................ 2015-219635

(51) Int. Cl.
| C07D 413/12 | (2006.01) |
| A61K 31/5377 | (2006.01) |
| C07D 265/30 | (2006.01) |

(52) U.S. Cl.
CPC ........ C07D 413/12 (2013.01); A61K 31/5377 (2013.01); C07D 265/30 (2013.01); C07B 2200/13 (2013.01)

(58) Field of Classification Search
CPC .................................................. C07D 413/12
USPC ........................................................ 544/111
See application file for complete search history.

(56) References Cited

U.S. PATENT DOCUMENTS

2009/0143414 A1    6/2009 Kume
2011/0257391 A1    10/2011 Hagihara et al.

FOREIGN PATENT DOCUMENTS

| EP | 1 854 789 | 11/2007 |
| EP | 2 374 801 | 10/2011 |
| WO | 02/02552 | 1/2002 |
| WO | 2006/090717 | 8/2006 |
| WO | 2009/079541 | 6/2009 |
| WO | 2009/079547 | 6/2009 |
| WO | 2010/074150 | 7/2010 |

OTHER PUBLICATIONS

International Preliminary Report on Patentability dated Feb. 8, 2018 in International Application No. PCT/JP2016/072129.
Extended European Search Report dated Nov. 27, 2018 in corresponding European Patent Application No. 16 830 581.1.
International Search Report dated Oct. 11, 2016 in International Application No. PCT/JP2016/072129.
Toshiyuki Yoneda et al., "The Antiproliferative Effects of Tyrosine Kinase Inhibitors Tyrphostins on a Human Squamous Cell Carcinoma in Vitro and in Nude Mice", Cancer Research, Aug. 1991, vol. 51, p. 4430-4435.
Kaladhar B. Reddy, et al., "Inhibition of Breast Cancer Cell Growth in Vitro by a Tyrosine Kinase Inhibitor1", Cancer Research, Jul. 1, 1992, vol. 52, p. 3636-3641.
Valerie G. Brunton et al., "Cell-signaling targets for antitumour drug development", Cancer Chemotherapy and Pharmacology, 1993, vol. 32, p. 1-19.
Yasuo Kokai et al., "Synergistic Interaction of p185c-neu and the EGF Receptor Leads to Transformation of Rodent Fibroblasts", Cell, vol. 58, Jul. 28, 1989, p. 287-292.
Edited by C.G. Wermuth, "The practice of medicinal chemistry", p. 347-365, Technomics, 1999.
Handbook of preparation of crystal of organic compound: principle and know-how, Jul. 25, 2008, p. 57-84.
Recent Progress in Physicochemical Characterization and Formulation Technologies for Poorly Soluble Drugs, 2010.
Simon N. Black, et al., "Structure, Solubility, Screening, and Synthesis of Molecular Salts", Journal of Pharmaceutical Sciences, vol. 96, No. 5, May 2007.

*Primary Examiner* — Kahsay Habte
(74) *Attorney, Agent, or Firm* — Wenderoth, Lind & Ponack, L.L.P.

(57) ABSTRACT

Crystals of a quinazoline derivative are provided. The present invention relates to an acid addition salt of a compound represented by Formula (I):

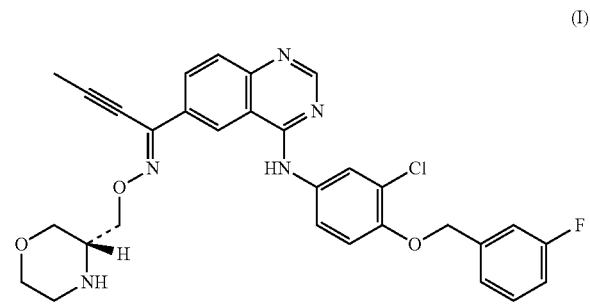

(I)

a pharmaceutical composition containing it, and the like.

16 Claims, 53 Drawing Sheets

[Figure 1]
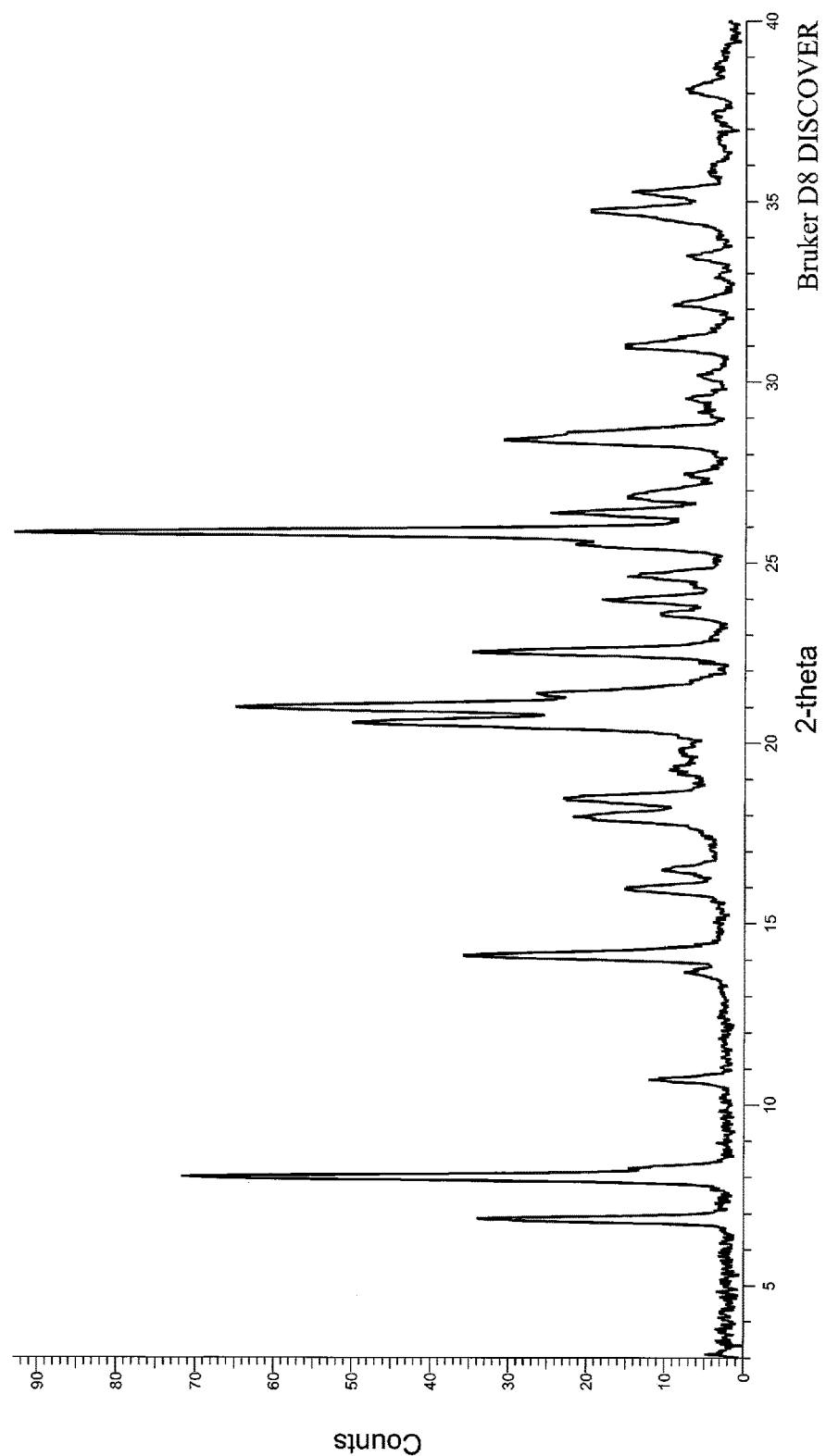

[Figure 2]
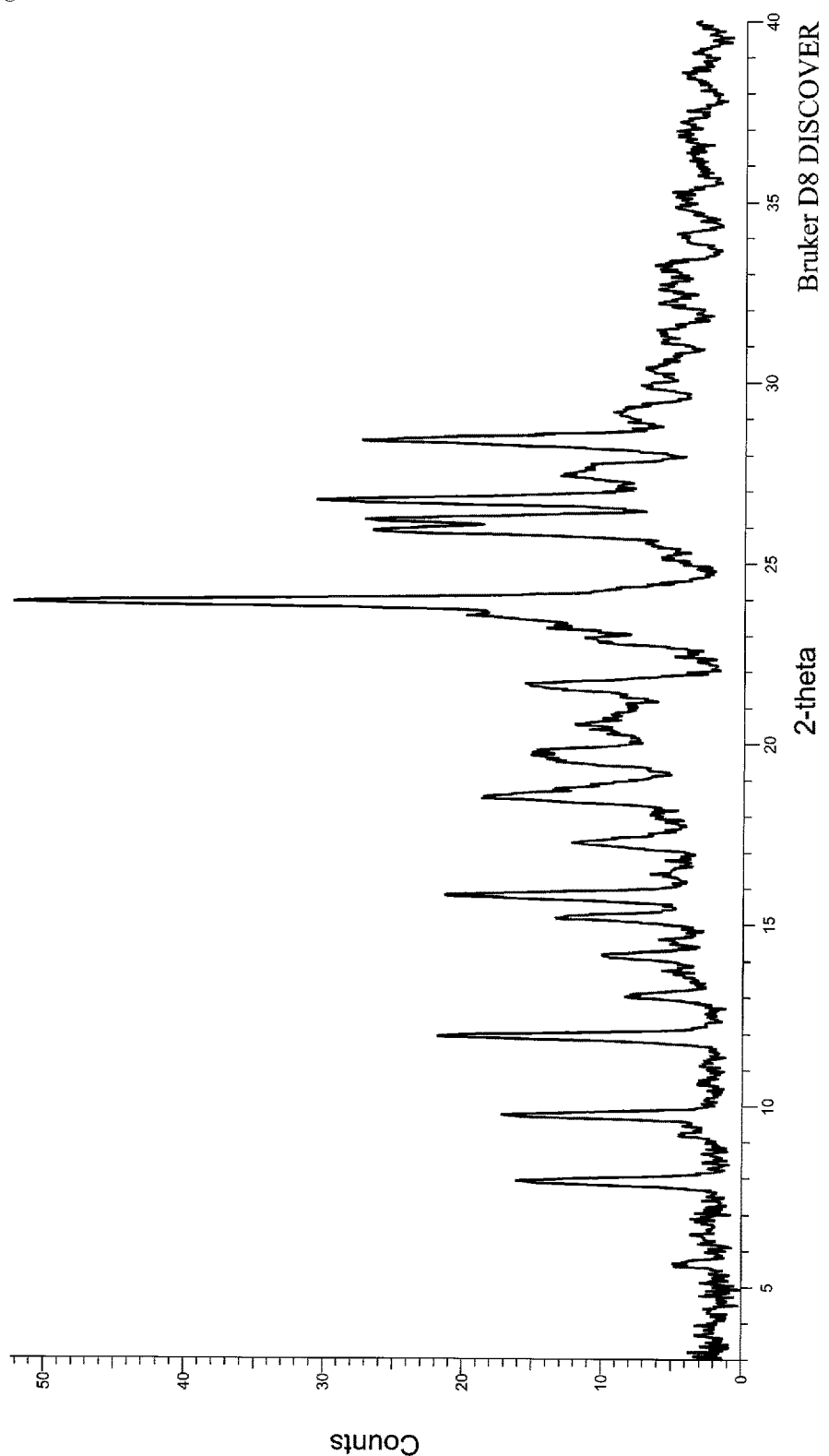

[Figure 3]
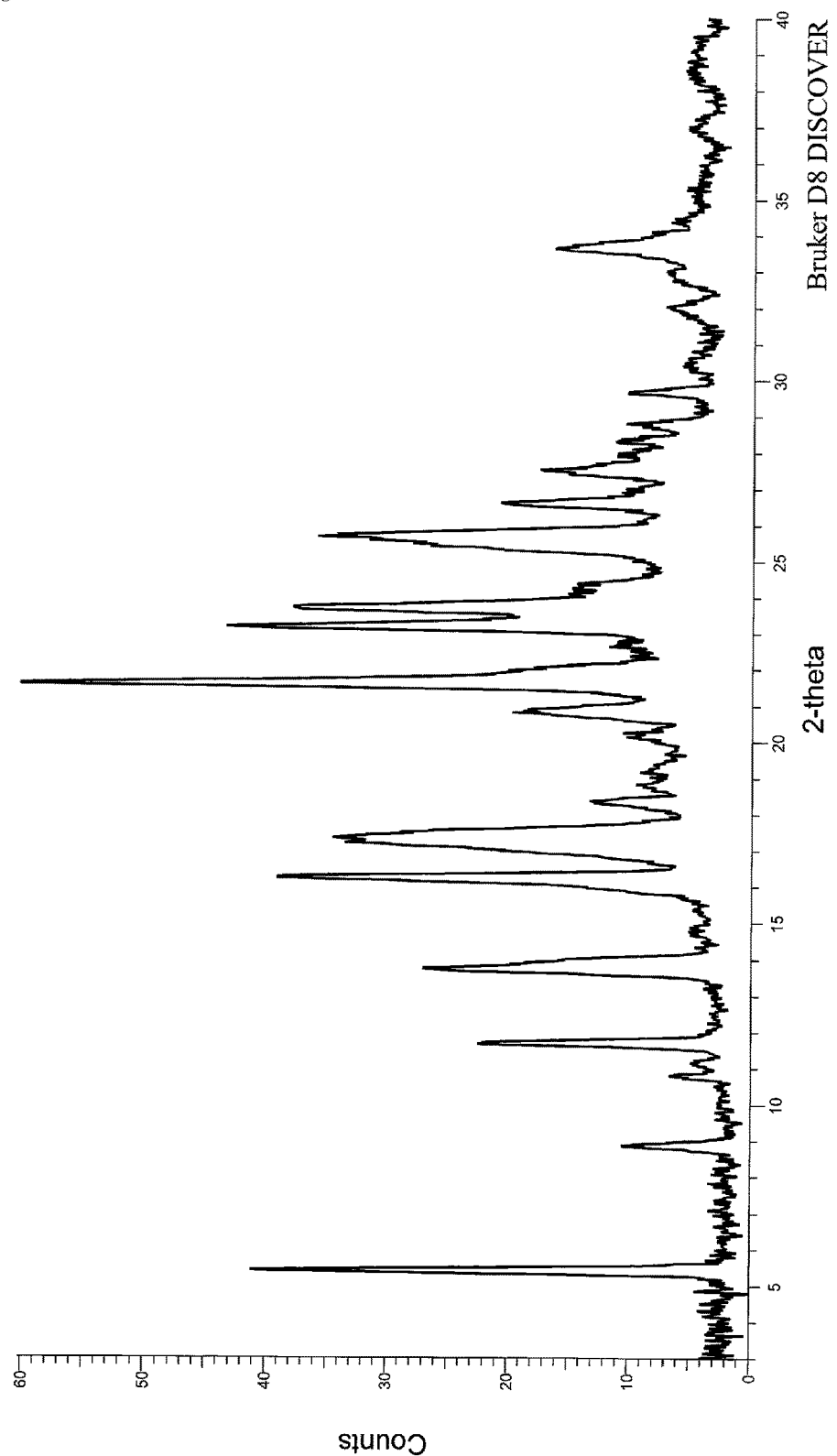

[Figure 4]
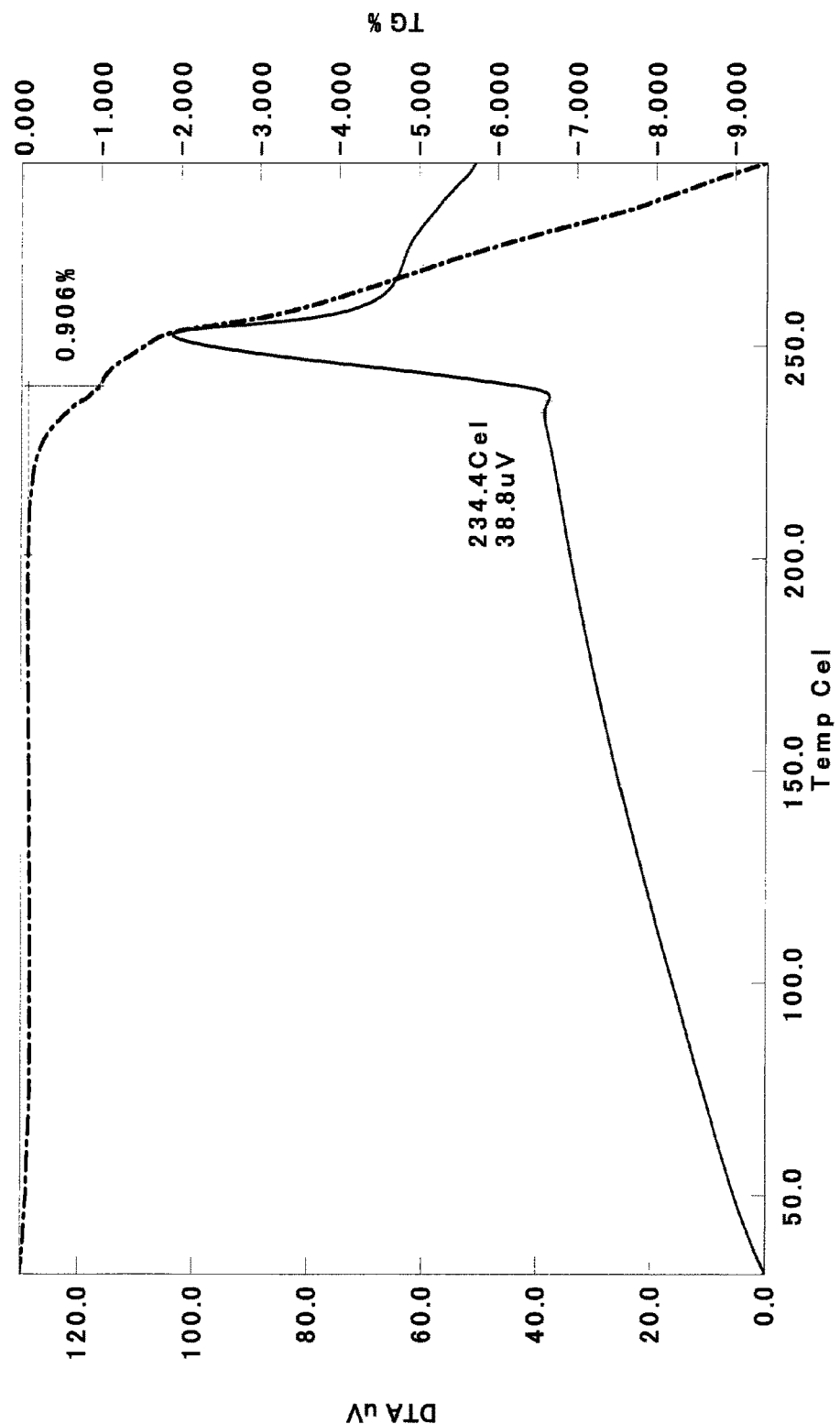

[Figure 5]
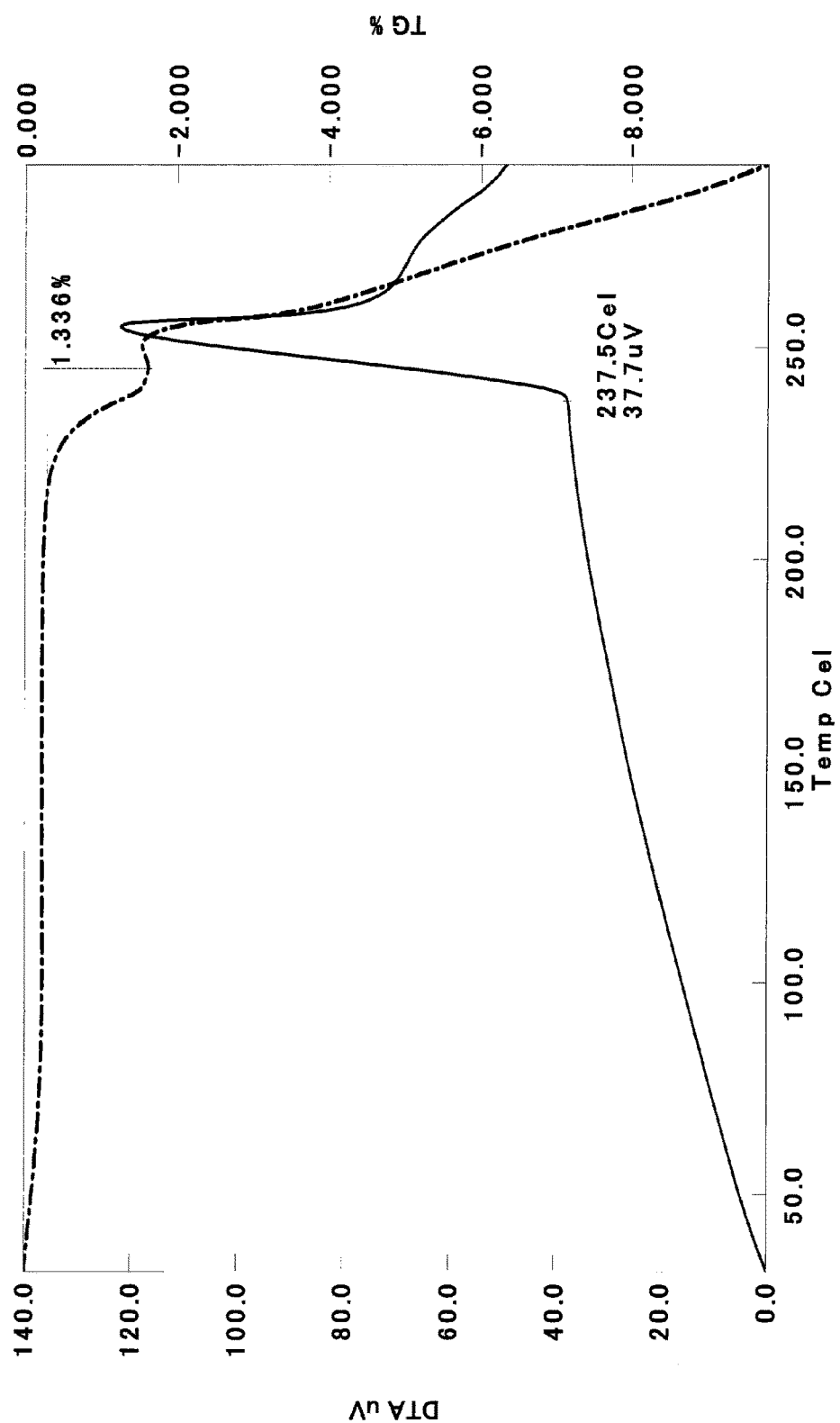

[Figure 6]
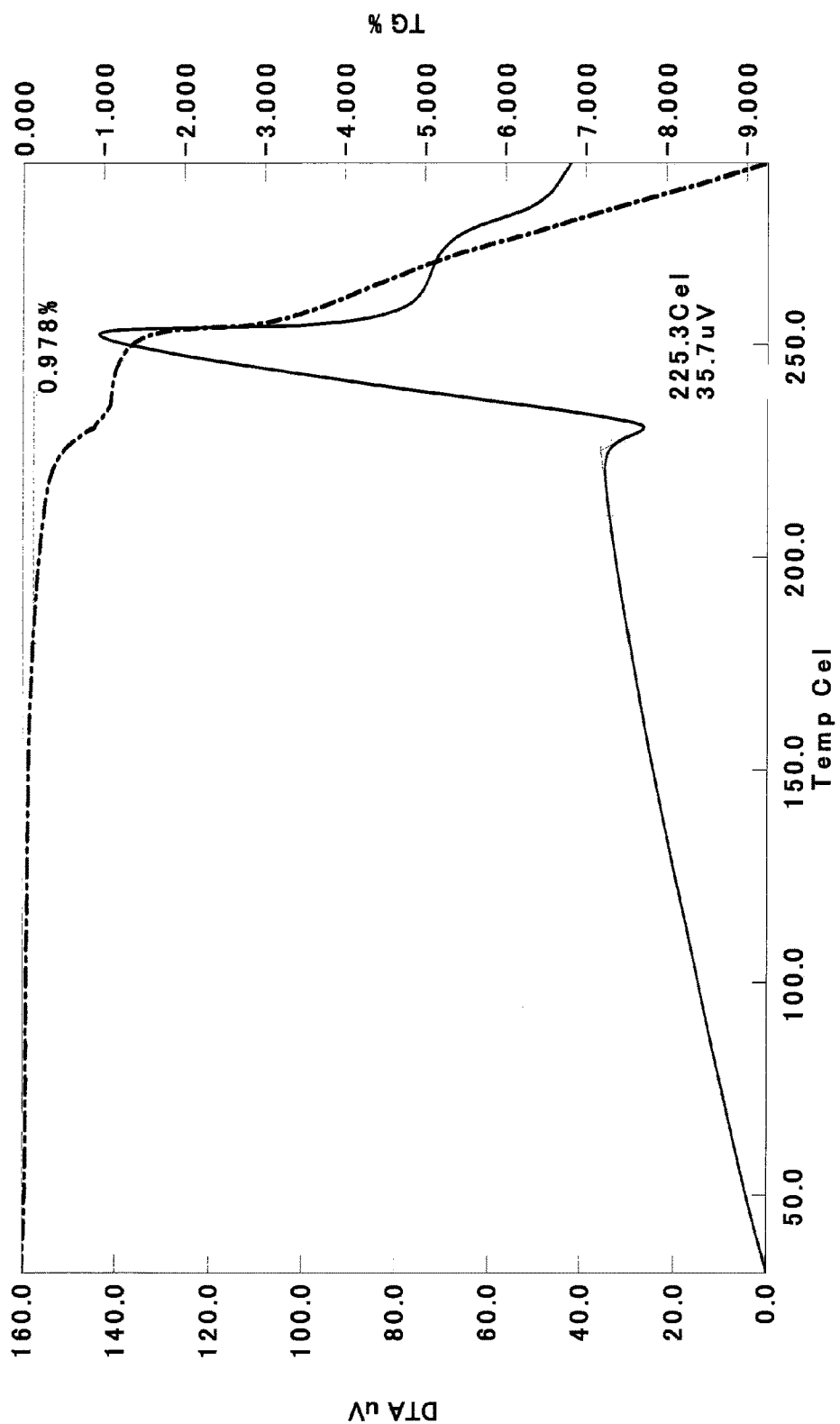

[Figure 7]
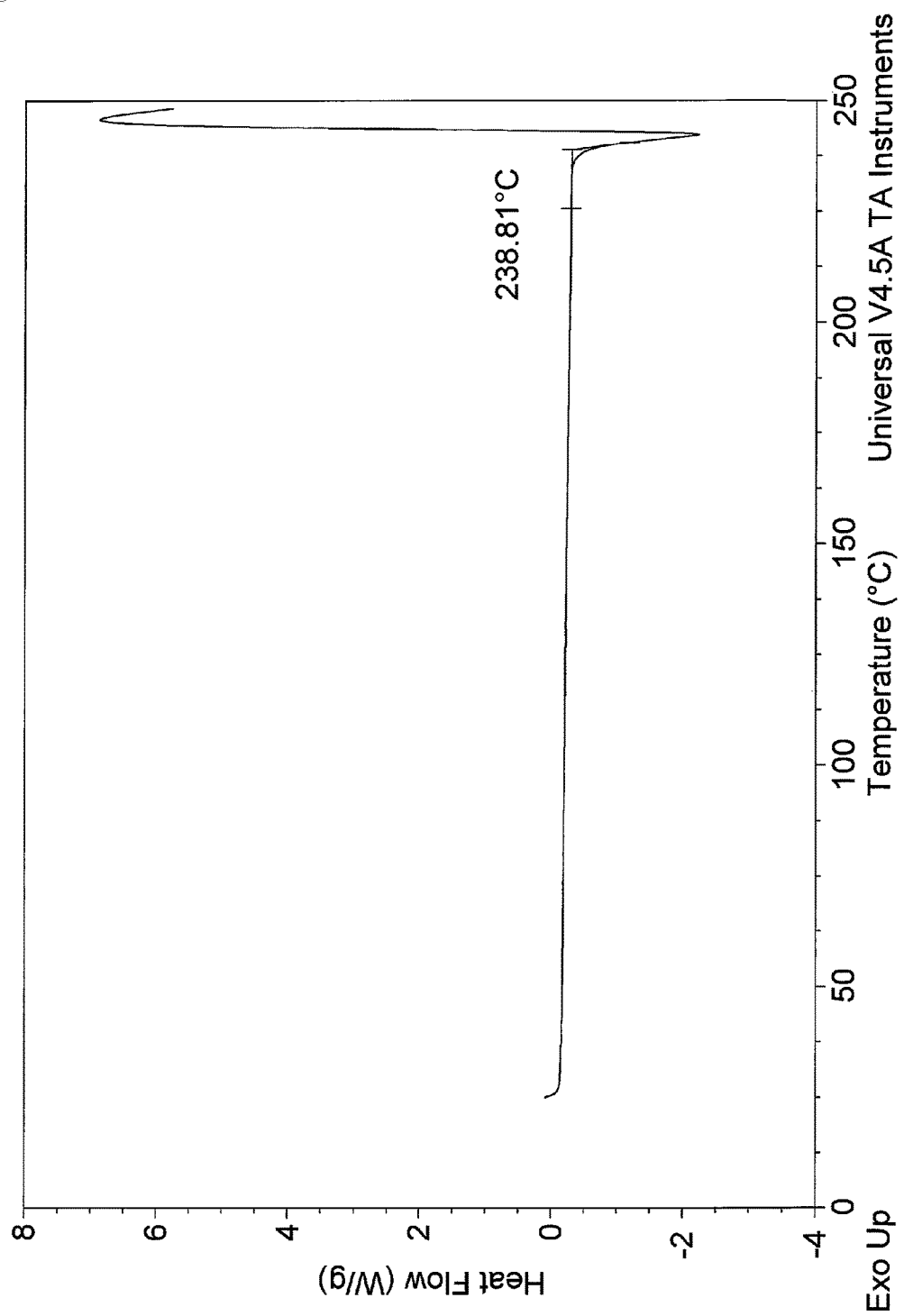

[Figure 8]
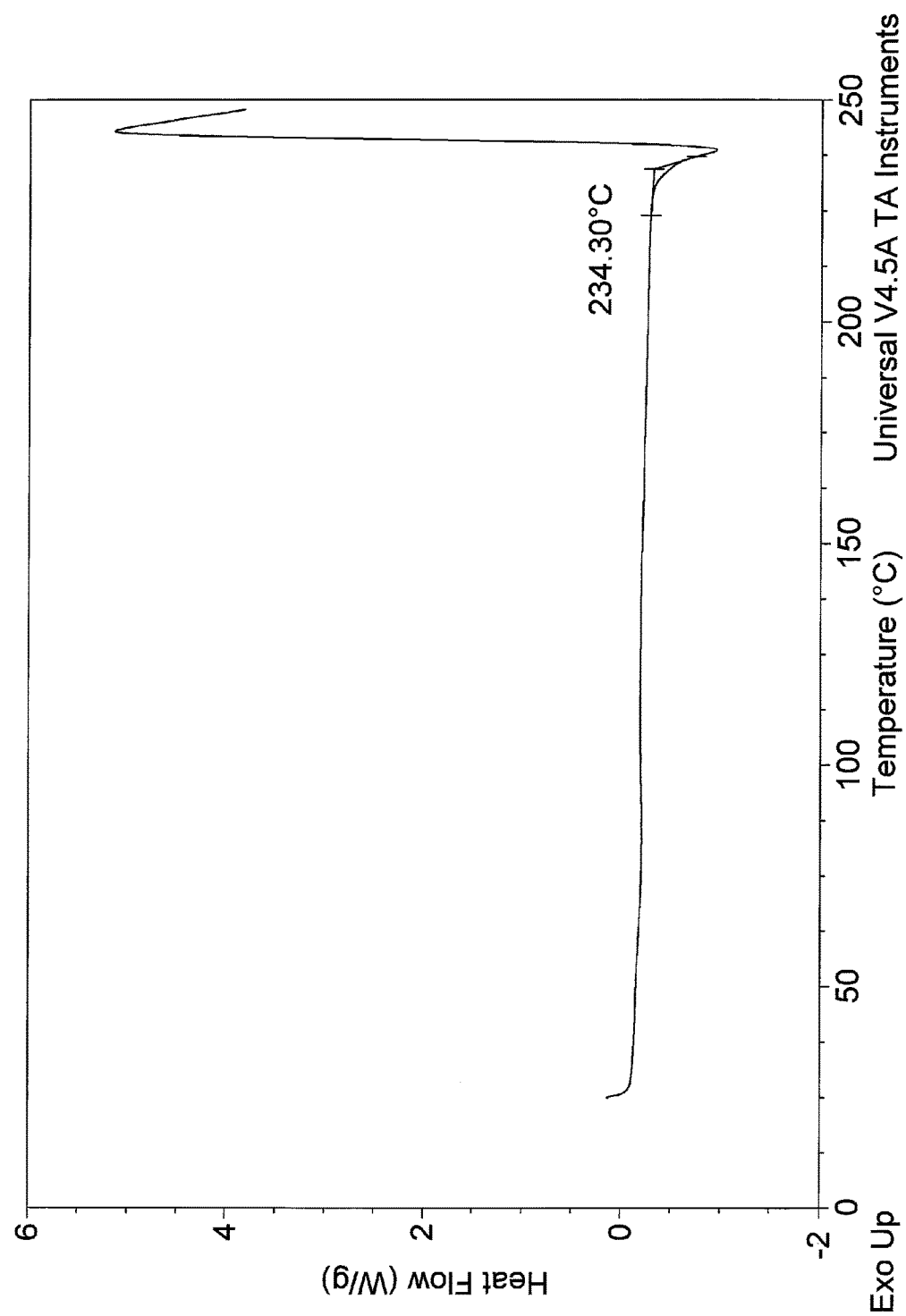

[Figure 9]
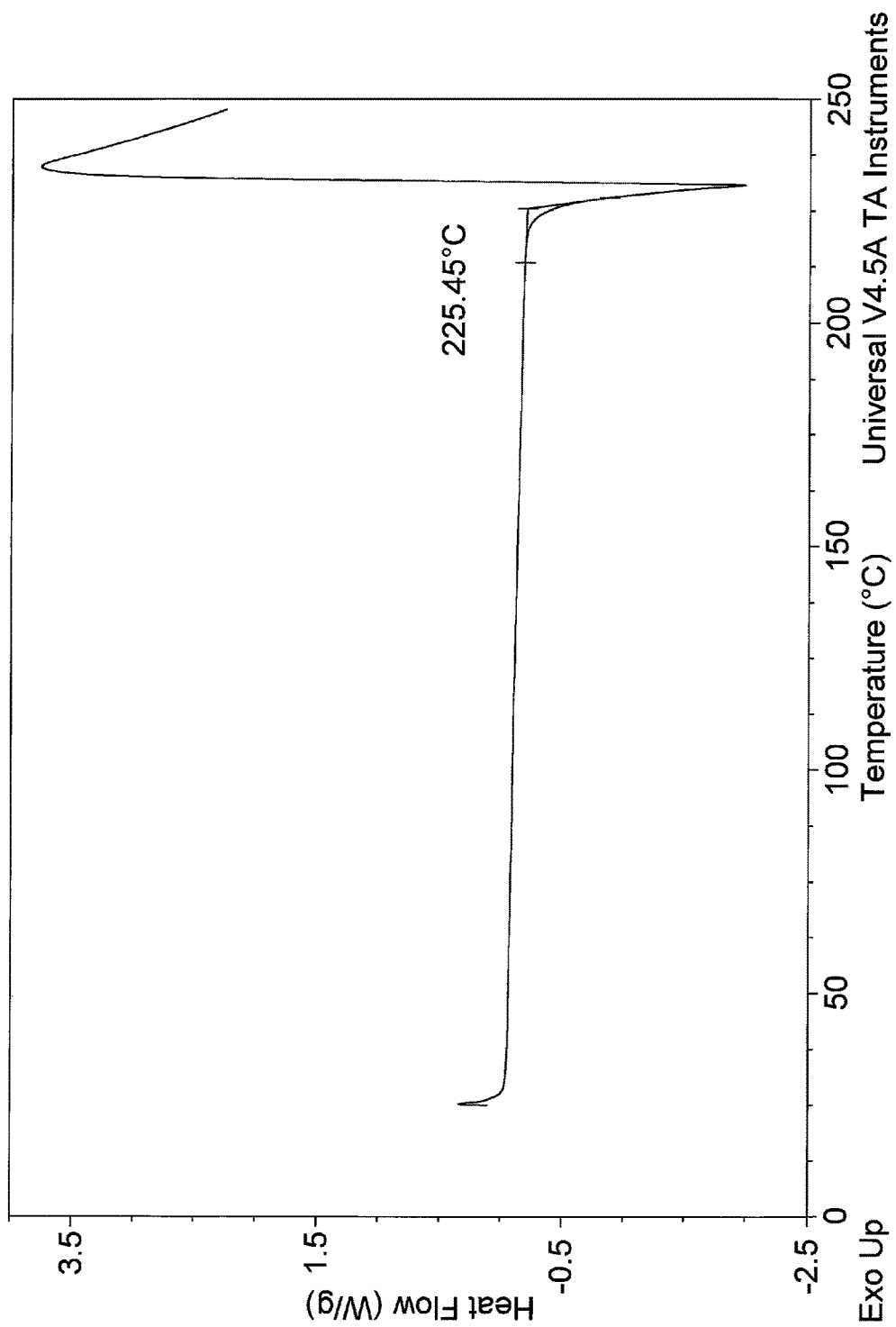

[Figure 10]
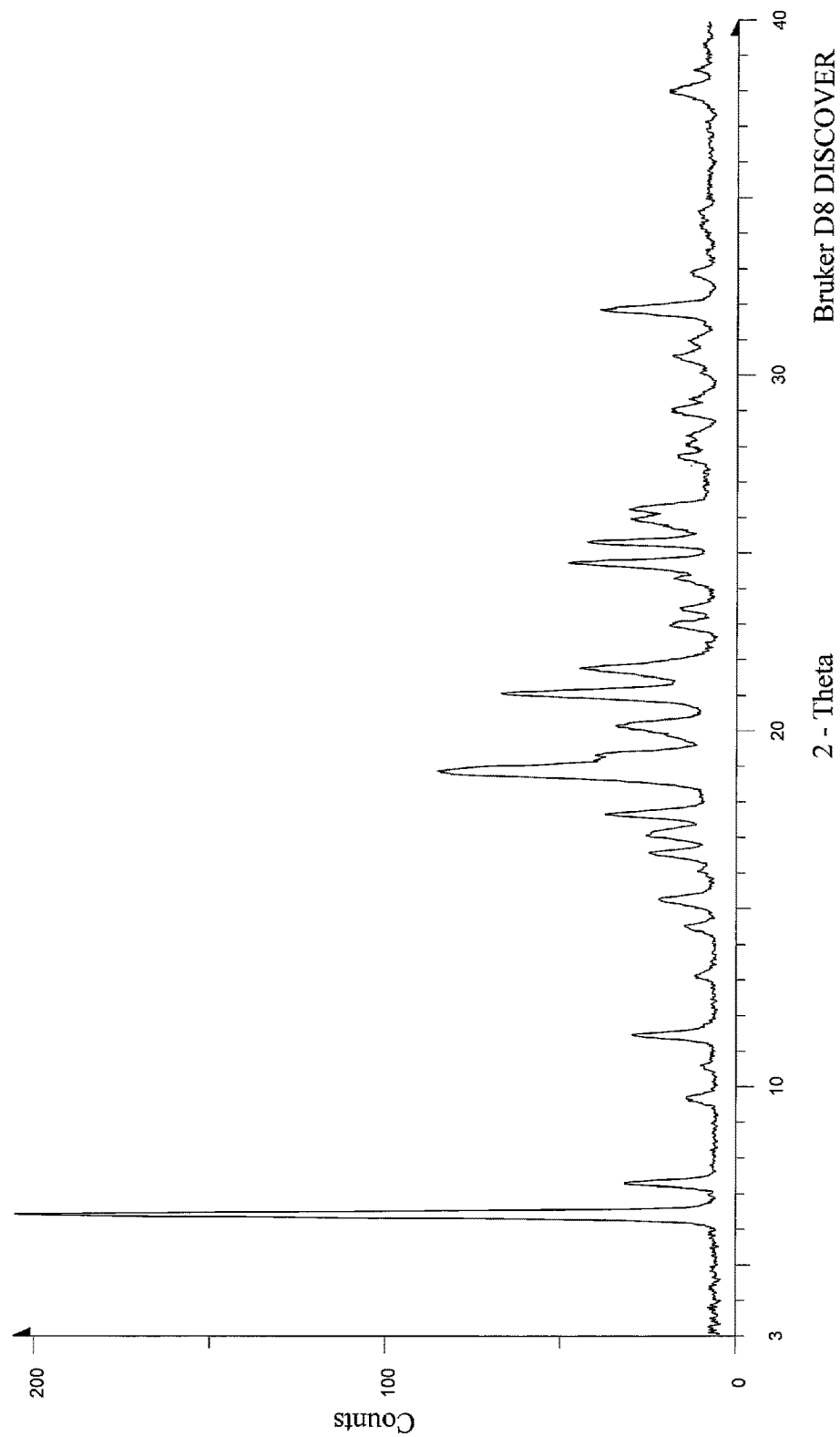

[Figure 11]
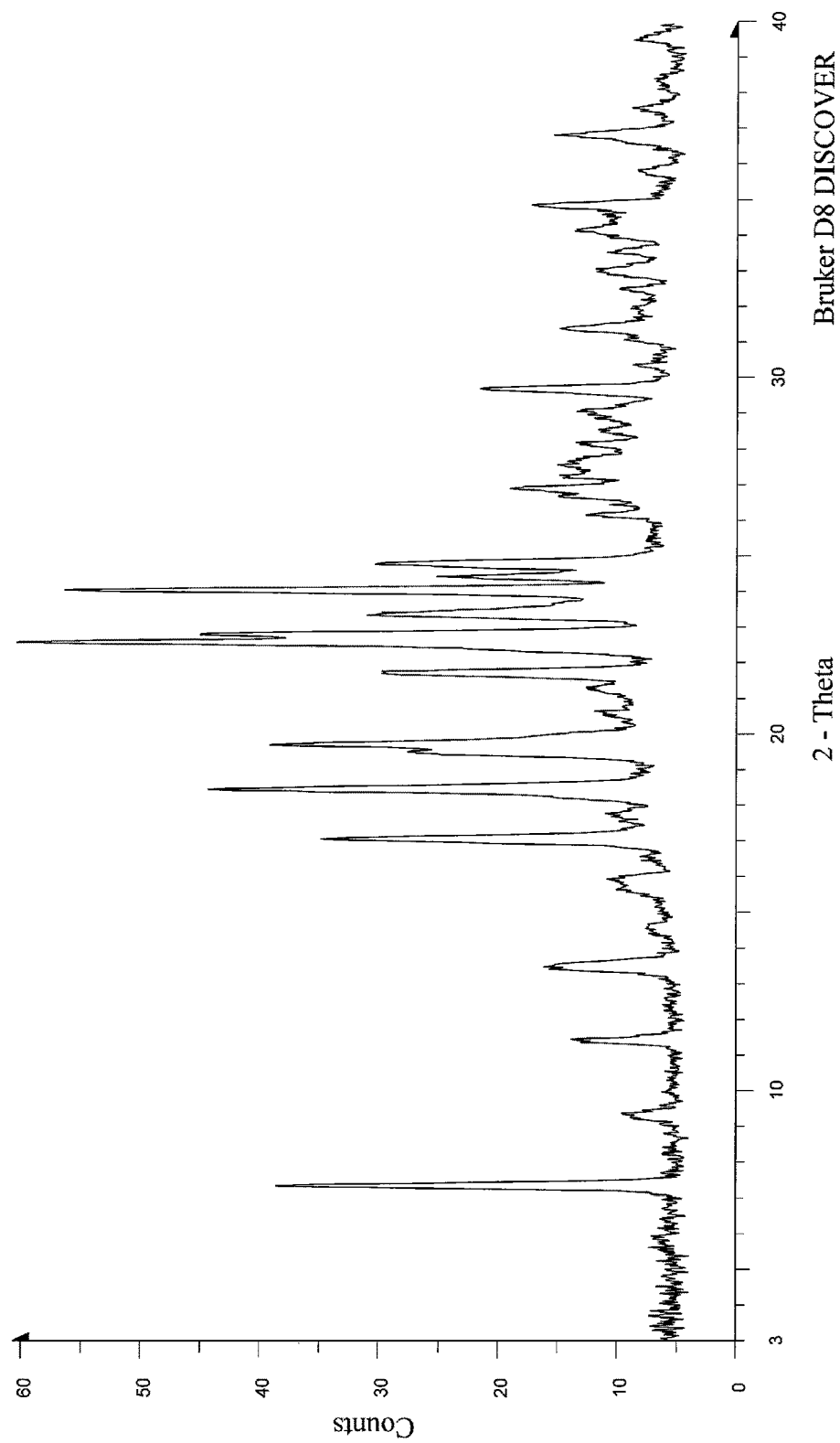

[Figure 12]
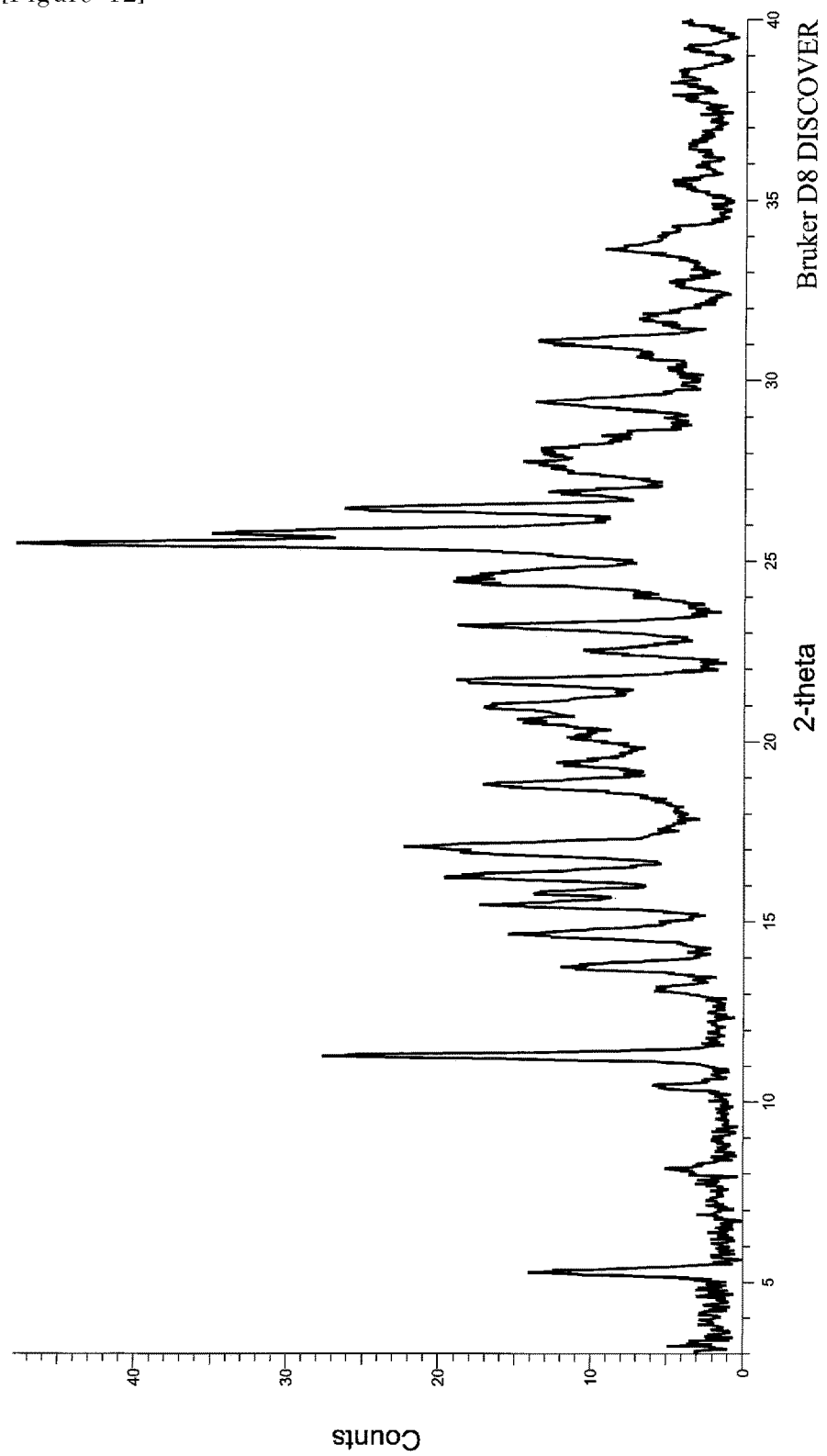

[Figure 13]
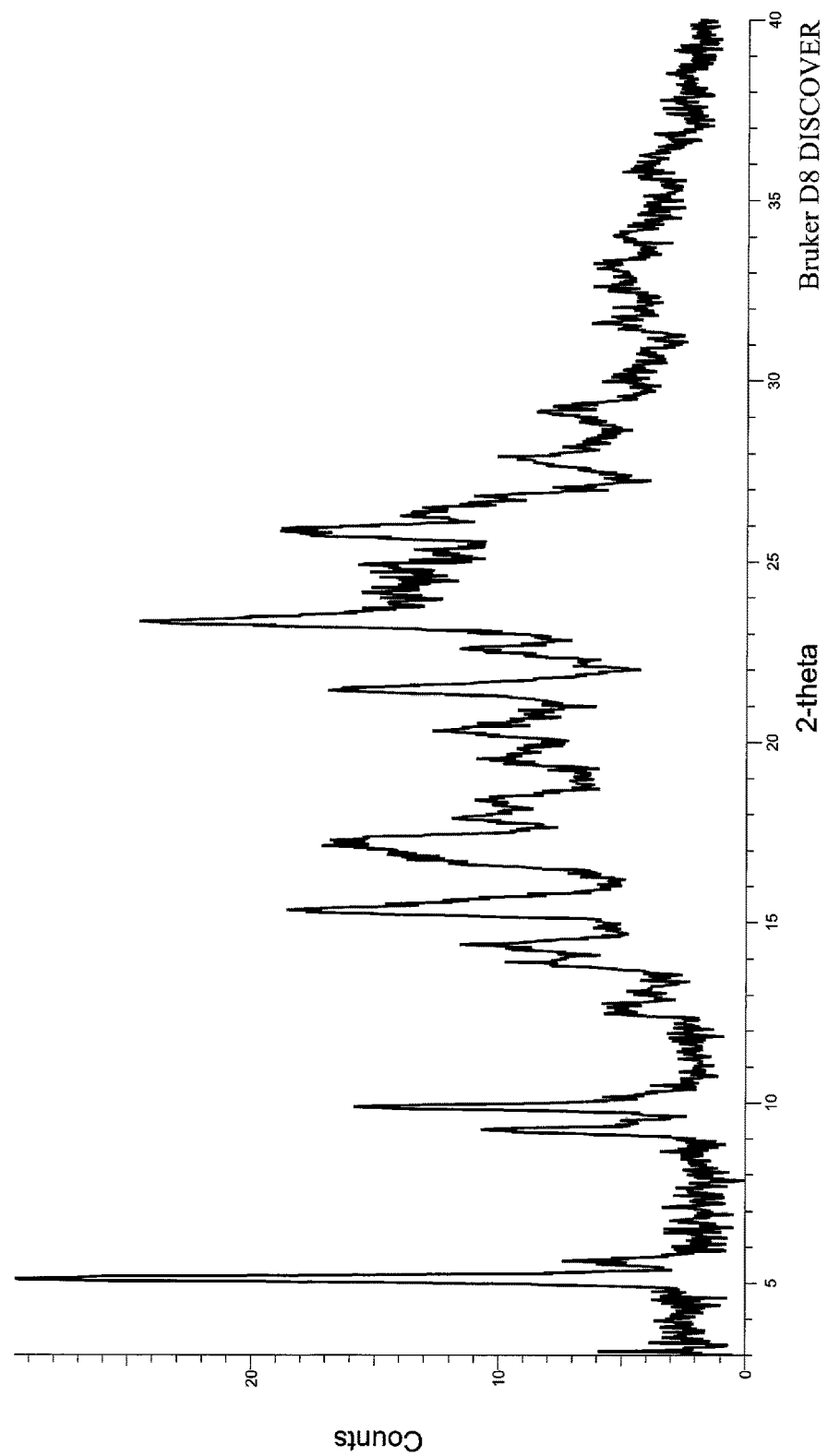

[Figure 14]
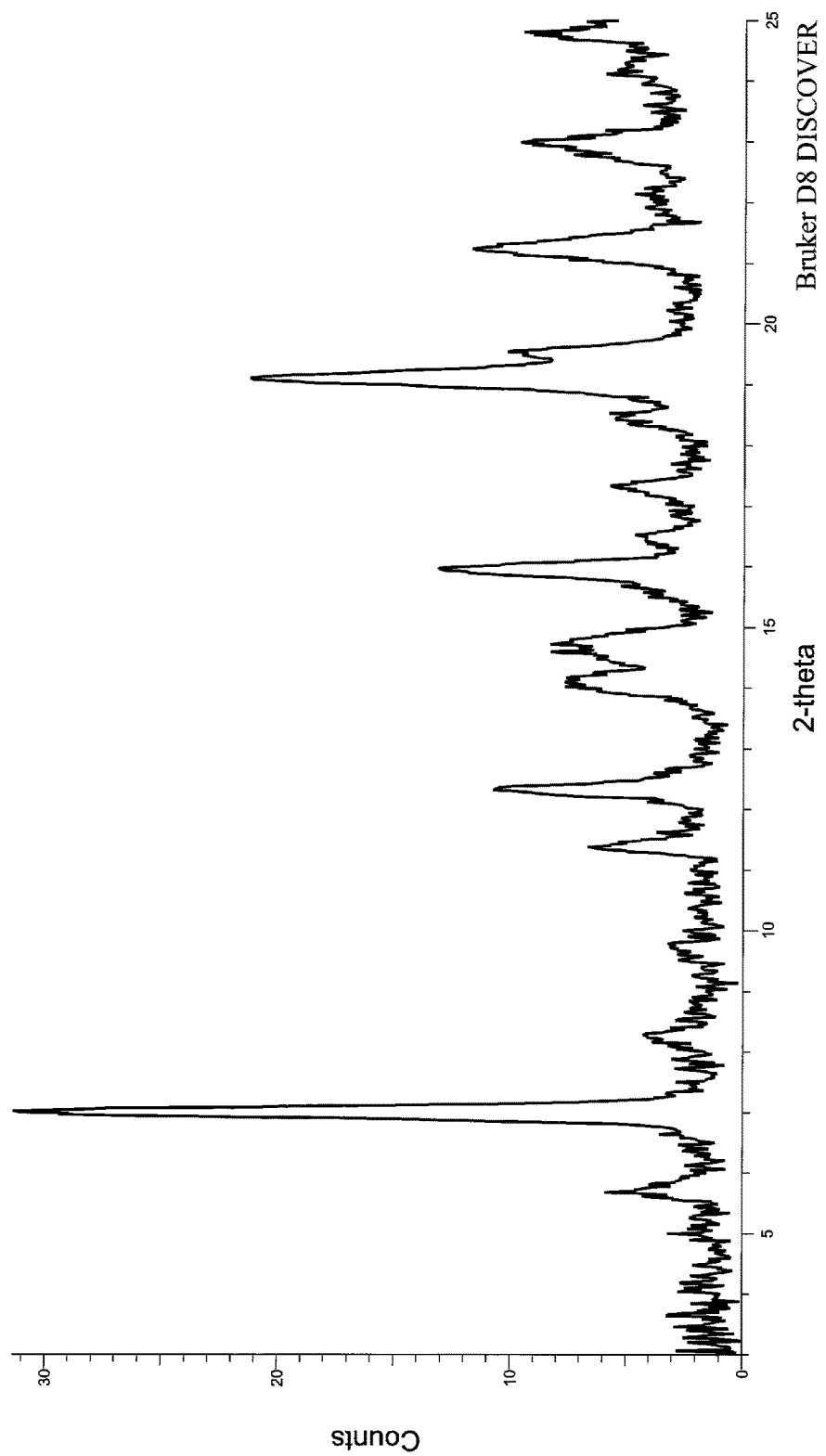

[Figure 15]
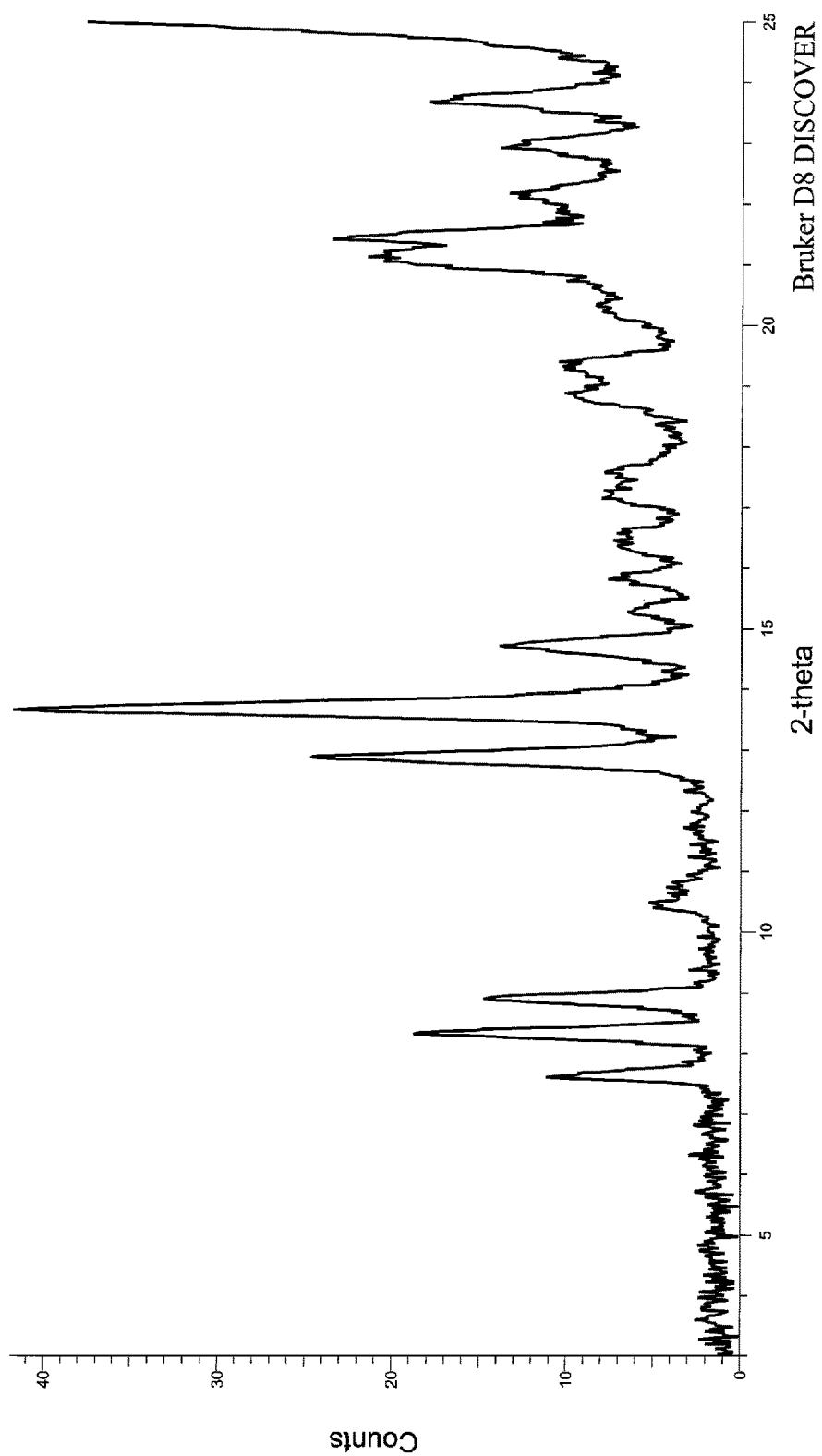

[Figure 16]
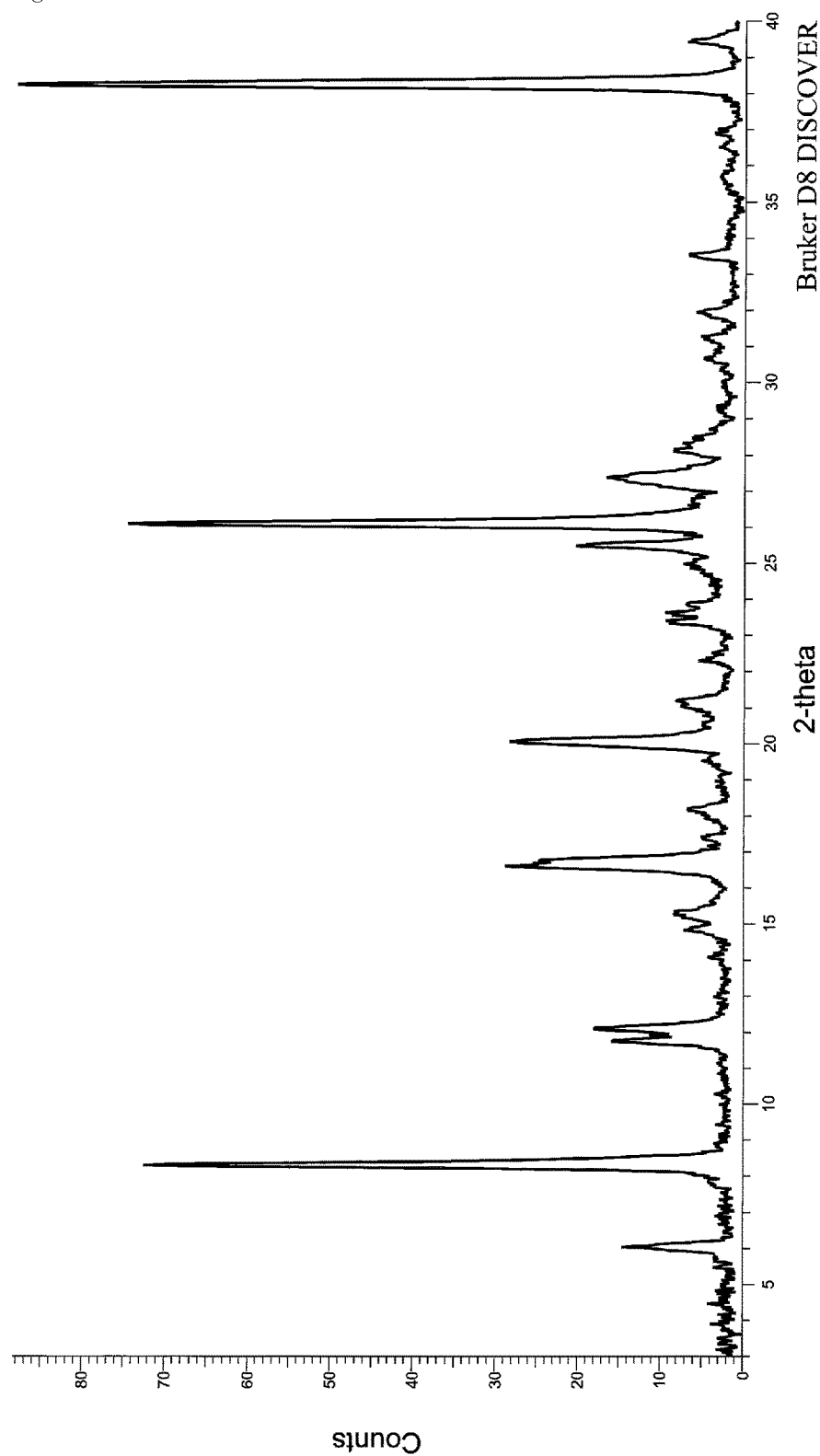

[Figure 17]
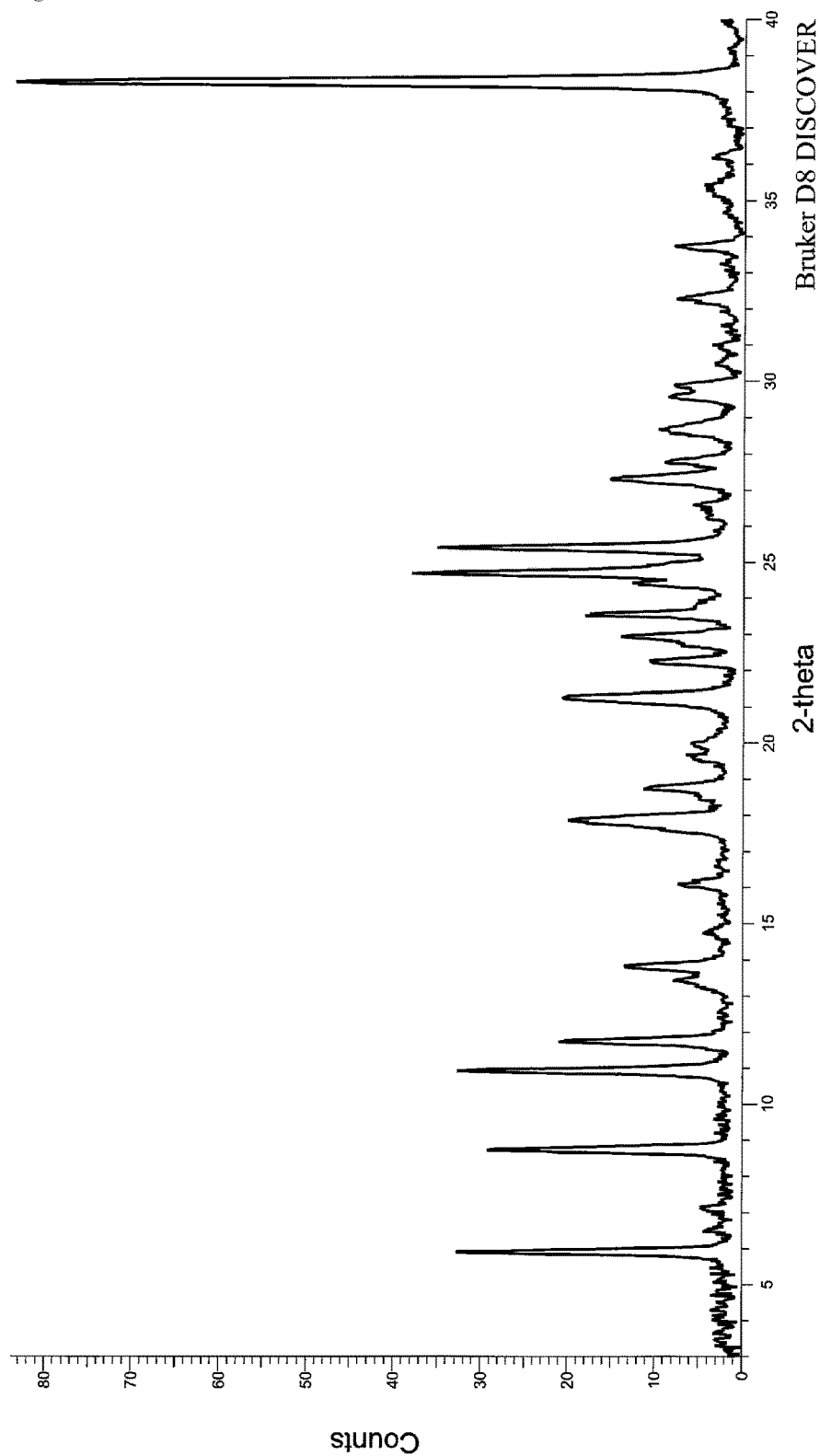

[Figure 18]
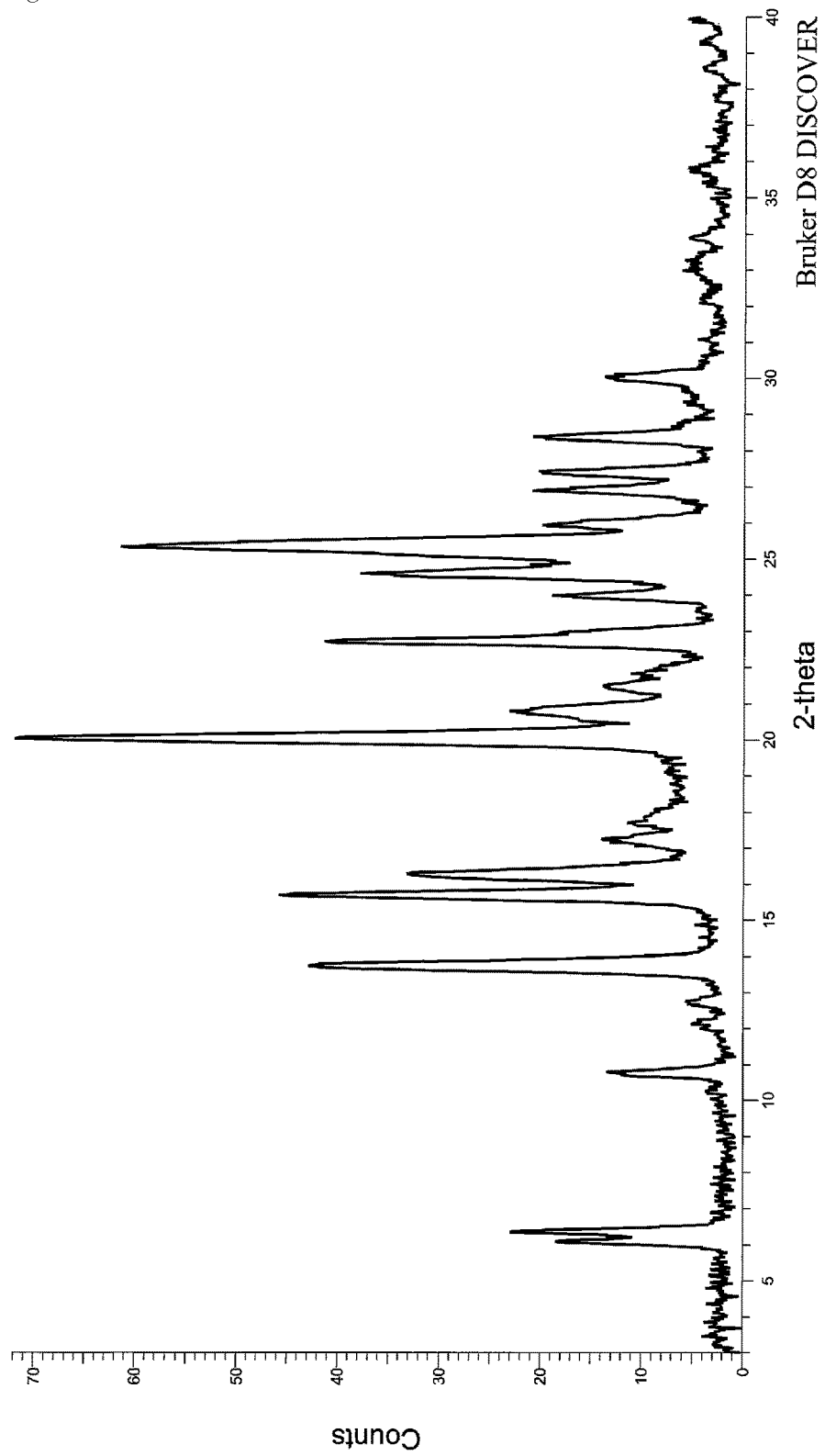

[Figure 19]
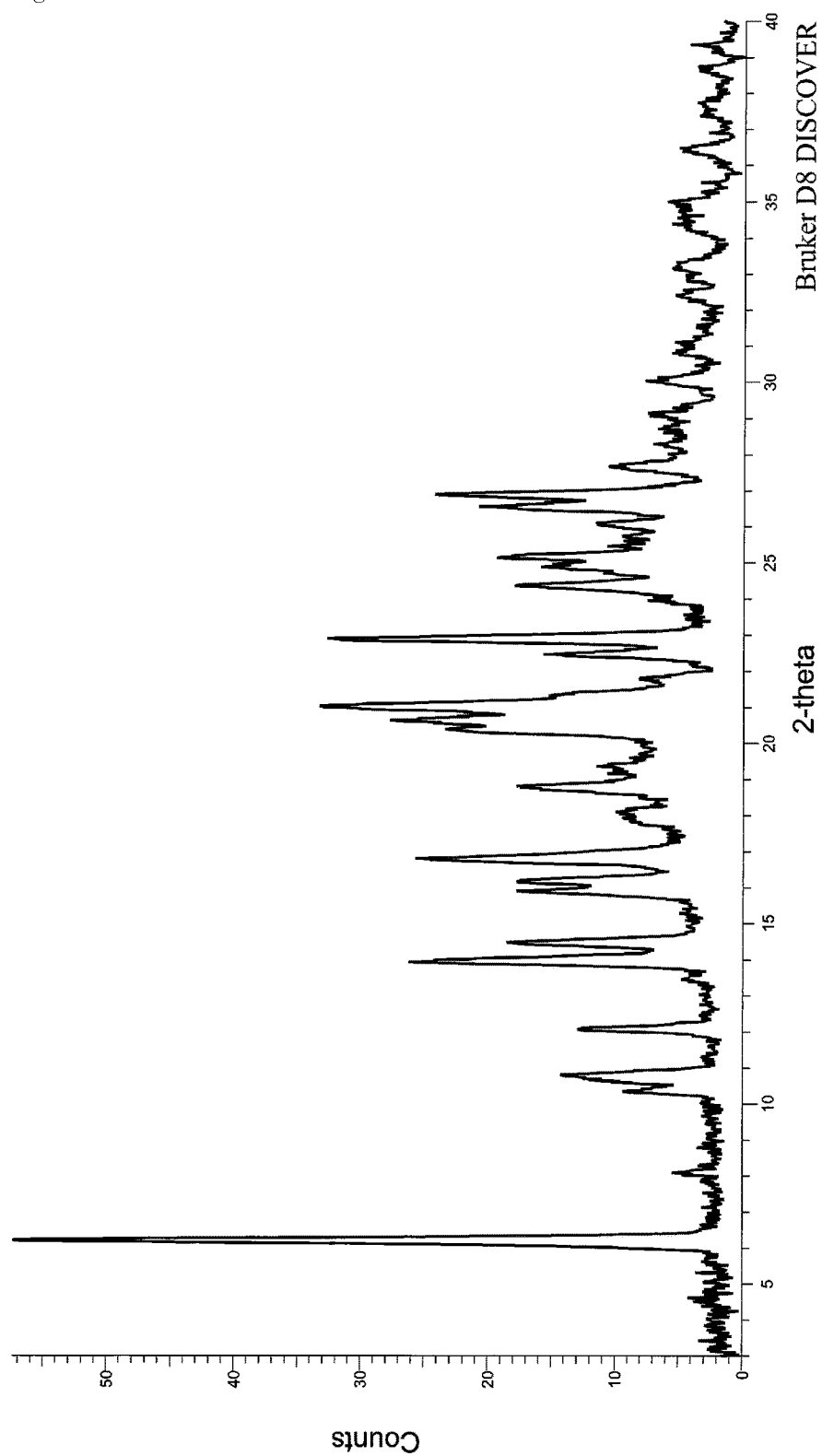

[Figure 20]
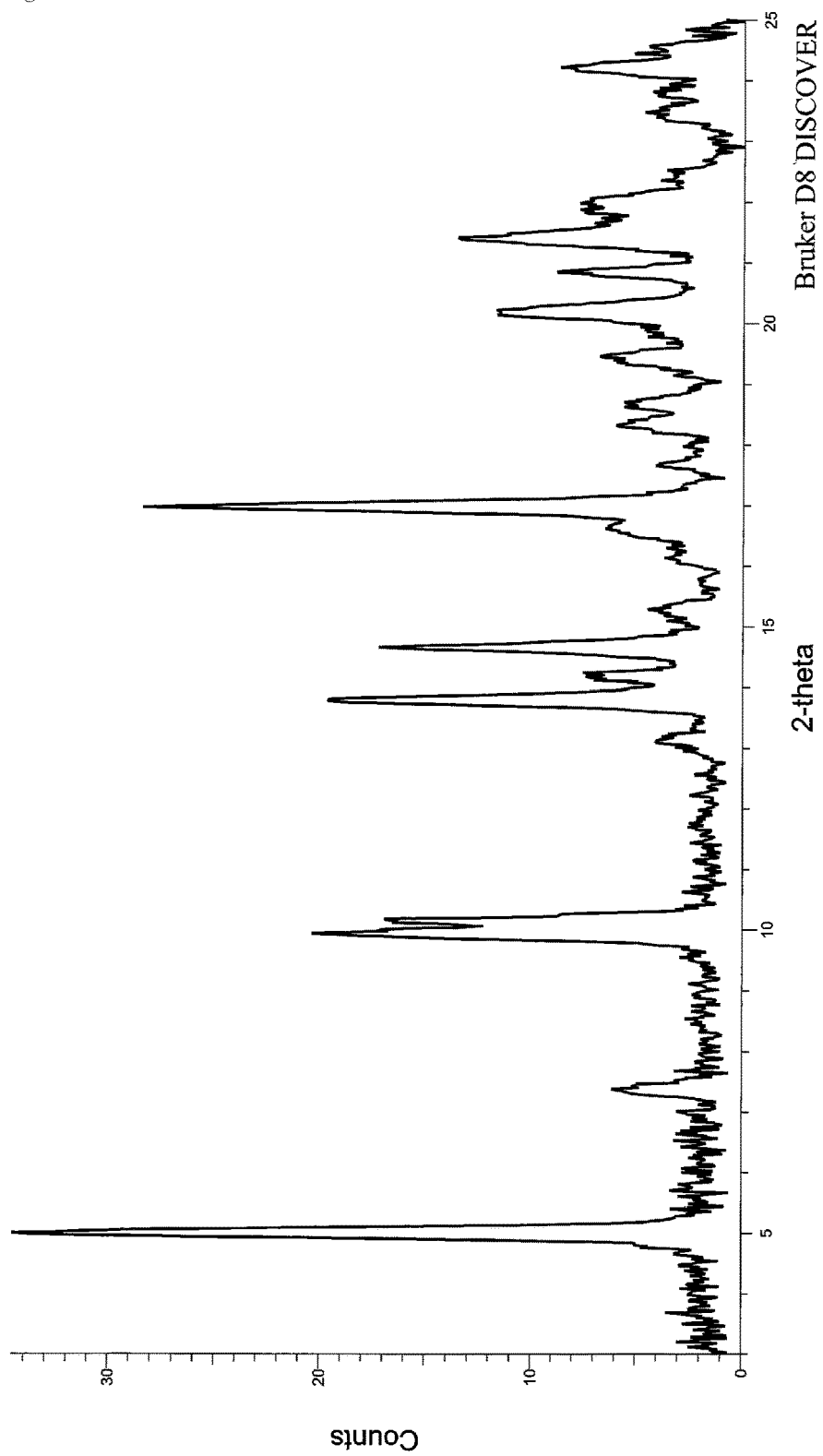

[Figure 21]
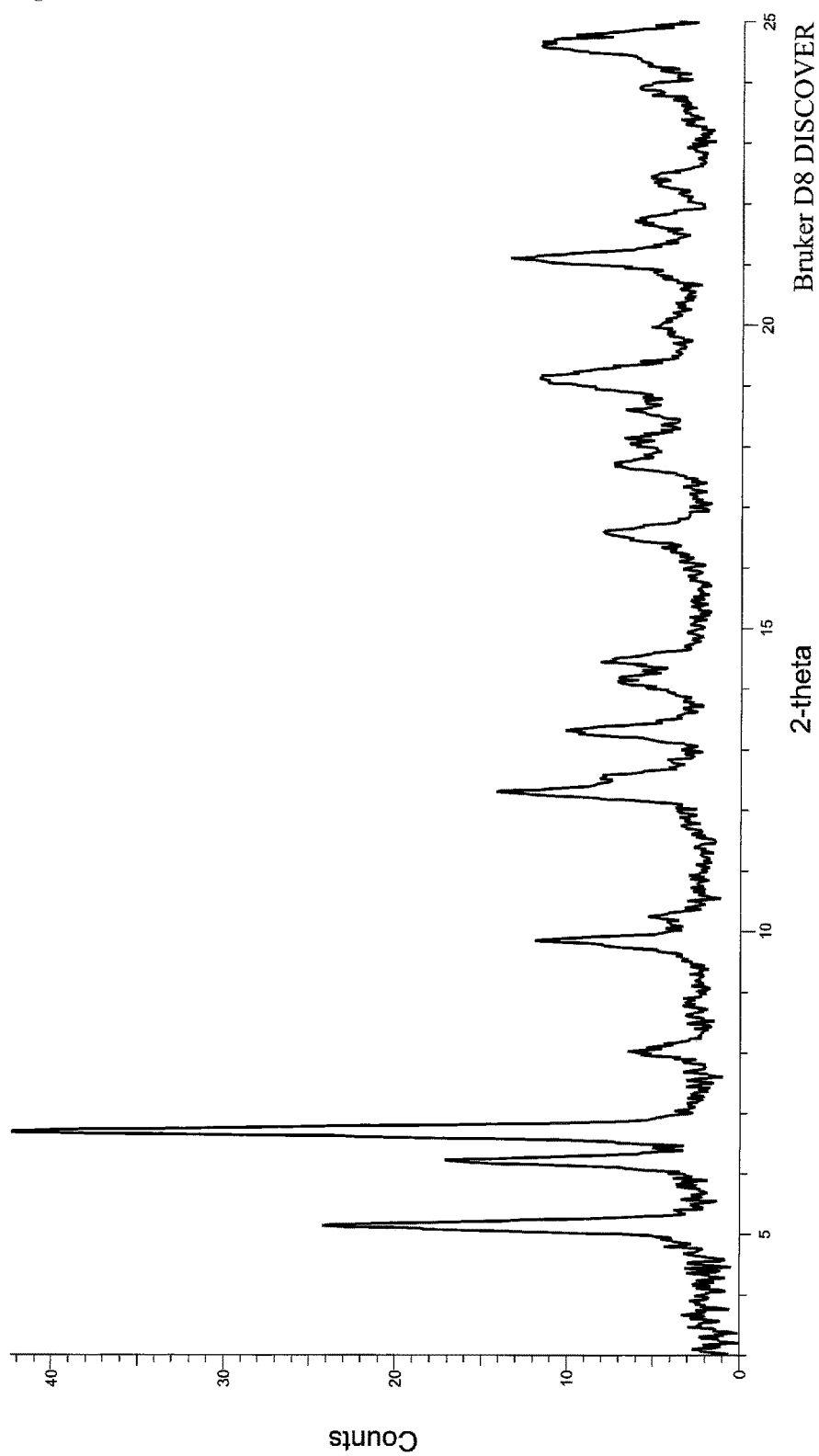

[Figure 22]
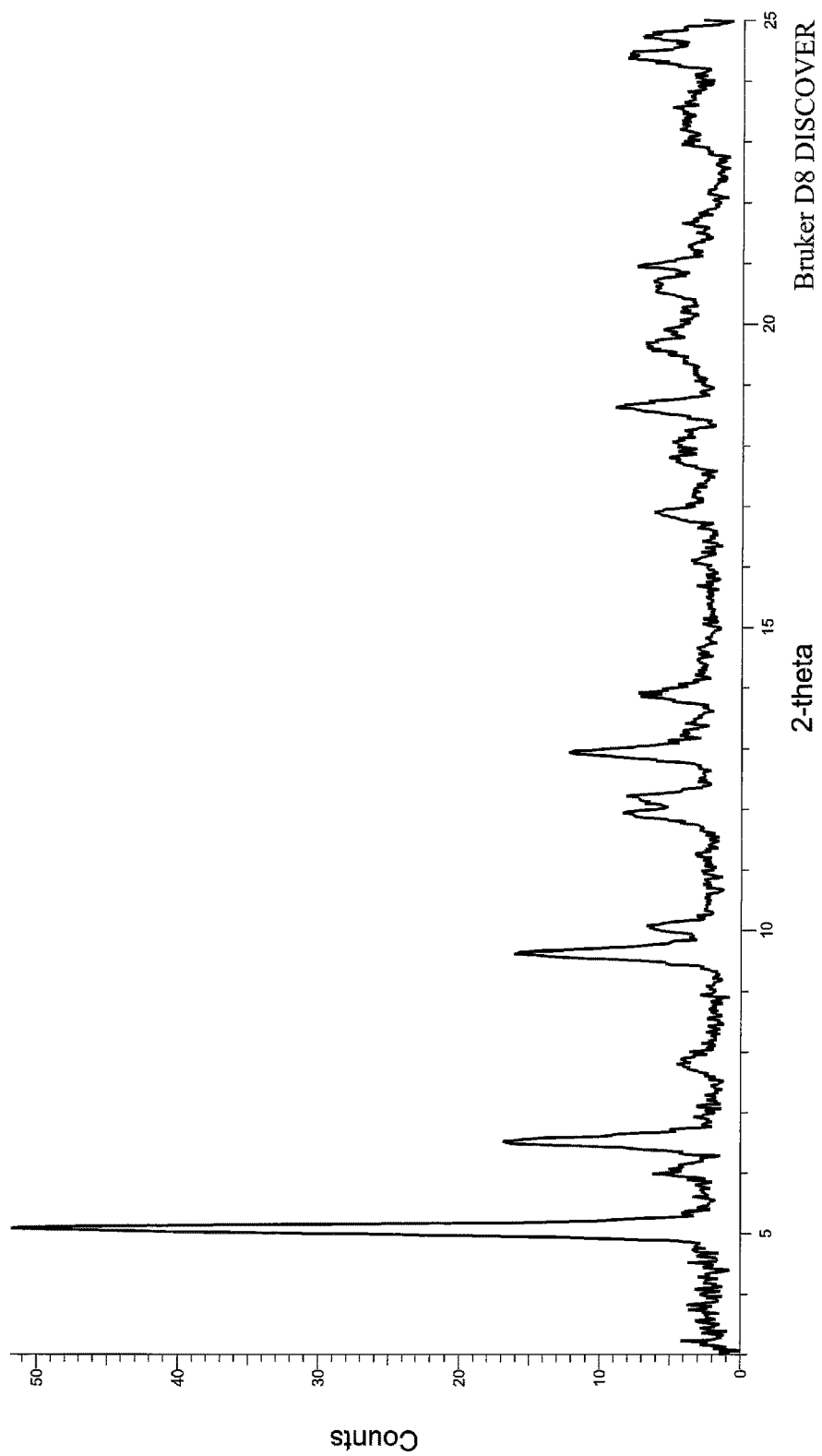

[Figure 23]
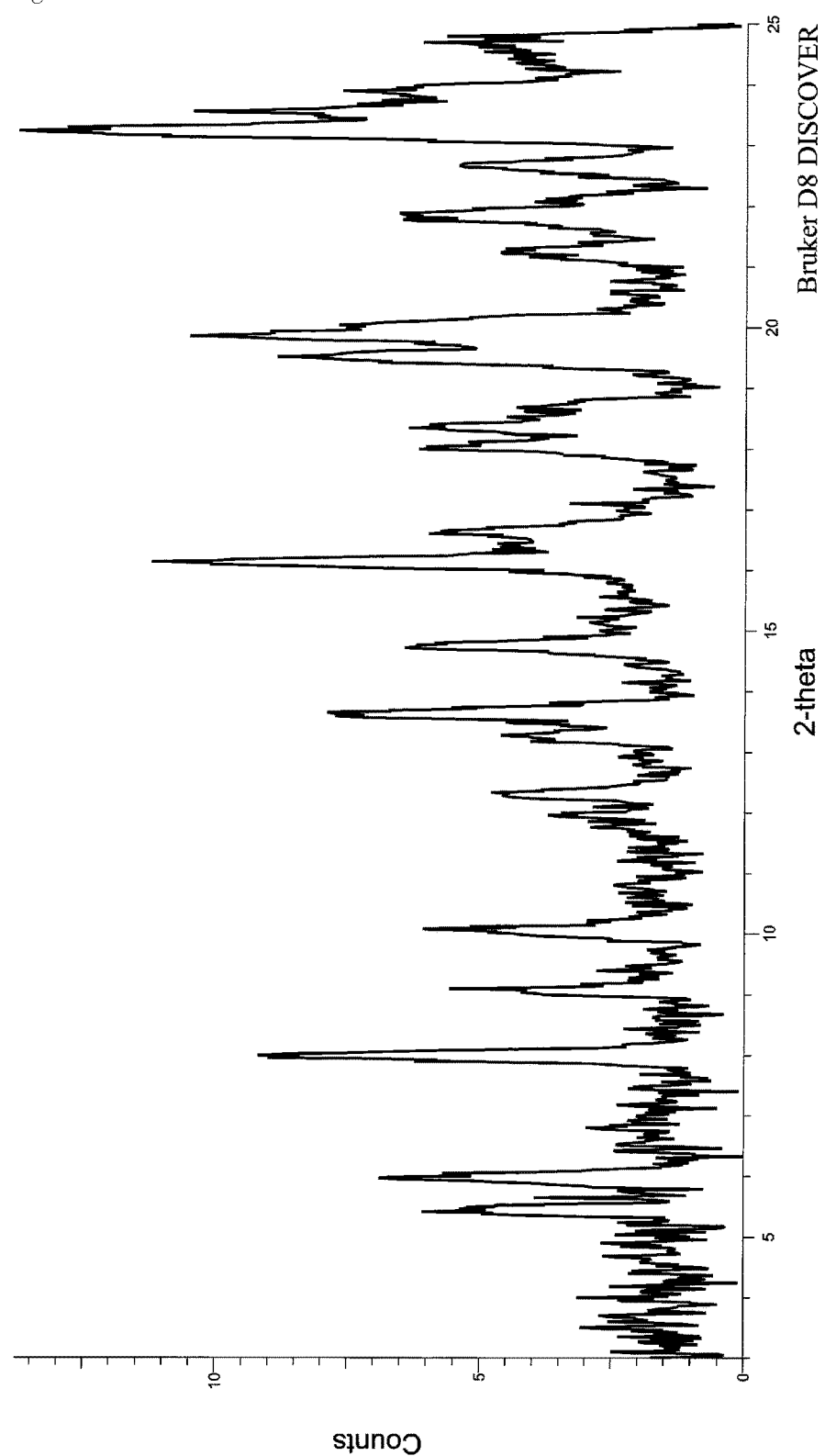

[Figure 24]
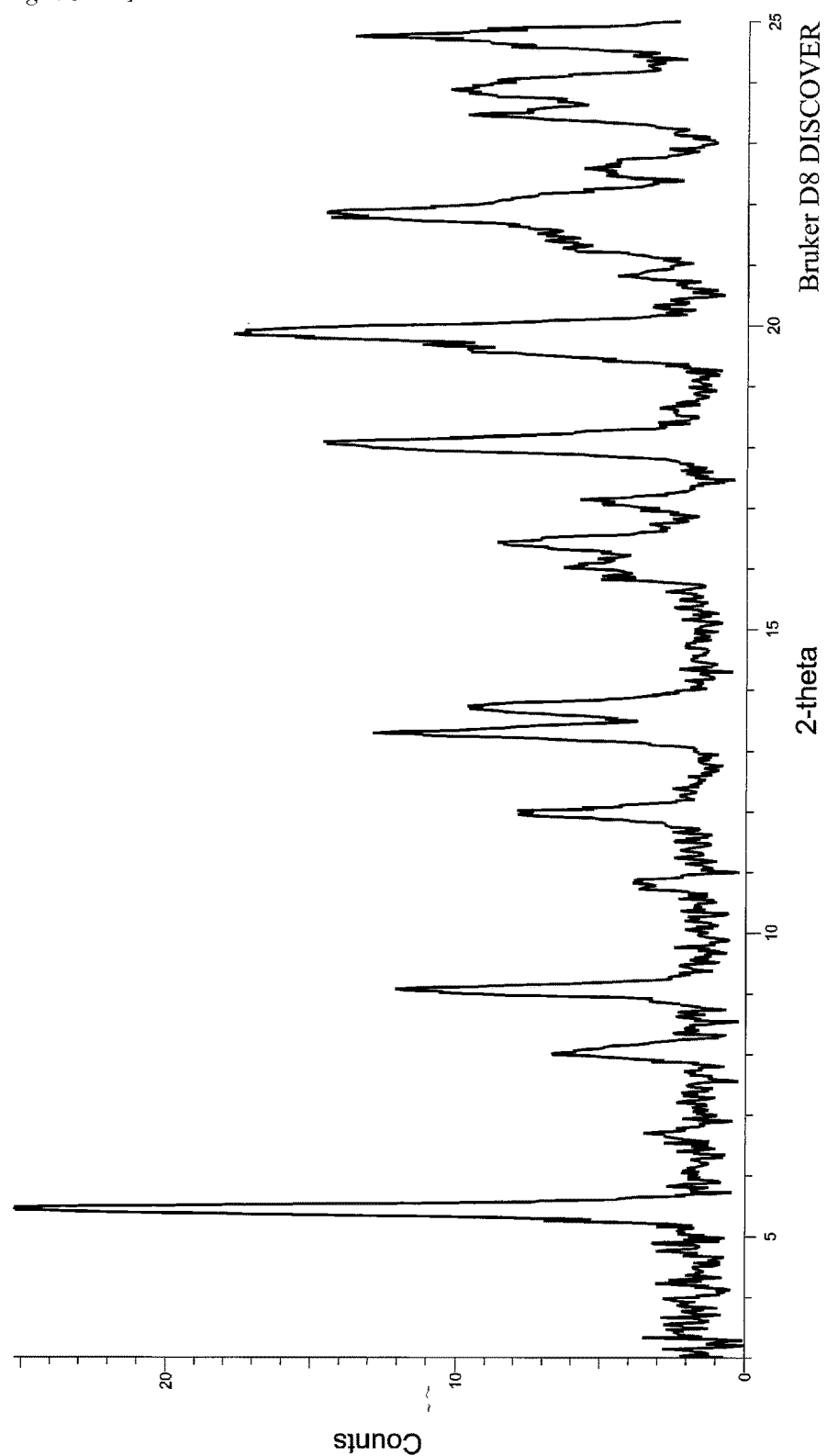

[Figure 25]
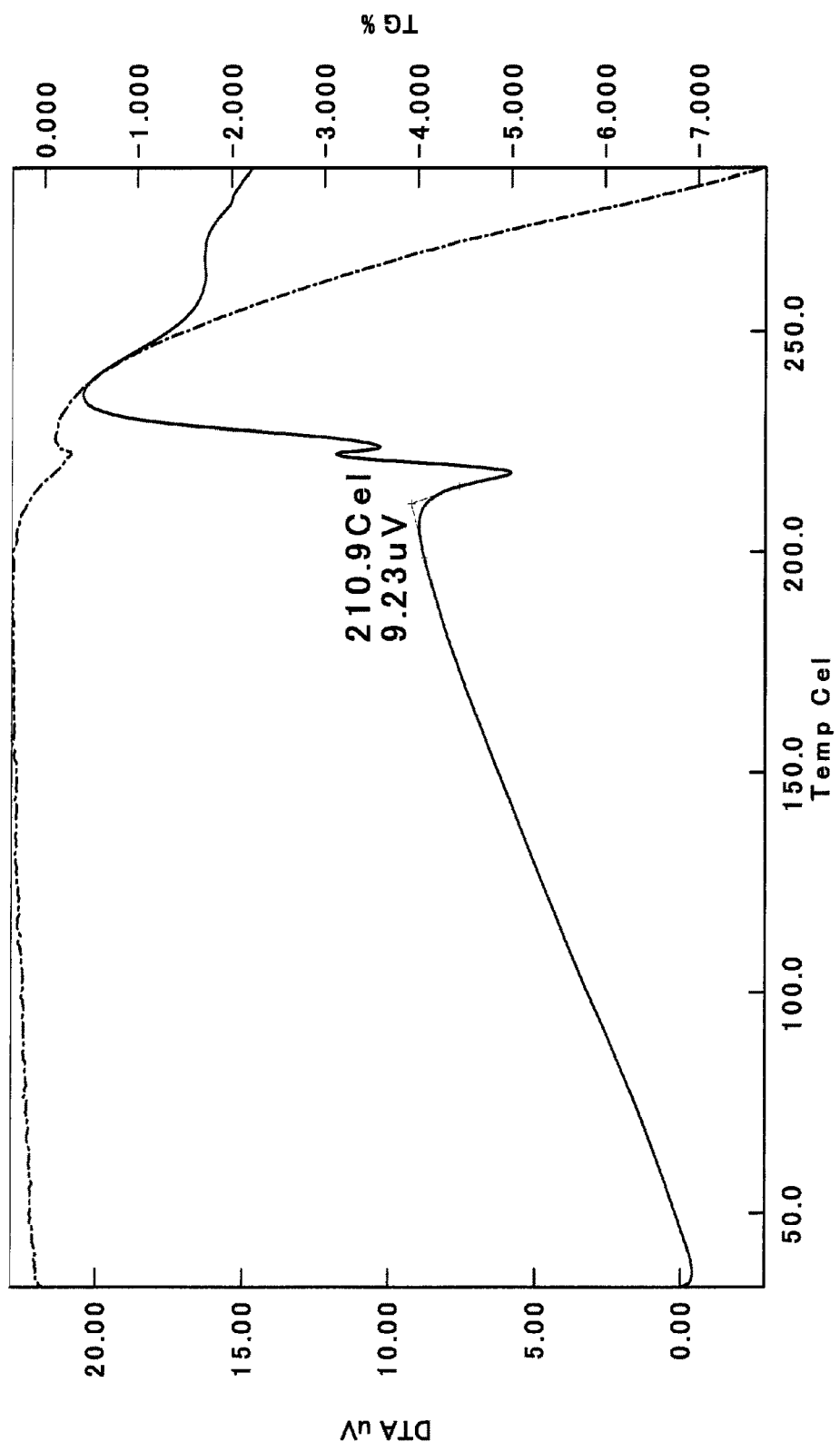

[Figure 26]
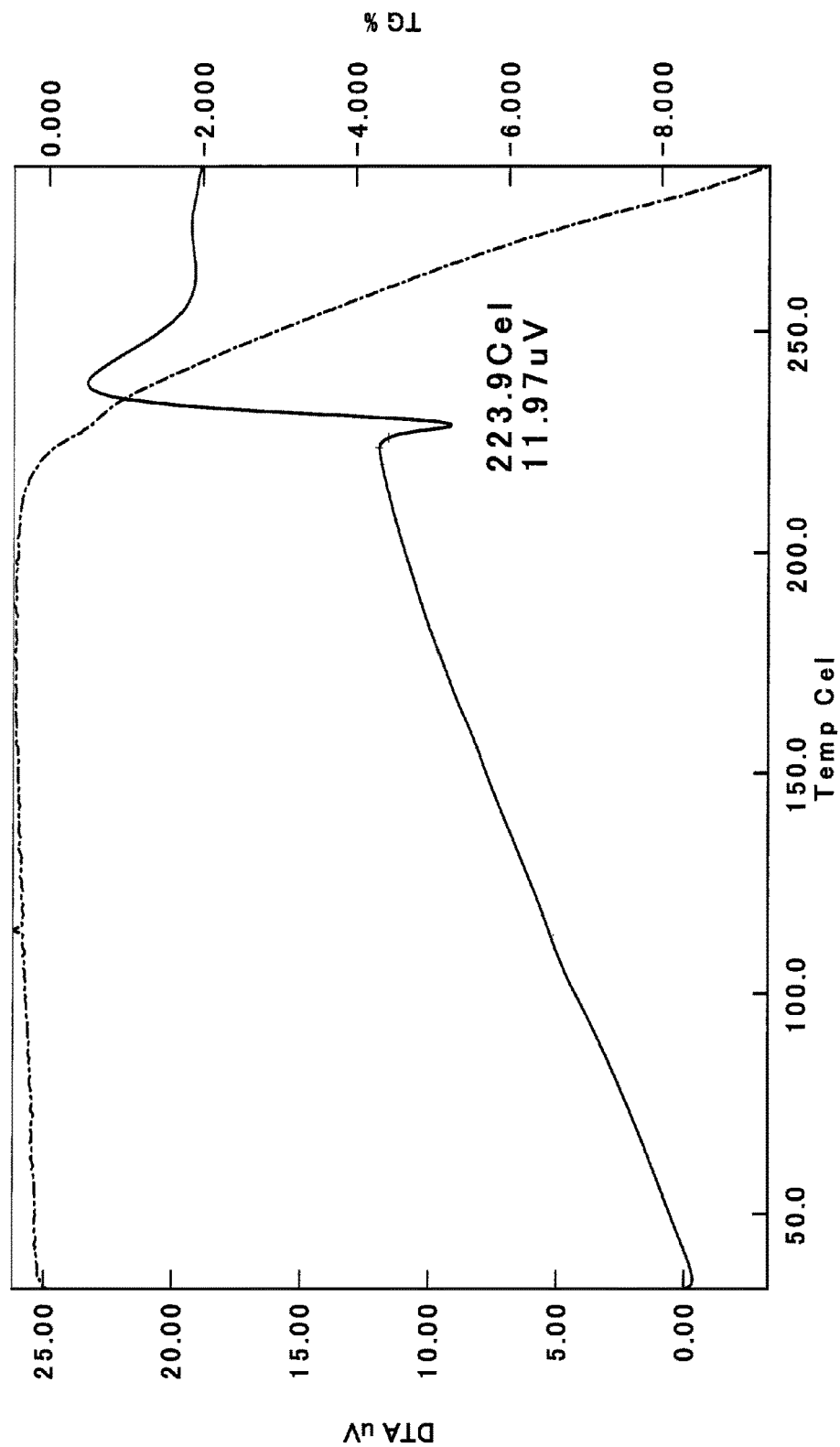

[Figure 27]
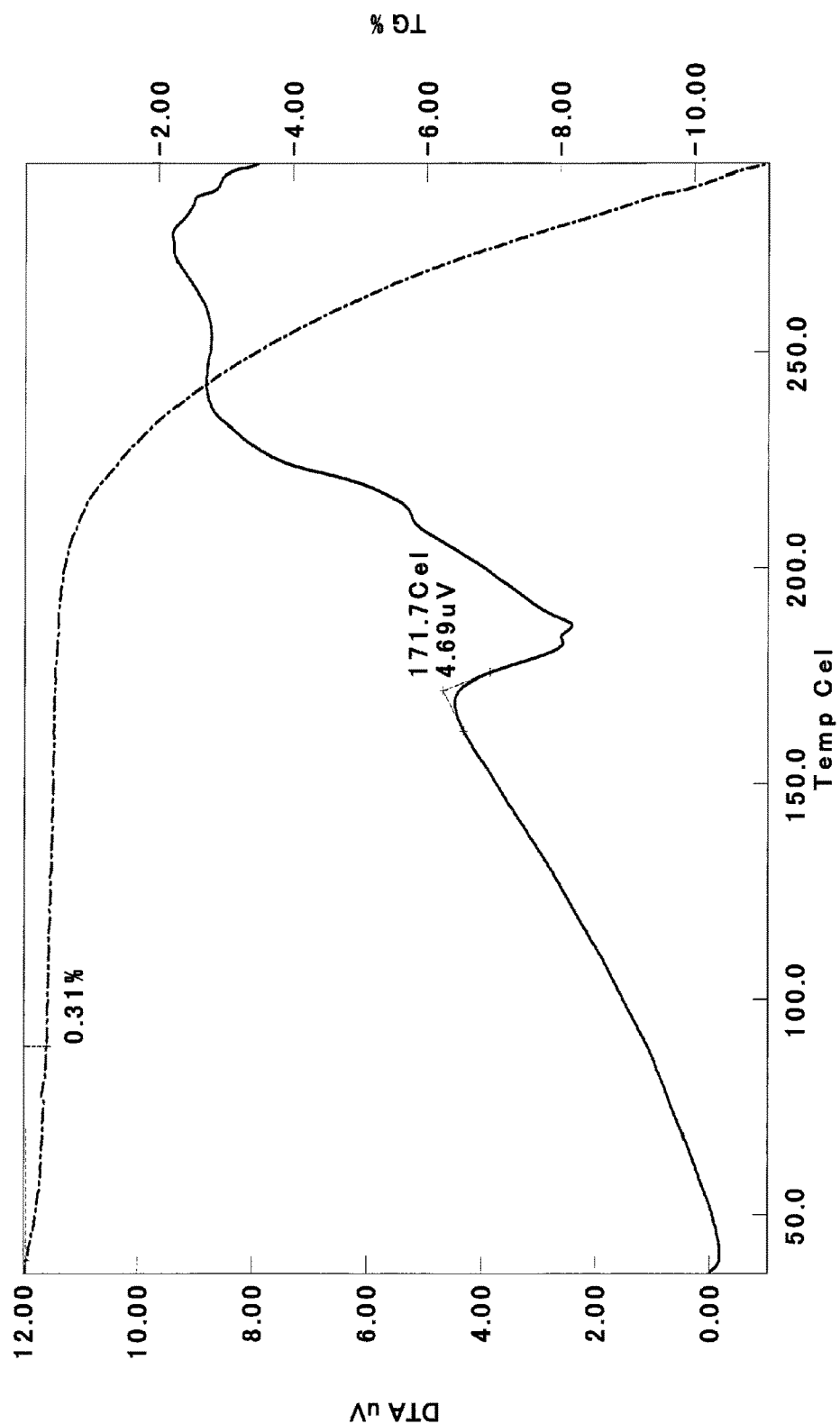

[Figure 28]
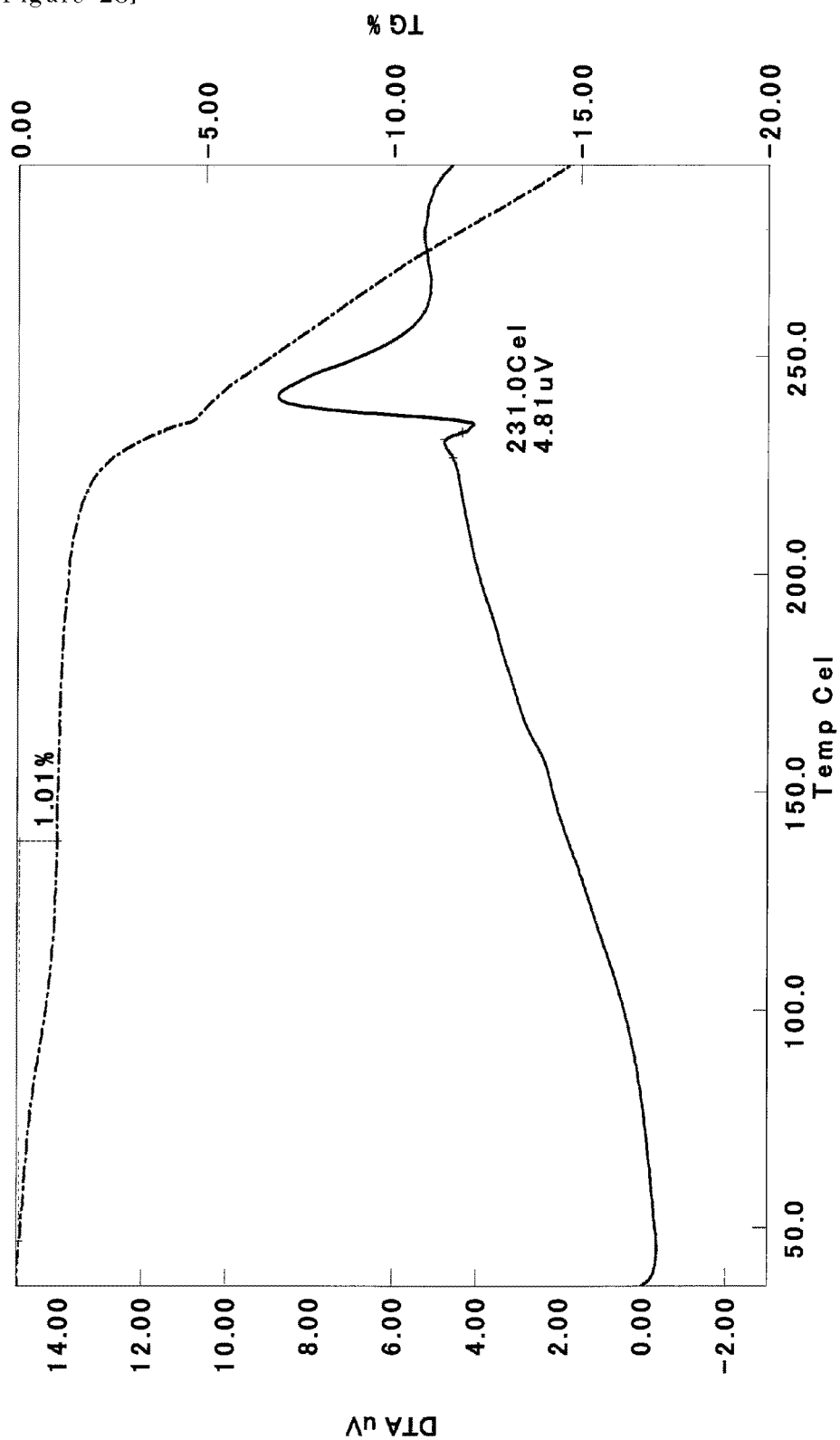

[Figure 29]
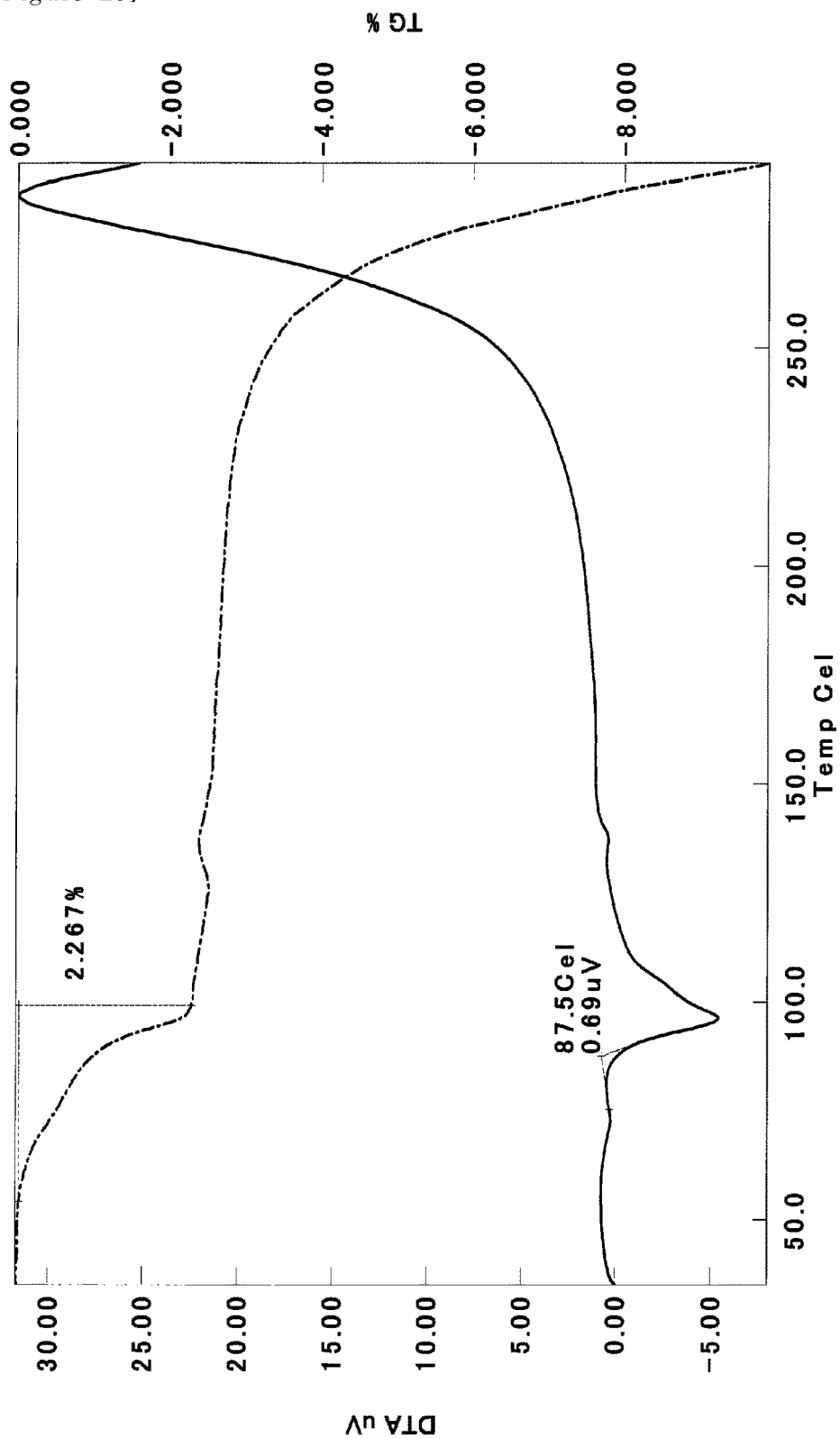

[Figure 30]
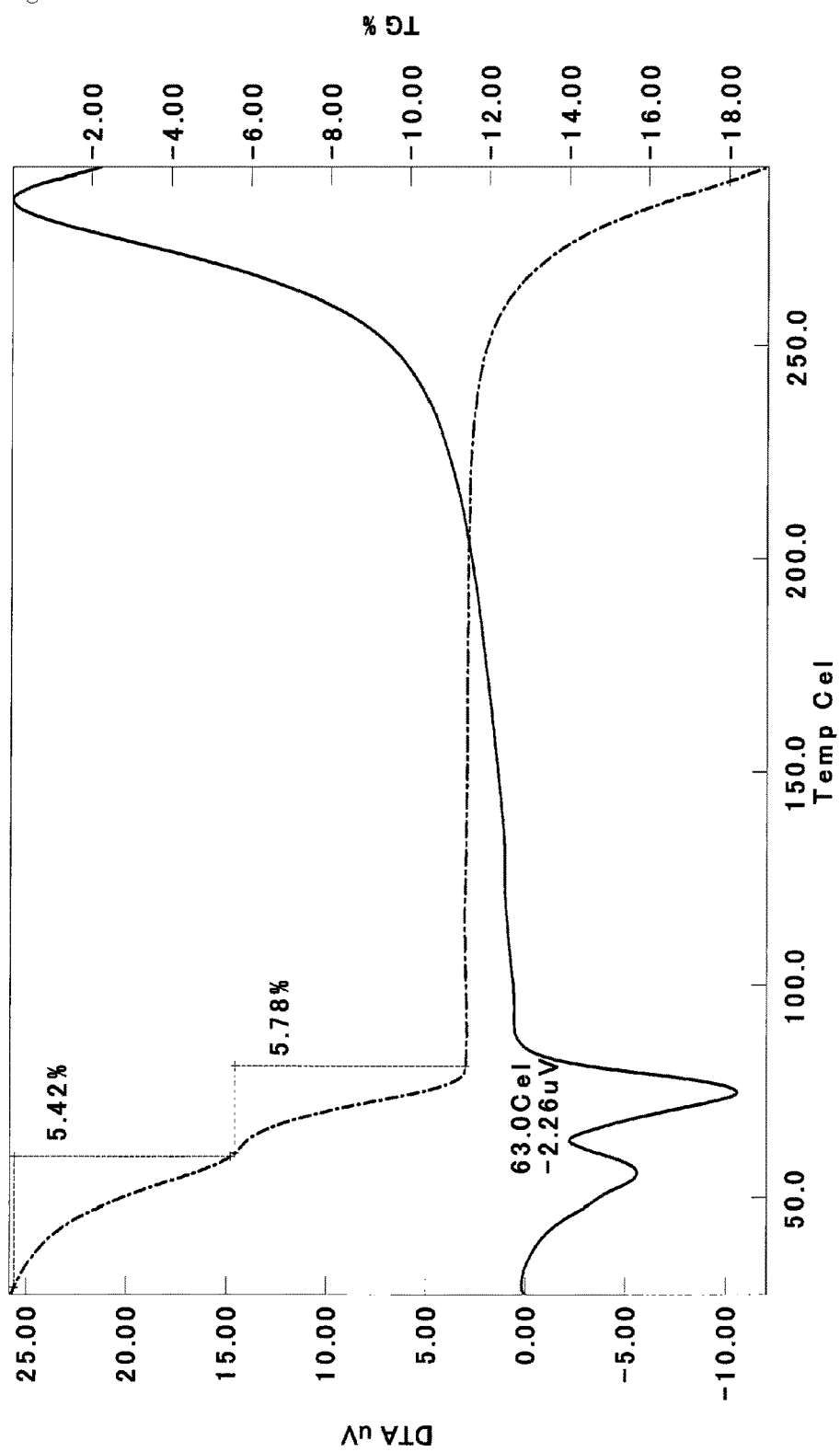

[Figure 31]
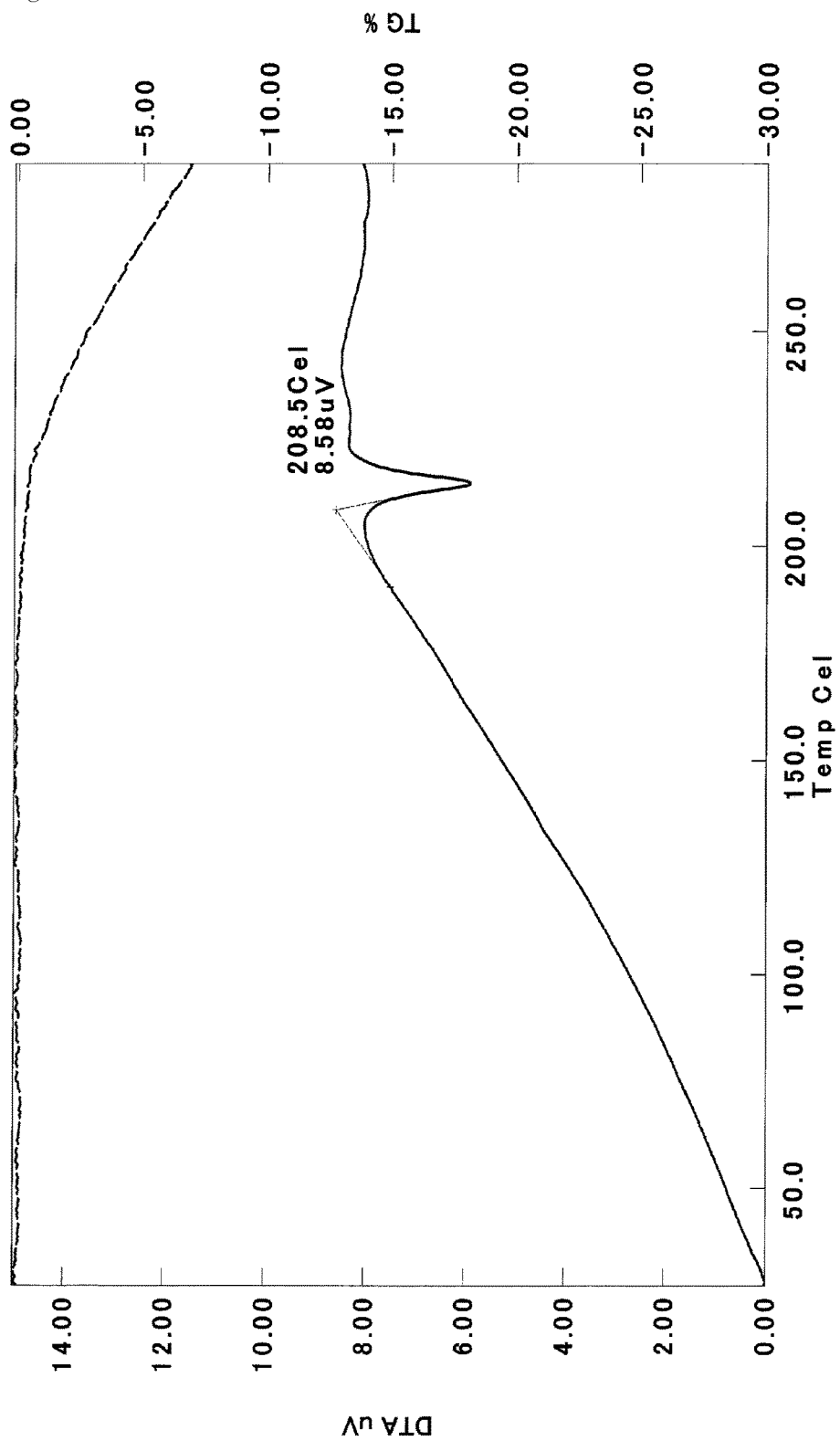

[Figure 32]
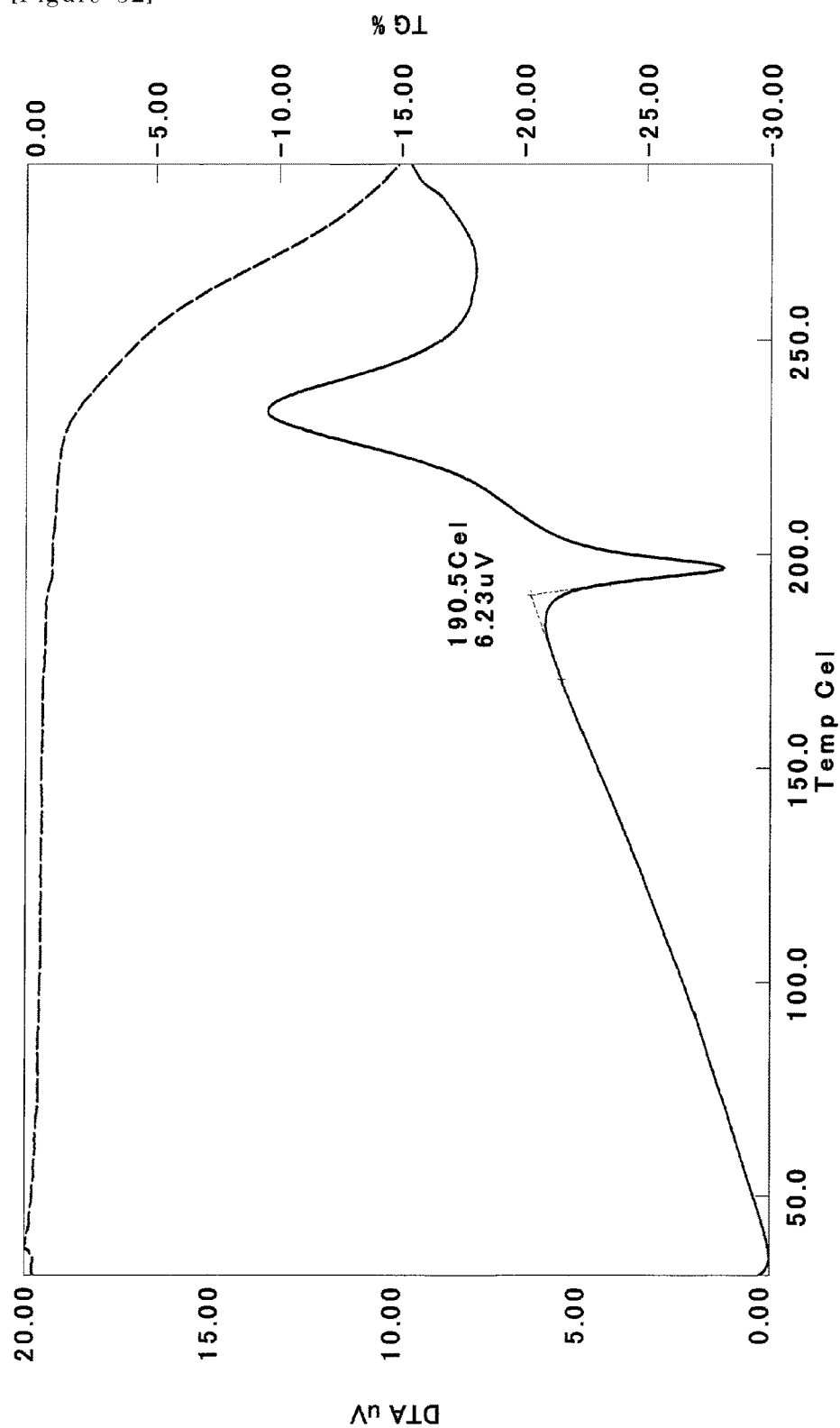

[Figure 33]
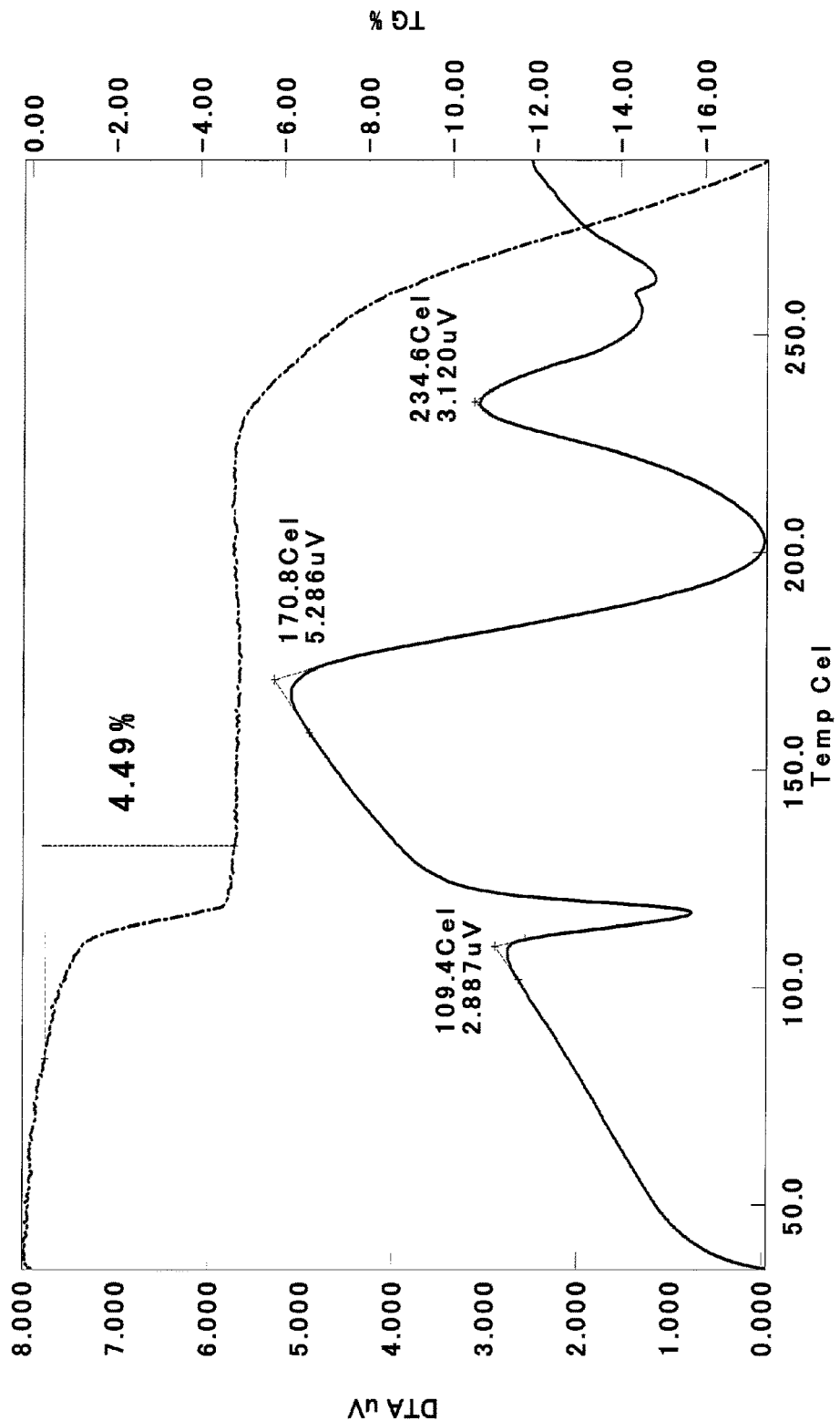

[Figure 34]
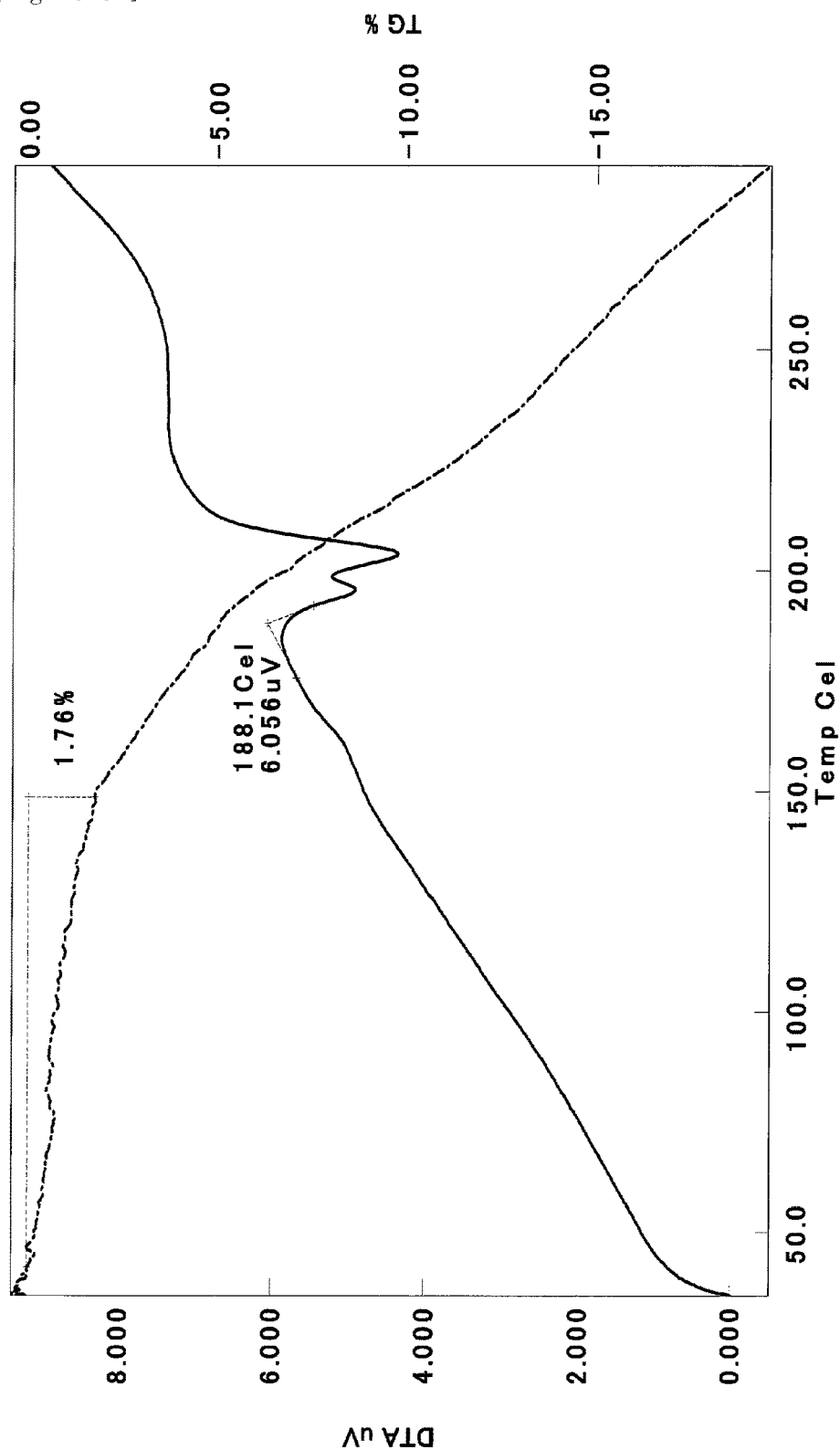

[Figure 35]
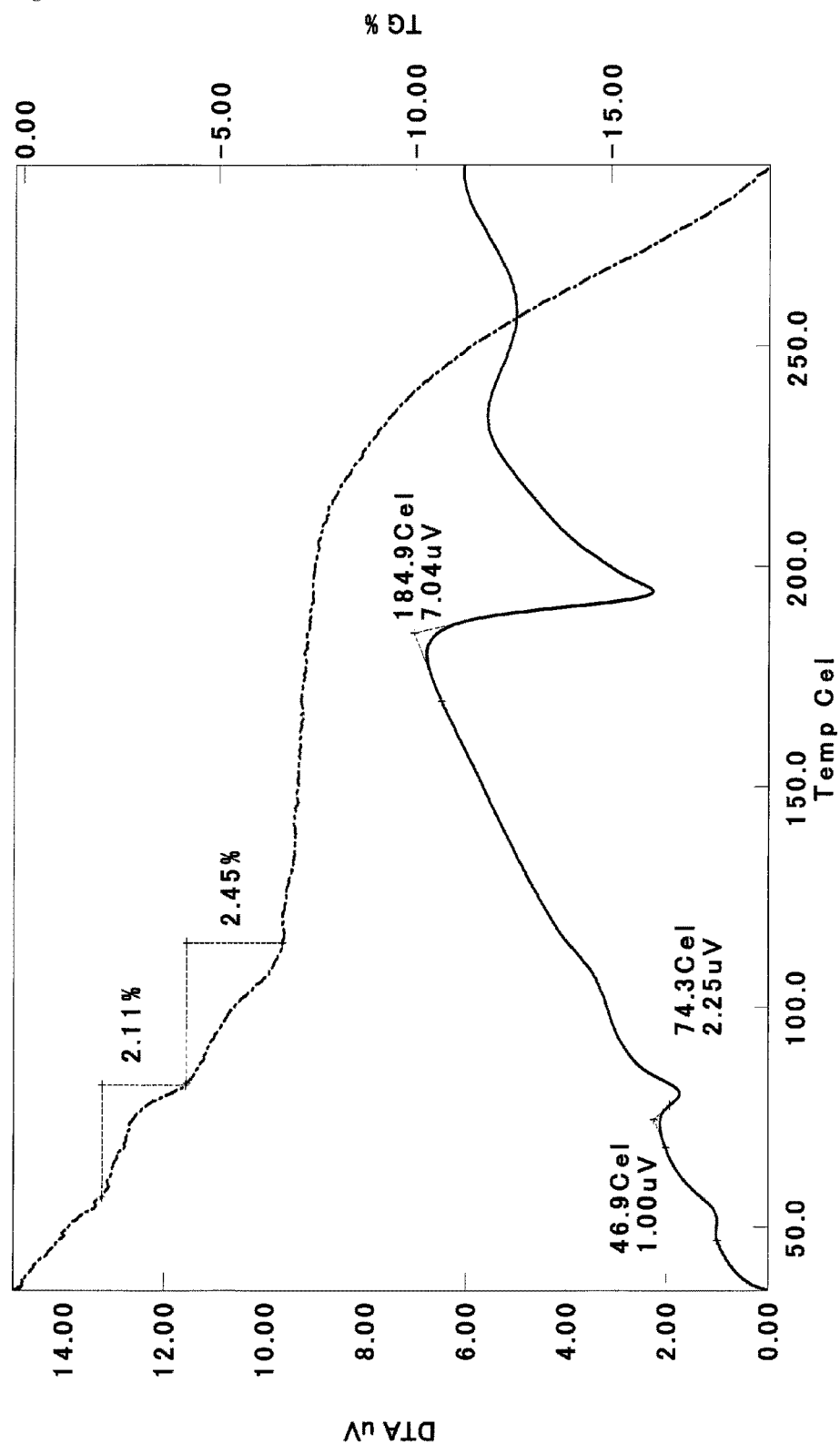

[Figure 36]
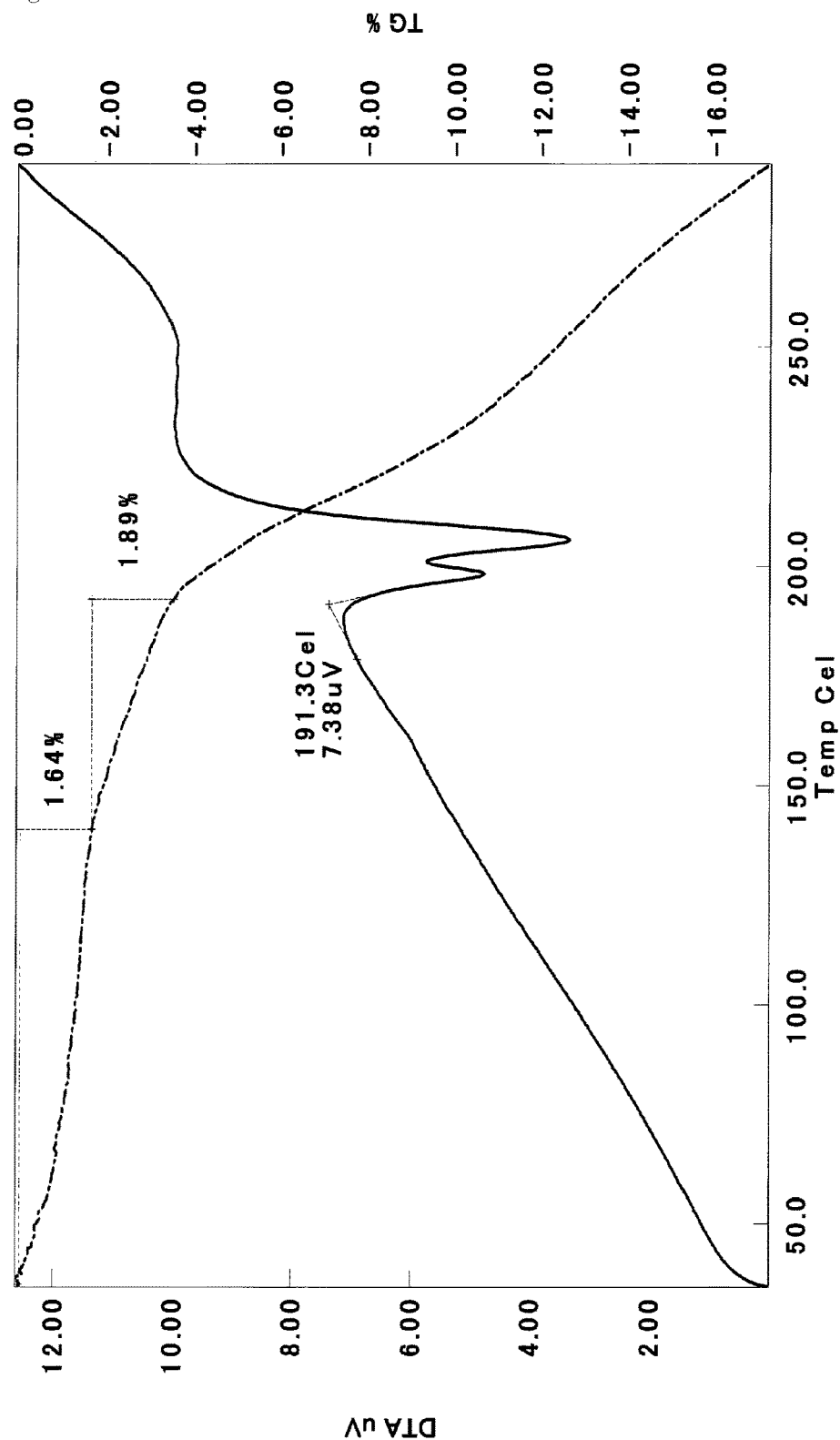

[Figure 37]
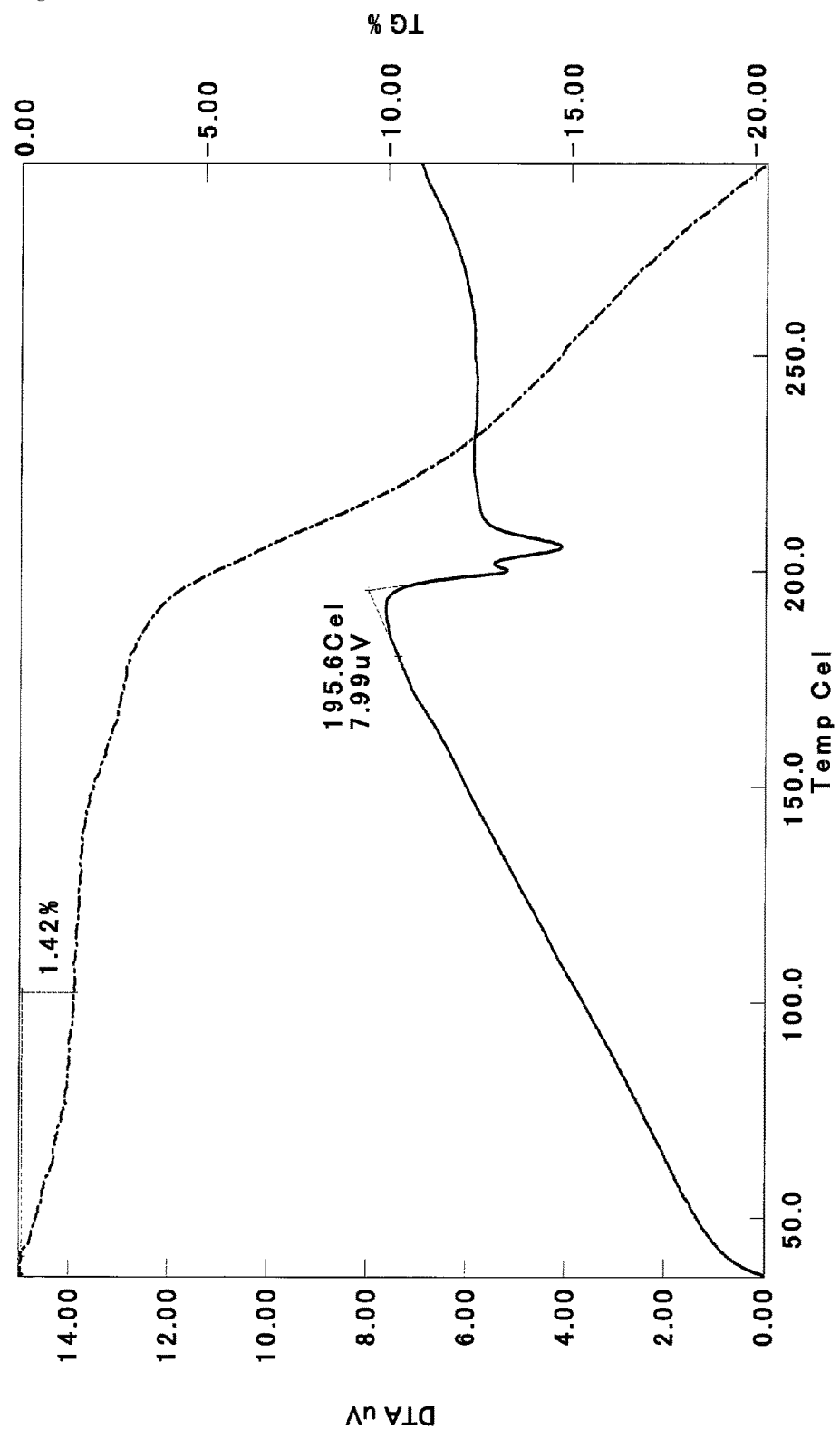

[Figure 38]
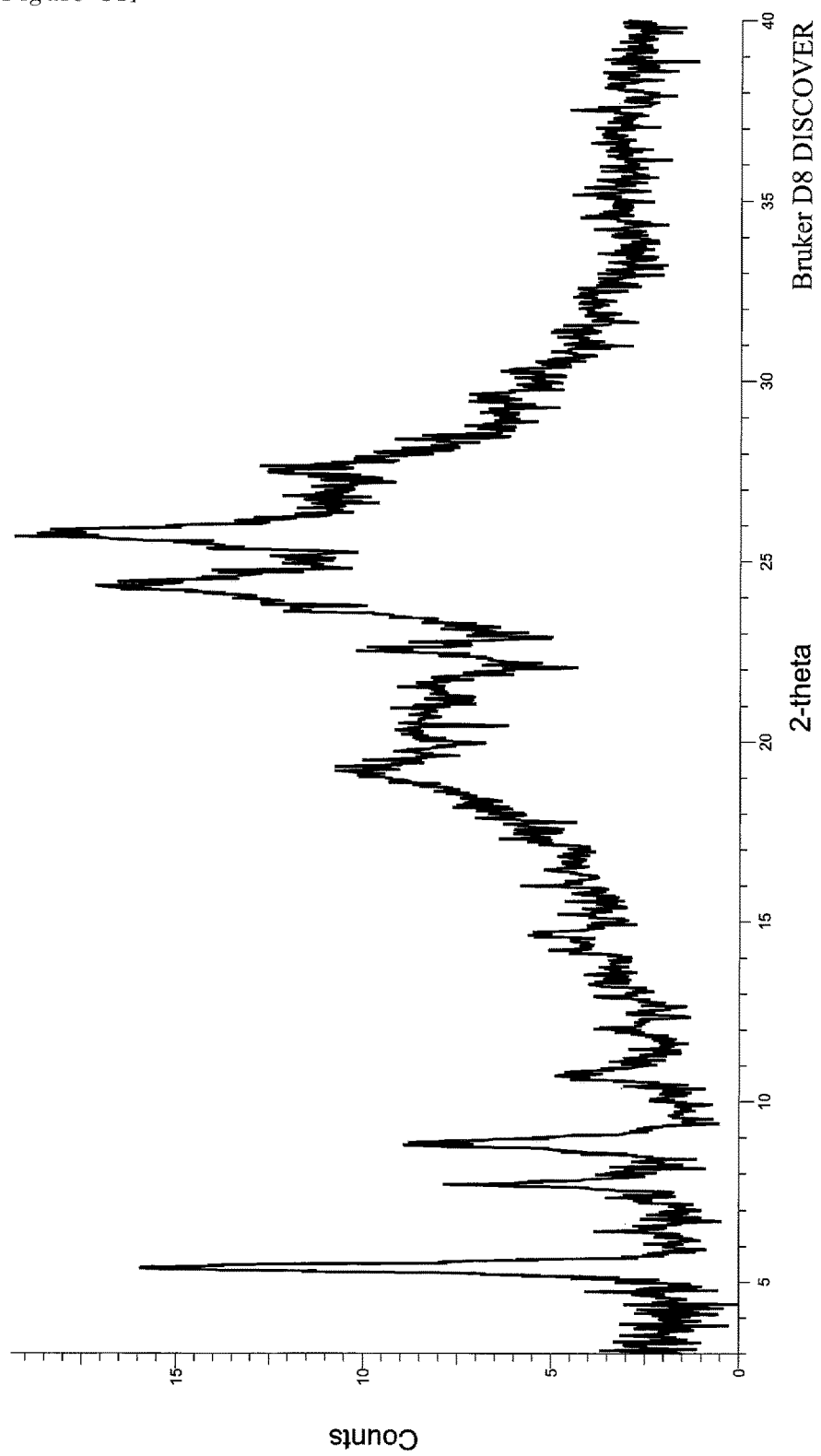

[Figure 39]
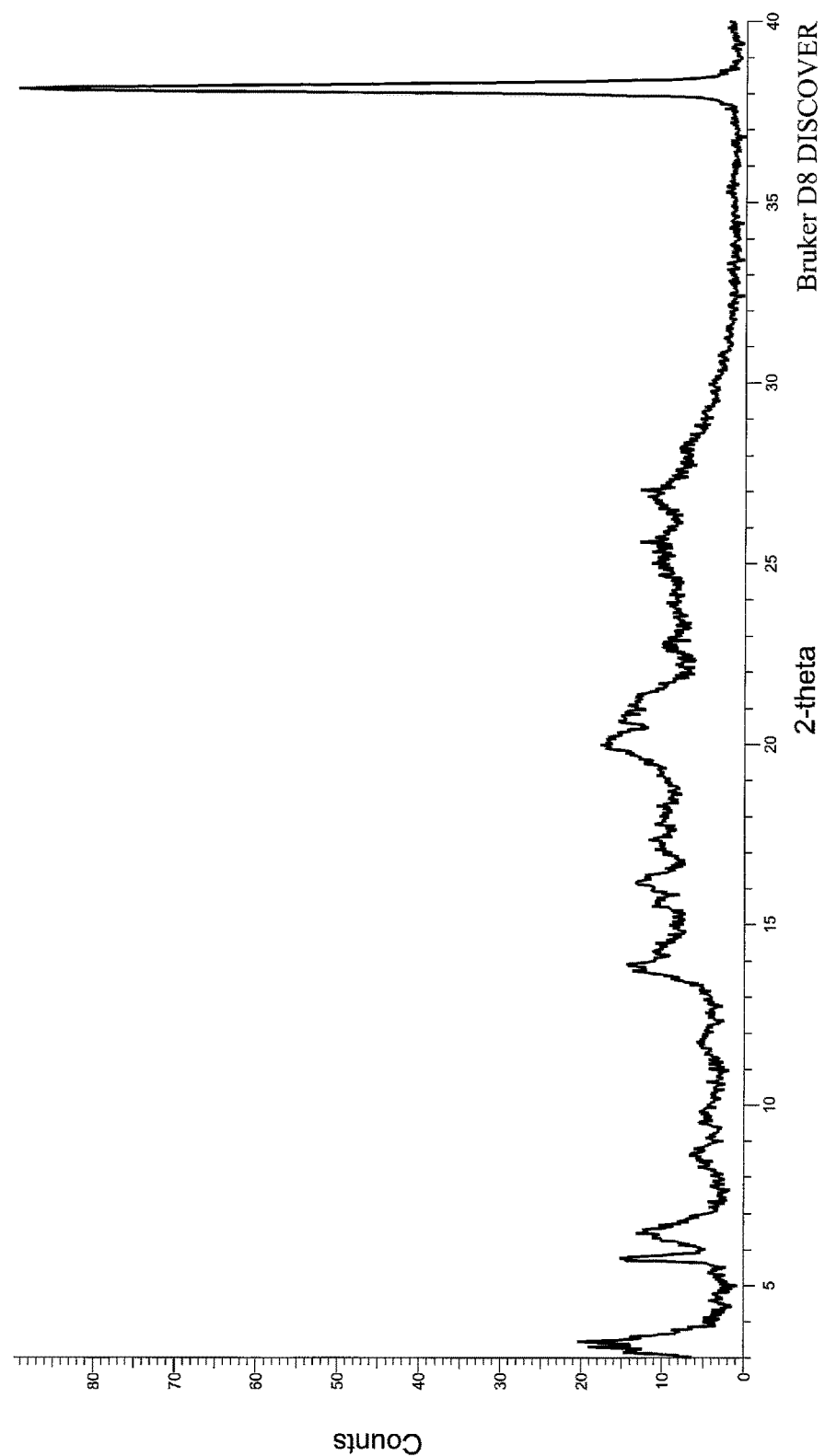

[Figure 40]
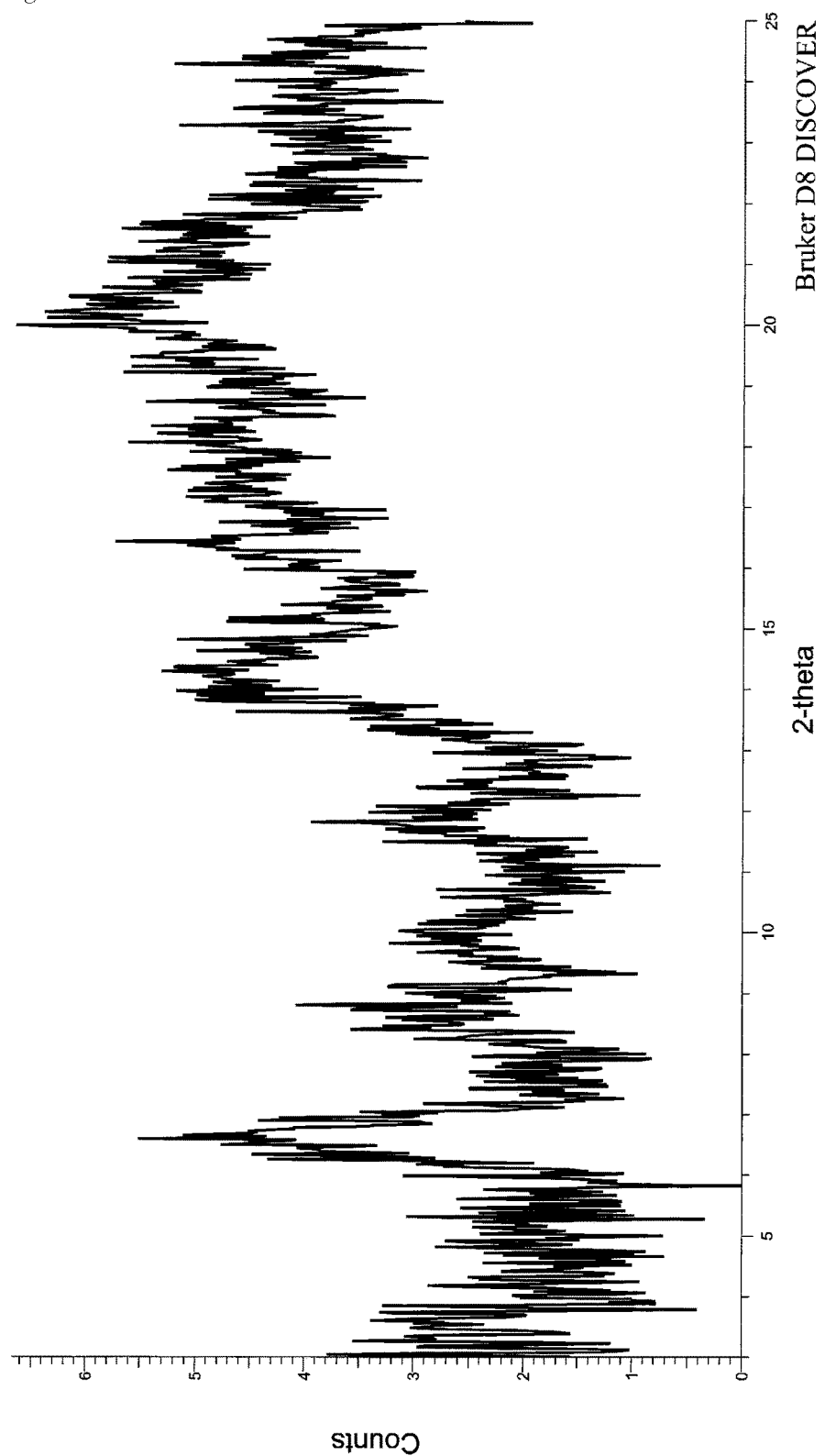

[Figure 41]
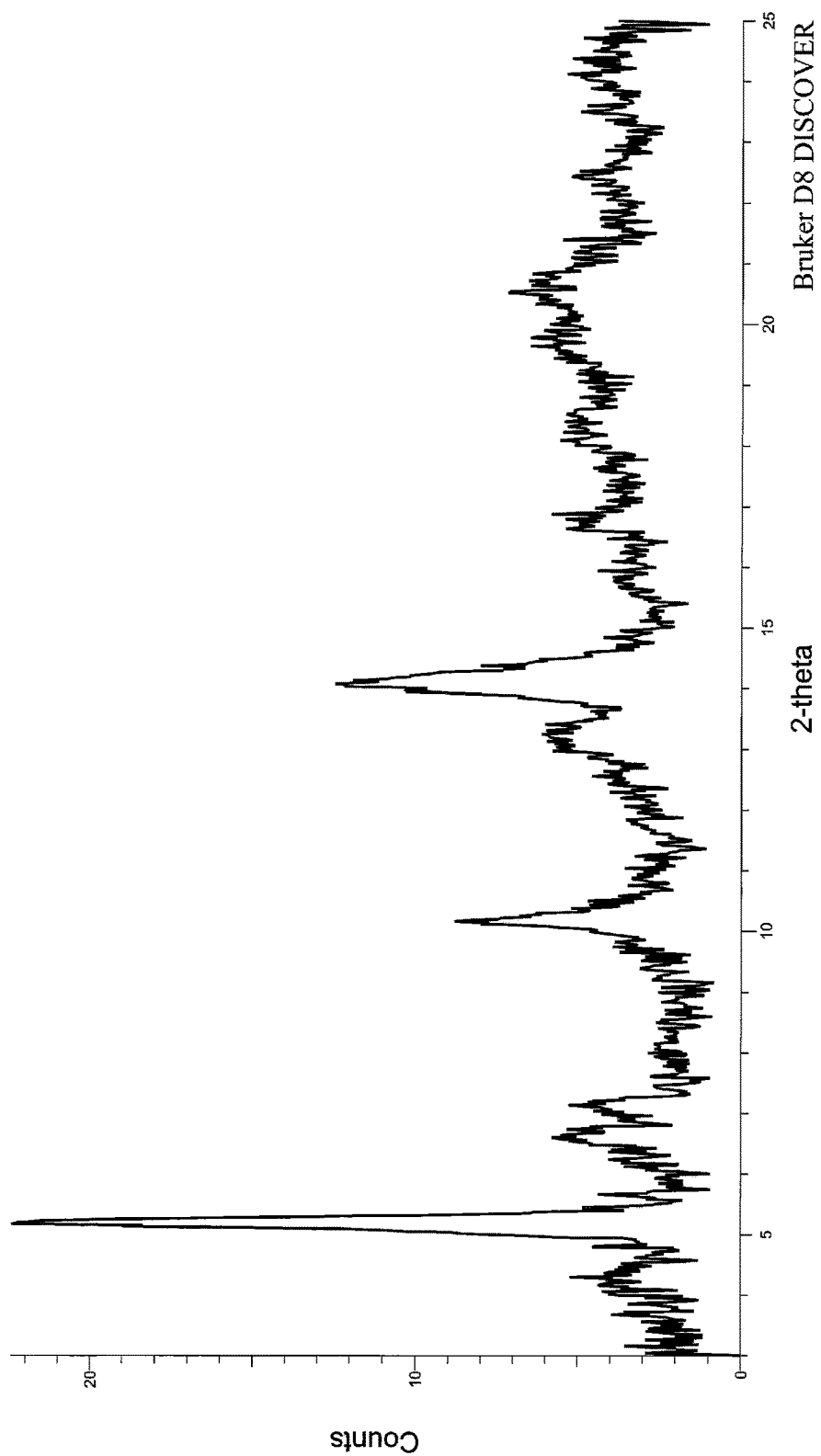

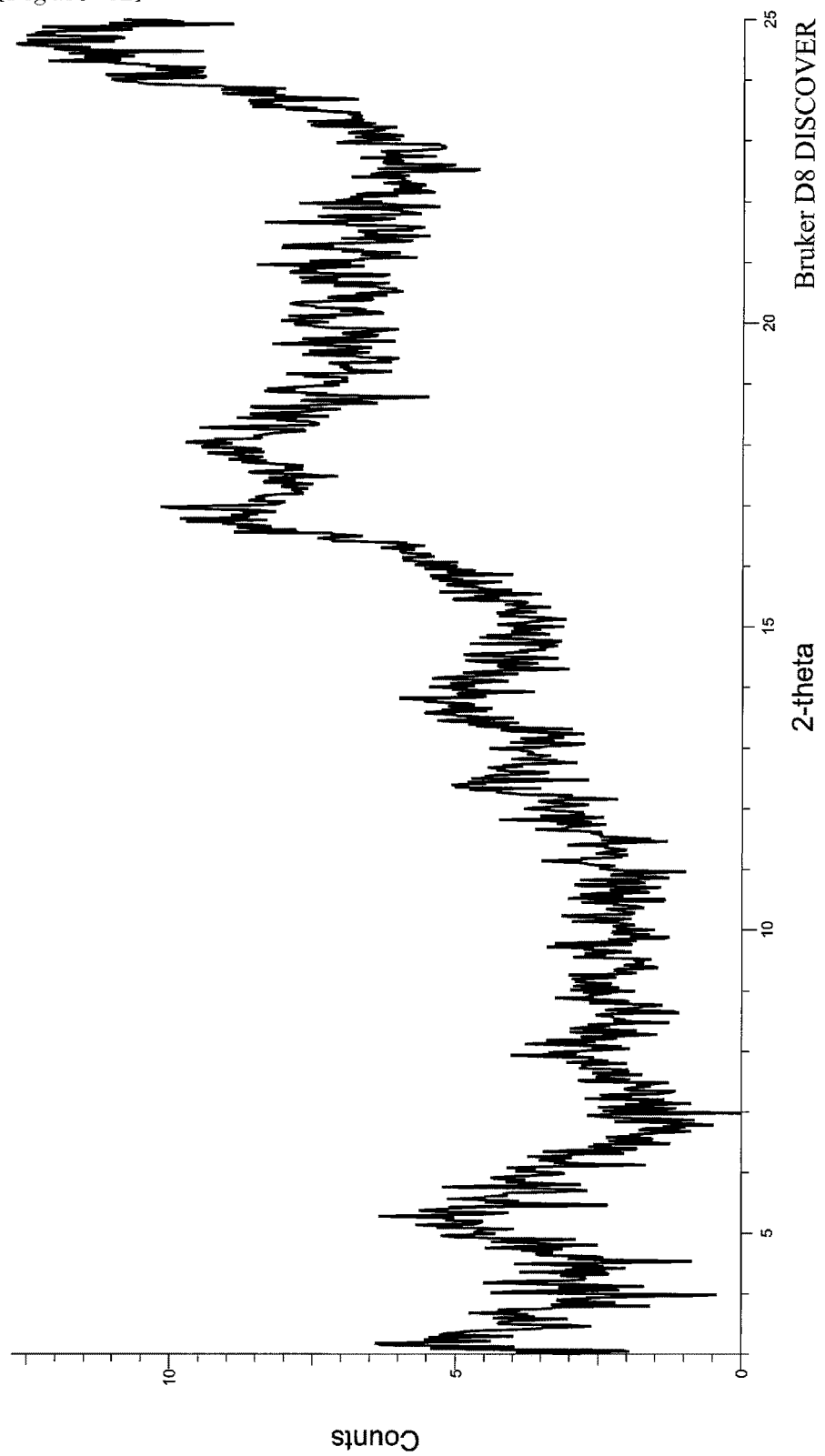
[Figure 42]

[Figure 43]
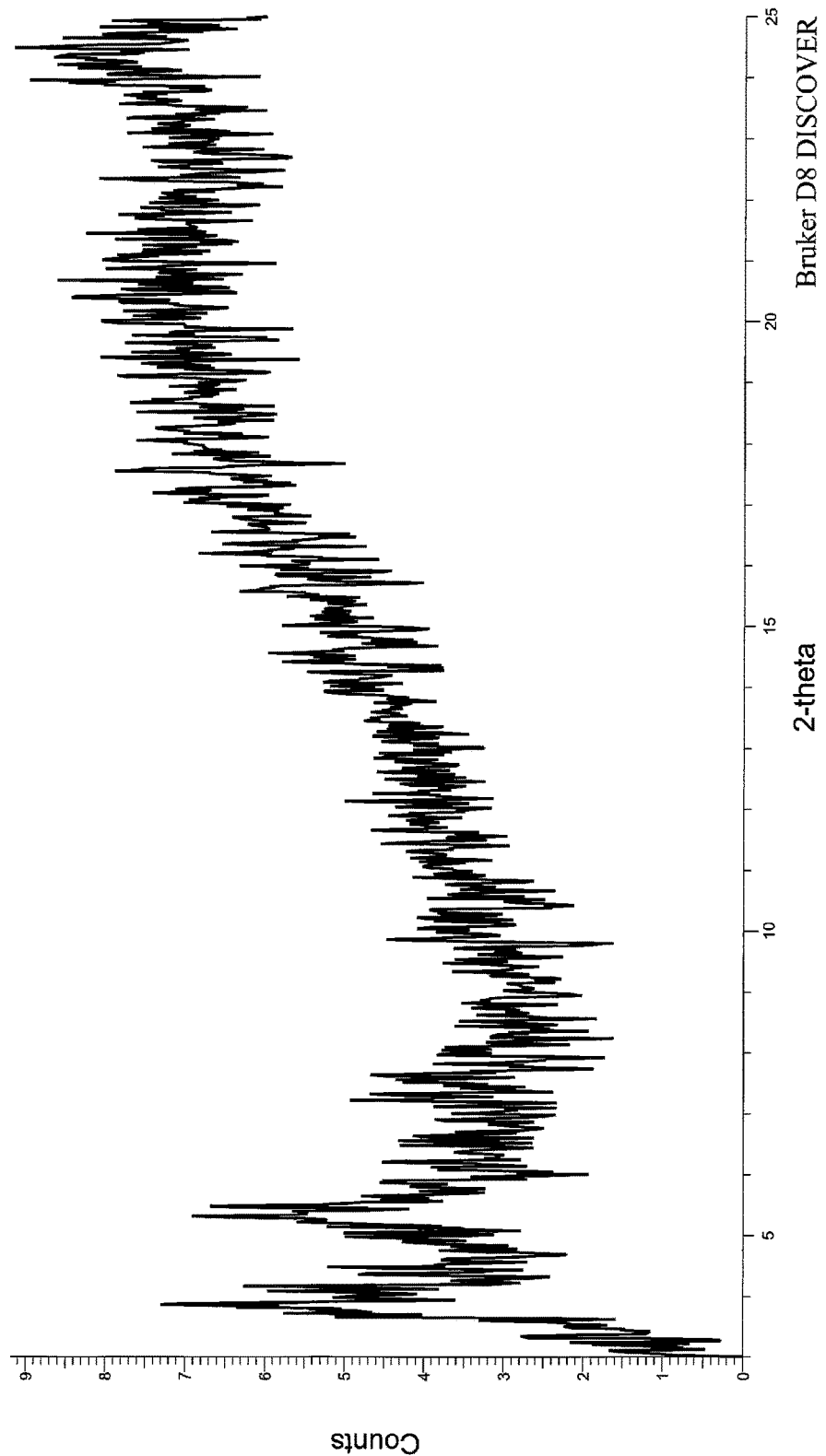

[Figure 44]
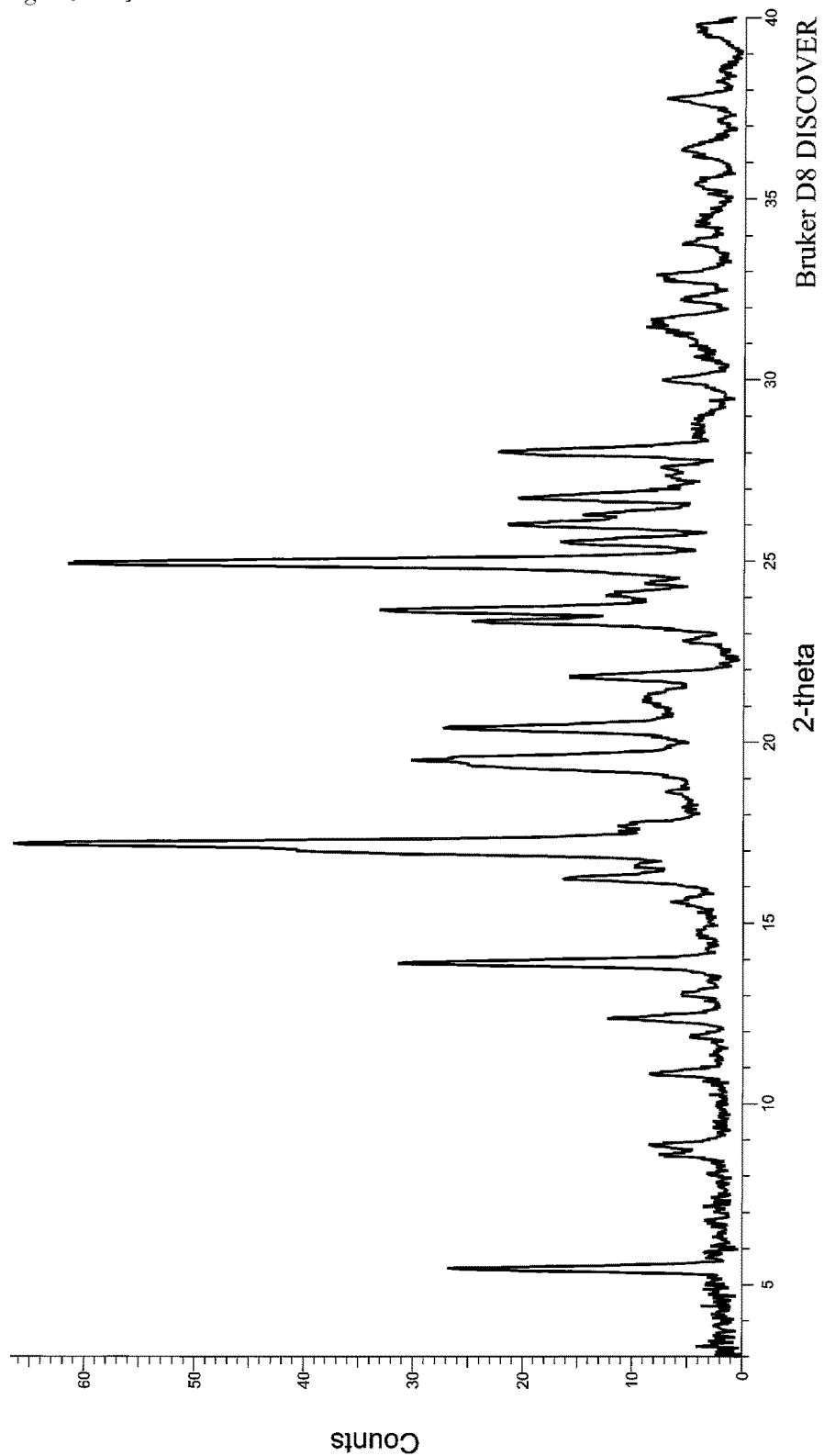

[Figure 45]
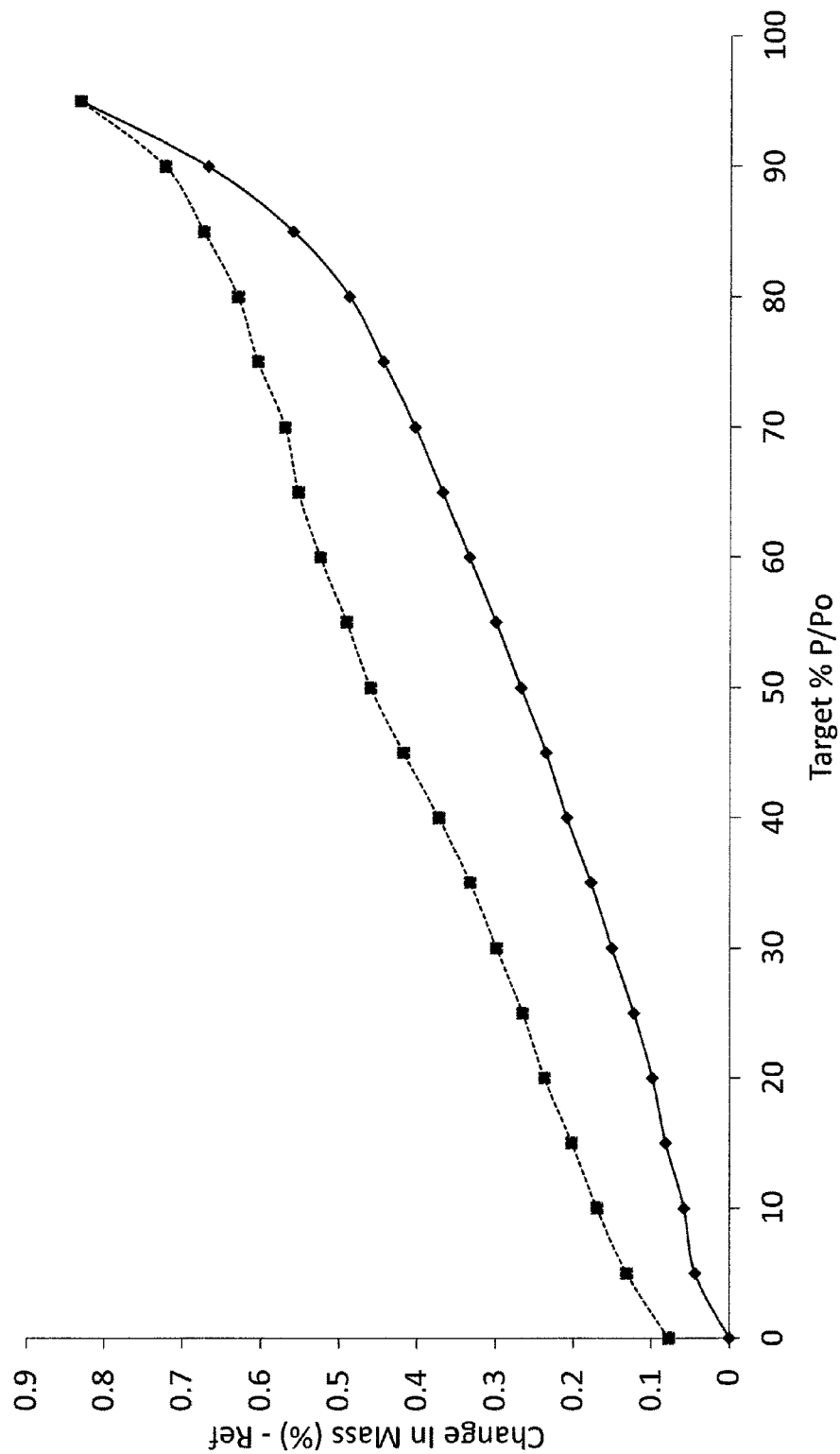

[Figure 46]
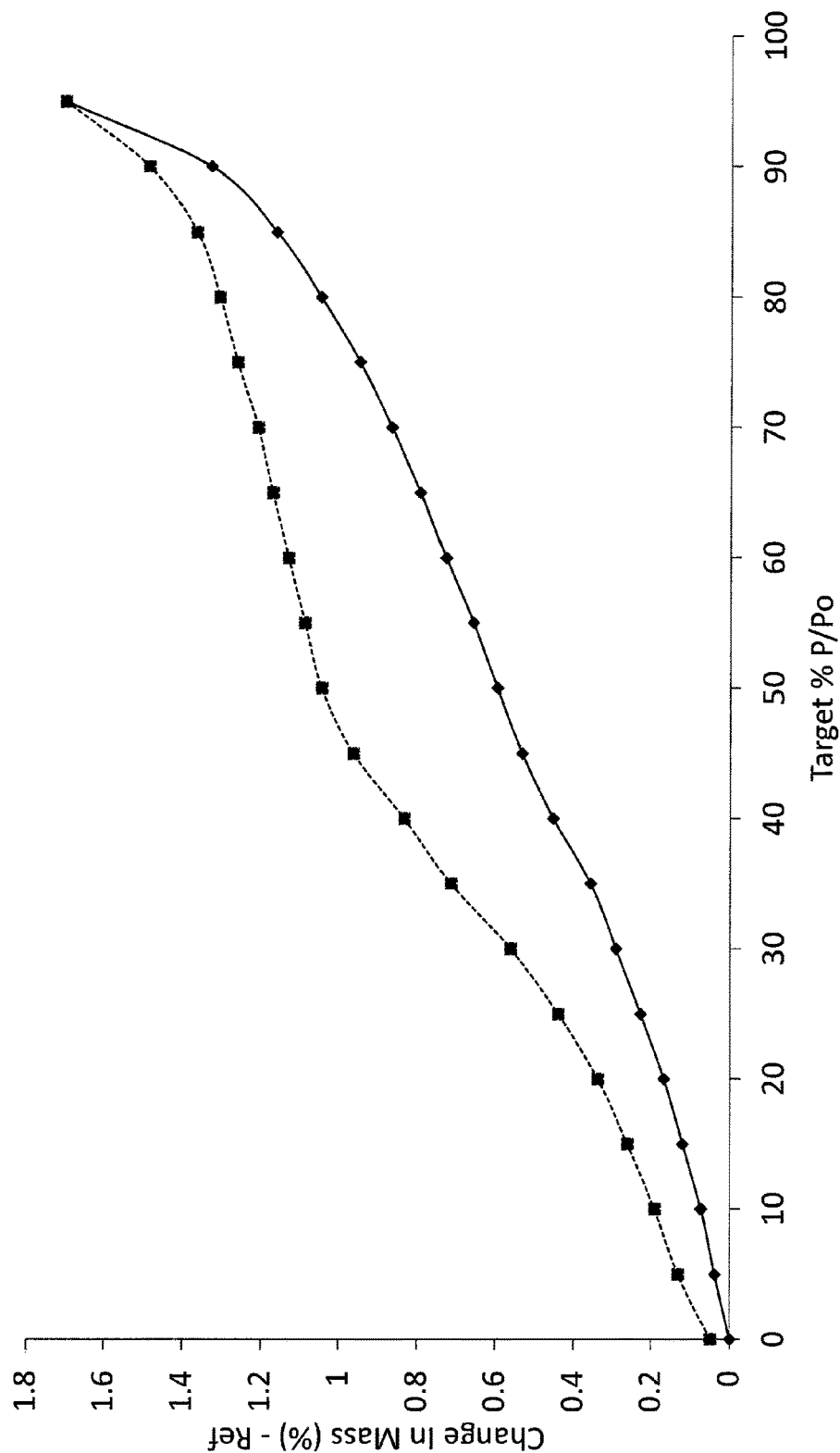

[Figure 47]
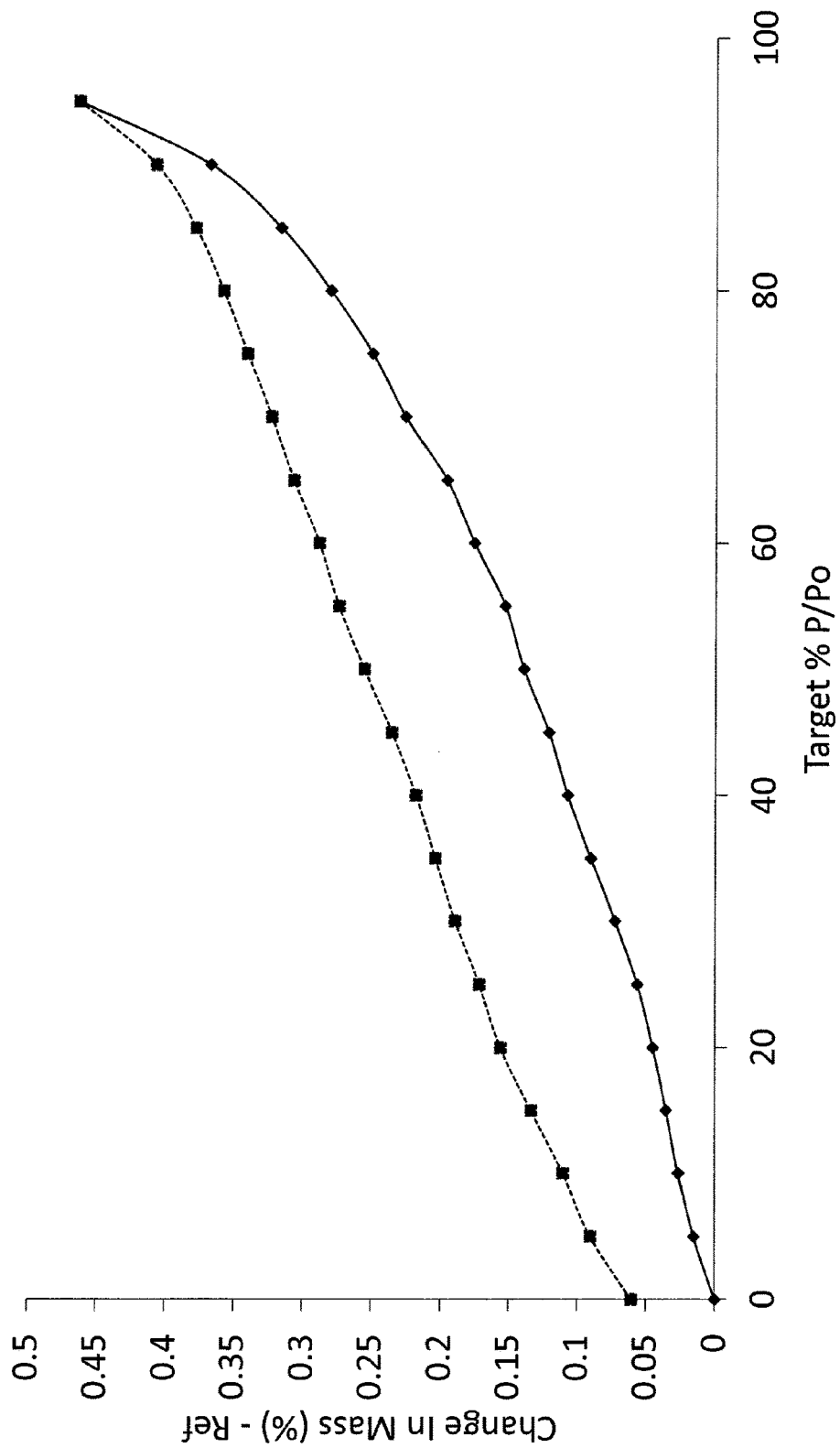

[Figure 48]
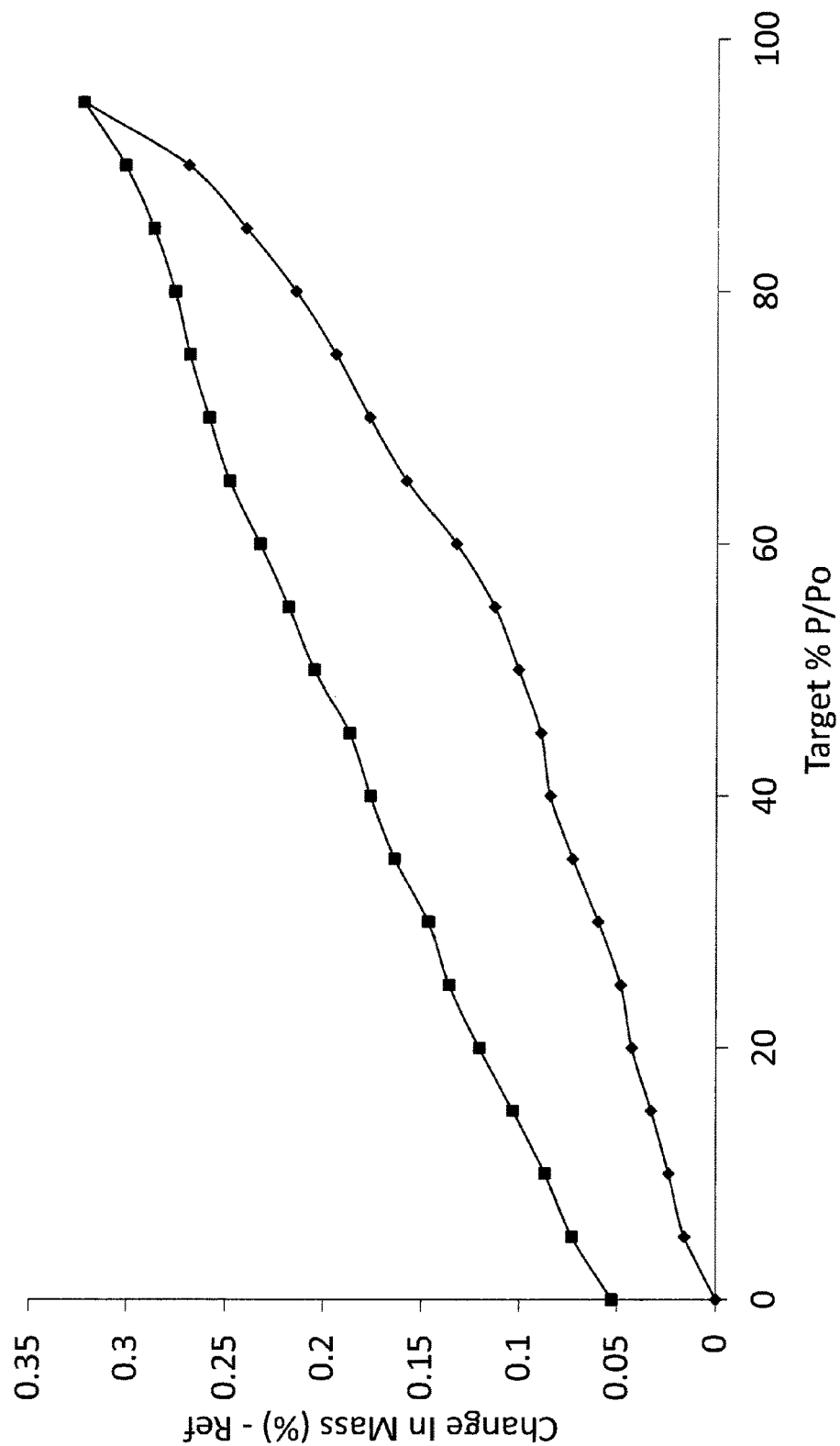

[Figure 49]
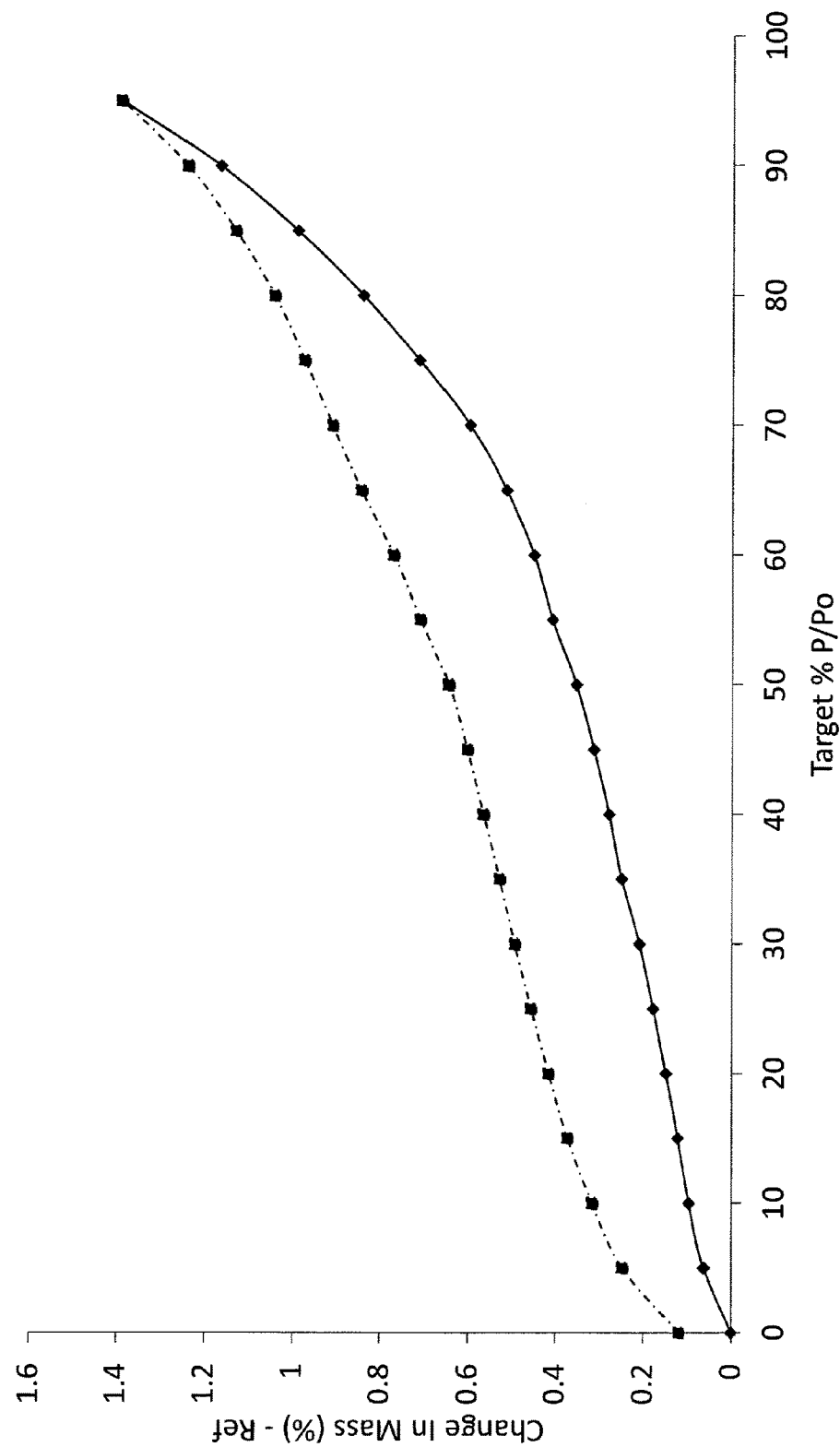

[Figure 50]
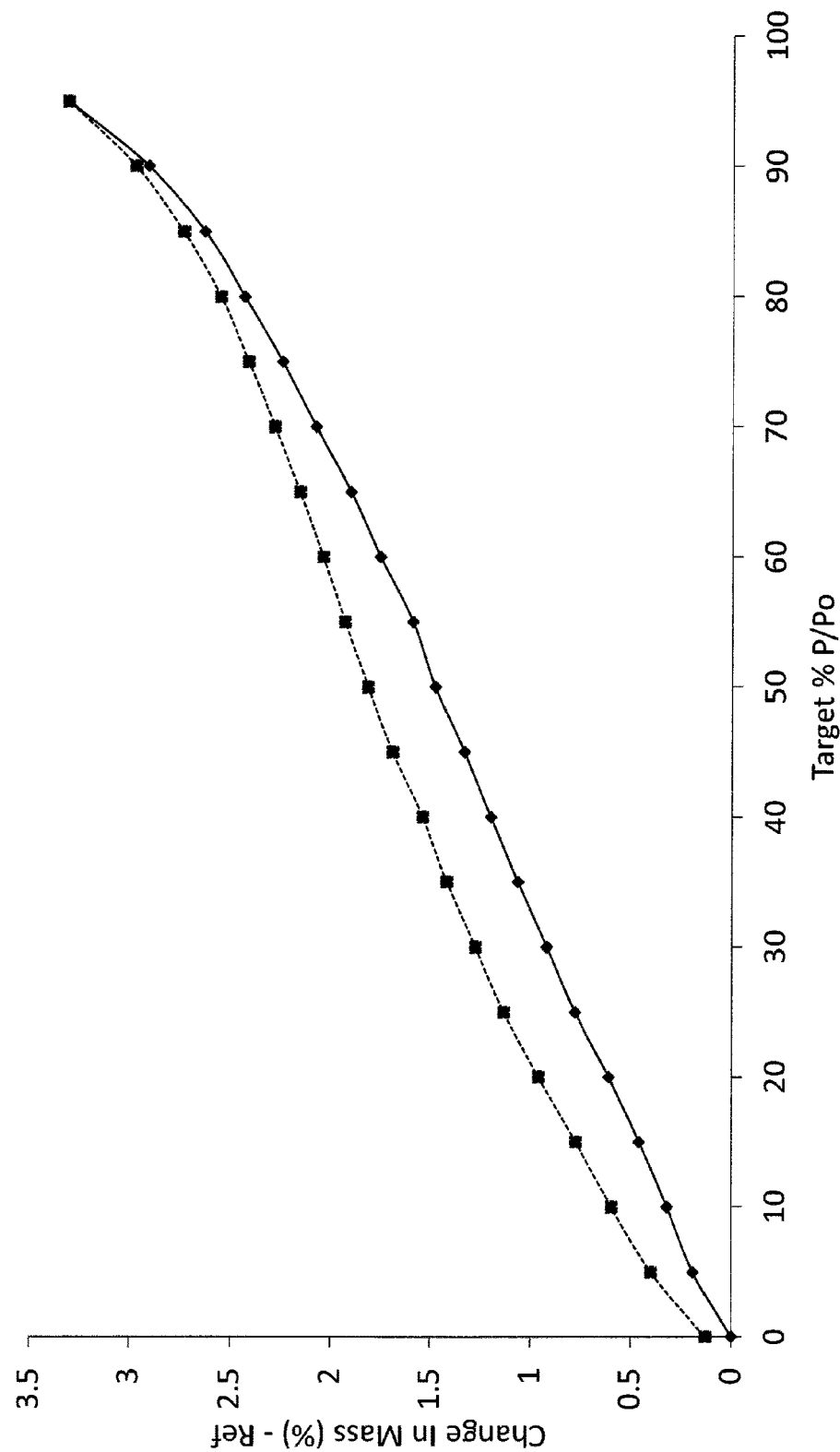

[Figure 51]
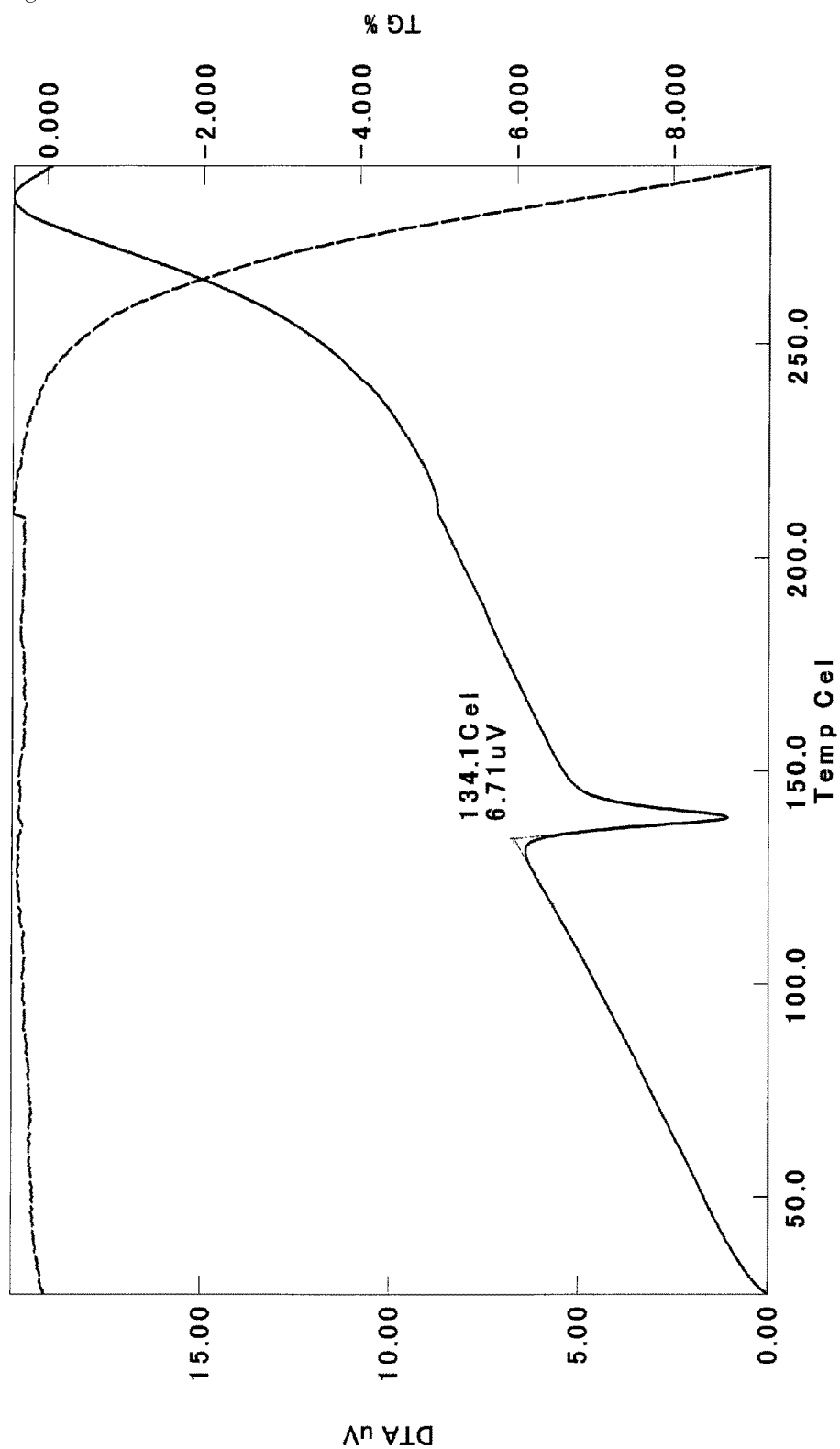

[Figure 52]
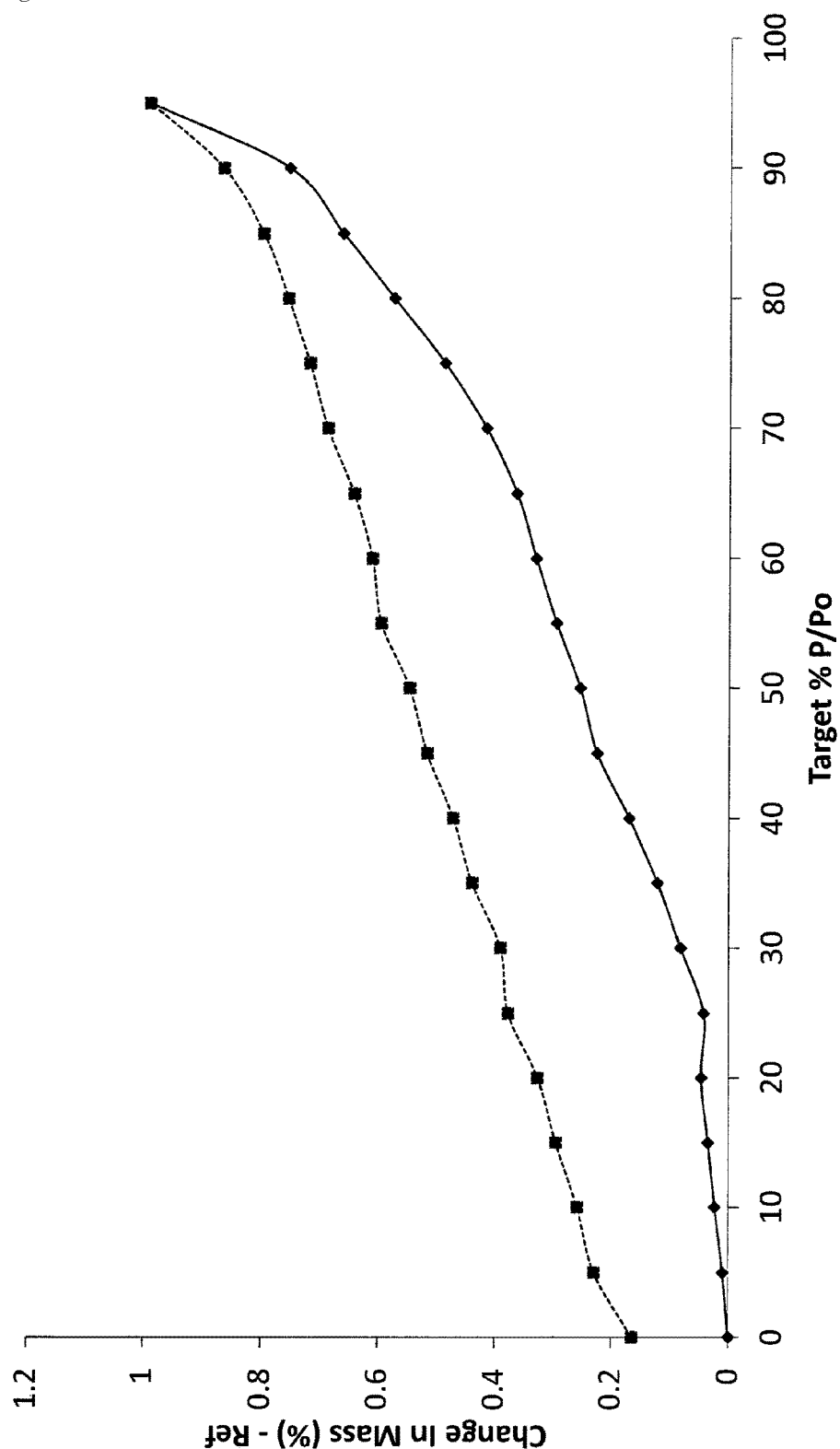

[Figure 53]
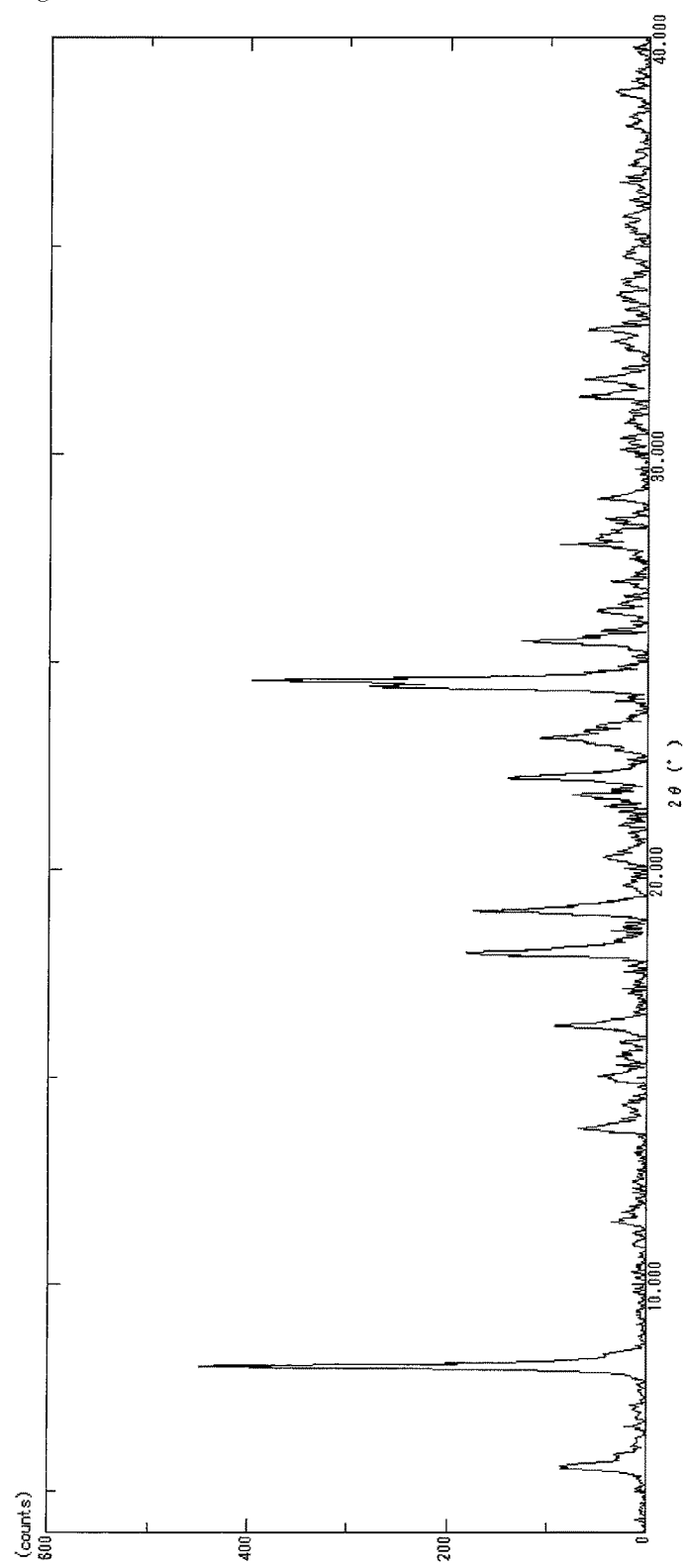

SALTS OF QUINAZOLINE DERIVATIVE OR CRYSTALS THEREOF, AND THE PROCESS FOR PRODUCING THEREOF

TECHNICAL FIELD

The present invention relates to an acid addition salt or crystals of the acid addition salt of a quinazoline derivative, and a pharmaceutical composition containing them. Moreover, the present invention relates to methods for producing the acid addition salt, the crystals of the acid addition salt, and the pharmaceutical composition containing them.

BACKGROUND ART

Tyrosine kinase is an enzyme which phosphorylates tyrosine residues in substrate proteins, and is known to play an important role in an intracellular signal transduction system concerning cellular differentiation and proliferation. Especially, it is known that a growth factor receptor tyrosine kinase (hereinafter receptor tyrosine kinase) such as HER2 (also called as ErbB2 or Neu) and EGF receptor etc. are considerably involved in cancer development, and their activities are increased in a variety of human cancers (Non-Patent Document 1, Non-Patent Document 2 and Non-Patent Document 3).

Also it is known that co-expression of EGF receptor and HER2 further promotes canceration by EGF receptor alone (Non-Patent Document 4) and a dual inhibitor that inhibits tyrosine kinase of both EGF receptor and HER2 is advantageous in having superior therapeutic effect in wider range of disease by synergistic effect of dual inhibition when compared with a EGF receptor or a HER2 selective inhibitor.

According to Patent Document 1, a quinazoline derivative represented by the following Formula:

[Chemical Formula 1]

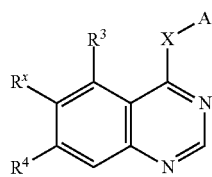

(I)

has dual inhibitory activity for EGF receptor and HER2, and is useful as a therapeutic and/or prophylactic agent for cancer. The following compound (VIII-102):

[Chemical Formula 2]

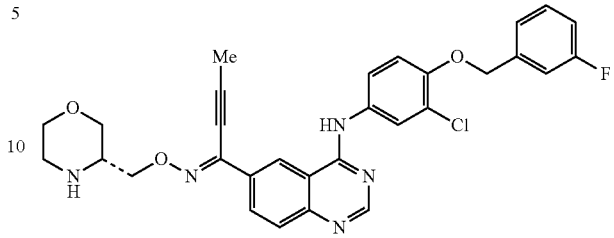

(VIII-102)

in a free base form is disclosed in an Example thereof, but neither an acid addition salt nor a solvate thereof is specifically disclosed. Also, crystals thereof are not specifically disclosed.

A method for producing a quinazoline derivative represented by Formula (VI'):

[Chemical Formula 3]

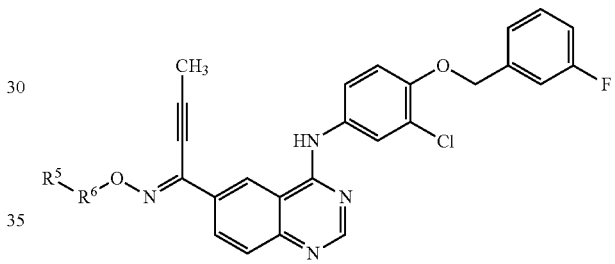

(VI')

is described in Patent Document 2. Also, the following compound (VI-15):

[Chemical Formula 4]

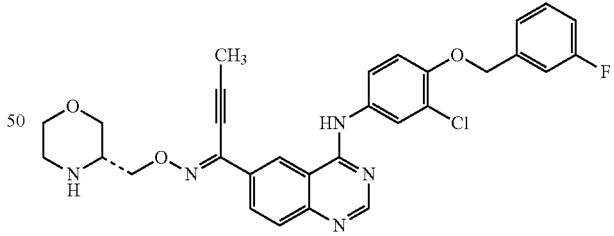

(VI-15)

in a free base form is disclosed in an Example thereof, but neither an acid addition salt nor a solvate thereof is specifically disclosed. Also, crystals thereof are not specifically disclosed.

Patent Documents 3 and 4 disclose hydrate crystals and anhydride crystals of Lapatinib ditosylate (ditosylate salt of N-{3-chloro-4-[(3-fluorobenzyl)oxy]phenyl}-6-[5-({[2-(methanesulphonyl)ethyl]amino}methyl)-2-furyl]-4-quinazolinamine) that has a dual inhibitory action for EGF receptor and HER2, and is represented by the following Formula.

[Chemical Formula 5]

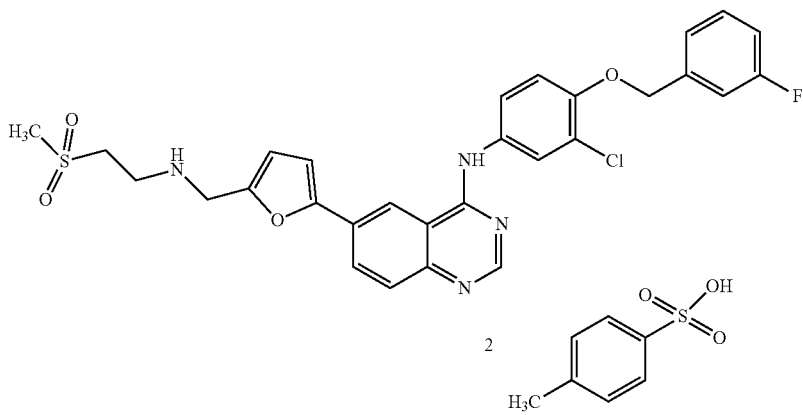

Also, Patent Document 5 discloses anhydride crystals of a free base of N-{3-chloro-4-[(3-fluorobenzyl)oxy]phenyl}-6-[5-({[2-(methanesulphonyl)ethyl]amino}methyl)-2-furyl]-4-quinazolinamine.

In drug delivery, a crystal form that has useful and excellent chemical and/or physical properties is desired.

PRIOR ART REFERENCES

Patent Document

[Patent Document 1] International Publication No. WO 2006/090717
[Patent Document 2] International Publication No. WO 2010/074150
[Patent Document 3] International Publication No. WO 2002/002552
[Patent Document 4] International Publication No. WO 2009/079541
[Patent Document 5] International Publication No. WO 2009/079547

Non-Patent Document

[Non-patent Document 1] Cancer Research (Cancer Res.), 1991, vol. 51, p. 4430-4435
[Non-patent Document 2] Cancer Research (Cancer Res.), 1992, vol. 52, p. 3636-3641
[Non-patent Document 3] Cancer Chemotherapy and Pharmacology (Cancer Chemother. Pharmacol.), 1993, vol. 32, p. 1-19
[Non-patent Document 4] Cell, 1989, vol. 58, p. 287-292

SUMMARY OF THE INVENTION

Problems to be Solved by the Invention

Active pharmaceutical ingredients may have substantially different physical properties according to the respective solid forms. Such differences in physical properties may influence, for example, a production method or an administration method for an active pharmaceutical ingredient or influence a pharmaceutical composition containing an active pharmaceutical ingredient. The present invention provides an acid addition salt or a solvate thereof of a compound represented by Formula (I) or their crystals more useful in a production method or an administration method for an active pharmaceutical ingredient or a pharmaceutical composition containing an active pharmaceutical ingredient than the other solid forms. Moreover, the present invention provides an intermediate useful for producing the acid addition salt, the solvate thereof, or their crystals.

Although the compound represented by Formula (I) is already disclosed, it is desired to establish a suitable solid form and a more preferable production method for using the compound as a pharmaceutical product or for industrially producing the compound as a pharmaceutical product.

Means for Solving the Problem

As a result of having conducted diligent research, the inventors have found that in hydrochloride of the compound represented by Formula (I), there are crystal forms of Form I, Form II, Form III, Form V, Form VI and Form VII of monohydrochloride and crystal form of ethanolate of monohydrochloride. Also, the inventors have found that there are crystal forms of mono-p-toluenesulfonate; monosulfate and monosulfate hydrate; monophosphate and monophosphate hydrate; and monofumarate of the compound represented by Formula (I). Furthermore, the inventors have found that crystal forms of Form I, Form V and Form VI of monohydrochloride as well as crystal form of mono-p-toluenesulfonate are more thermodynamically stable than other crystal forms.

Also, the inventors have found a compound represented by Formula (II), a pharmaceutically acceptable salt thereof, their solvates, or their crystals useful for producing hydrochloride or crystals of the hydrochloride, or mono-p-toluenesulfonate or crystals of the mono-p-toluenesulfonate of the compound represented by Formula (I) useful as an active pharmaceutical ingredient.

The present invention relates to the following items 1) to 36).

1) Hydrochloride of a compound represented by Formula (I):

[Chemical Formula 6]

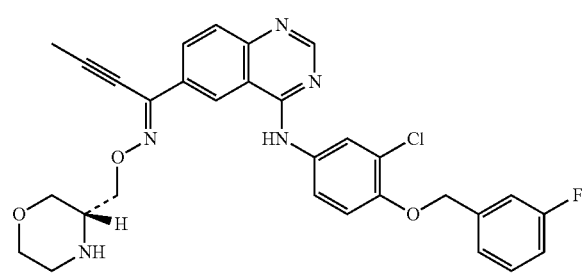

or a solvate thereof.

2) The hydrochloride or solvate thereof according to the above item 1), wherein the hydrochloride is monohydrochloride.

3) A crystal of hydrochloride of a compound represented by Formula (I).

[Chemical Formula 7]

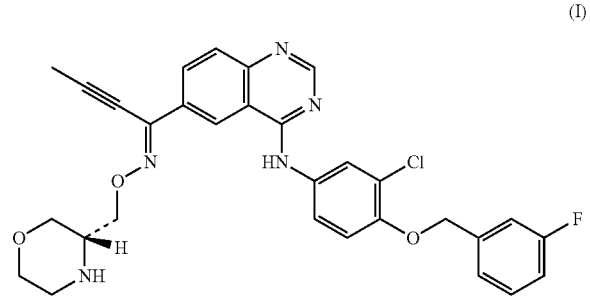 [SMILES: CC#C/C(=N\OC[C@H]1COCCN1)c1ccc2ncnc(Nc3ccc(OCc4cccc(F)c4)c(Cl)c3)c2c1]

4) The crystal according to the above item 3), wherein the hydrochloride is monohydrochloride.

5) The crystal according to the above item 4), which exhibits X-ray powder diffraction spectrum having peaks at diffraction angles 2θ: 8.0°±0.2°, 14.1°±0.2°, 20.6°±0.2°, 21.0°±0.2°, and 25.8°±0.2°.

6) The crystal according to the above item 4), which exhibits X-ray powder diffraction spectrum having peaks at diffraction angles 2θ: 6.8°±0.2°, 8.0°±0.2°, 14.1°±0.2°, 17.9°±0.2°, 18.5°±0.2°, 20.6°±0.2°, 21.0°±0.2°, 22.5°±0.2°, 25.8°±0.2°, and 28.4°±0.2°.

7) The crystal according to the above item 4), which exhibits X-ray powder diffraction spectrum having peaks at diffraction angles 2θ: 23.9°±0.2°, 25.9°±0.2°, 26.2°±0.2°, 26.7°±0.2°, and 28.4°±0.2°.

8) The crystal according to the above item 4), which exhibits X-ray powder diffraction spectrum having peaks at diffraction angles 2θ: 7.9°±0.2°, 9.7°±0.2°, 11.9°±0.2°, 15.8°±0.2°, 18.5°±0.2°, 23.9°±0.2°, 25.9°±0.2°, 26.2°±0.2°, 26.7°±0.2°, and 28.4°±0.2°.

9) The crystal according to the above item 4), which exhibits X-ray powder diffraction spectrum having peaks at diffraction angles 2θ: 5.4°±0.2°, 16.3°±0.2°, 21.6°±0.2°, 23.2°±0.2°, and 23.7°±0.2°.

10) The crystal according to the above item 4), which exhibits X-ray powder diffraction spectrum having peaks at diffraction angles 2θ: 5.4°±0.2°, 8.9°±0.2°, 11.7°±0.2°, 13.8°±0.2°, 16.3°±0.2°, 20.9°±0.2°, 21.6°±0.2°, 23.2°±0.2°, 23.7°±0.2°, and 26.6°±0.2°.

11) A pharmaceutical composition comprising the hydrochloride or solvate thereof according to the above item 1) or 2).

11') A pharmaceutical composition comprising the crystal according to any one of the above items 3) to 10).

12) The pharmaceutical composition according to the above item 11) for use in treatment and/or prophylaxis of cancer.

12') The pharmaceutical composition according to the above item 12), wherein the cancer is breast cancer.

12") The pharmaceutical composition according to the above item 11), having EGF receptor inhibitory activity and HER2 inhibitory activity.

13) A treatment and/or prophylactic agent for cancer, comprising the crystal according to any one of the above items 3) to 10).

14) A method for treating and/or preventing cancer, comprising administering a pharmaceutical composition comprising the crystal according to any one of the above items 3) to 10).

15) Use of the crystal according to any one of the above items 3) to 10) for producing a medicament for treatment and/or prophylaxis of cancer.

16) The crystal according to any one of the above items 3) to 10) for treatment and/or prophylaxis of cancer.

17) A pharmaceutical composition for oral administration comprising the crystal according to any one of the above items 3) to 10).

18) The pharmaceutical composition according to the above item 17), which is a tablet, powder, granule, capsule, pill, film, suspension, emulsion, elixir, syrup, lemonade, spirit, aromatic water, extract, decoction, or tincture.

19) The pharmaceutical composition according to the above item 18), which is a sugar-coated tablet, film-coated tablet, enteric-coated tablet, sustained-release tablet, troche tablet, sublingual tablet, buccal tablet, chewable tablet, orally disintegrating tablet, dry syrup, soft capsule, microcapsule, or sustained-release capsule.

20) A pharmaceutical composition for parenteral administration comprising the crystal according to any one of the above items 3) to 10).

21) The pharmaceutical composition according to the above item 20), for dermal, subcutaneous, intravenous, intraarterial, intramuscular, intraperitoneal, transmucosal, inhalation, transnasal, ophthalmic, inner ear, or vaginal administration.

22) The pharmaceutical composition according to the above item 20) or 21), which is an injection, infusion, eye drop, nose drop, ear drop, aerosol, inhalation, lotion, impregnation, liniment, mouthwash, enema, ointment, plaster, jelly, cream, patch, cataplasm, external powder, or suppository.

23) A pharmaceutical composition for a pediatric or geriatric patient comprising the crystal according to any one of the above items 3) to 10).

24) The crystal according to the above item 4), characterized by X-ray powder diffraction spectrum substantially in accordance with FIG. 1.

25) The crystal according to the above item 4), characterized by X-ray powder diffraction spectrum substantially in accordance with FIG. 2.

26) The crystal according to the above item 4), characterized by X-ray powder diffraction spectrum substantially in accordance with FIG. 3.

27) A compound represented by Formula (II):

[Chemical Formula 8]

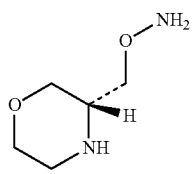

(II)

or a pharmaceutically acceptable salt, or solvate thereof.

28) The salt or solvate thereof according to the above item 27), wherein the salt is di-p-toluenesulfonate.

29) A crystal of di-p-toluenesulfonate of a compound represented by Formula (II).

[Chemical Formula 9]

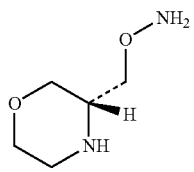

(II)

30) The crystal according to the above item 29), which exhibits X-ray powder diffraction spectrum having peaks at diffraction angles 2θ: 6.4°±0.2°, 7.3°±0.2°, 21.1°±0.2°, 24.7°±0.2°, and 25.3°±0.2°.

31) The crystal according to the above item 29), which exhibits X-ray powder diffraction spectrum having peaks at diffraction angles 2θ: 6.4°±0.2°, 7.3°±0.2°, 11.4°±0.2°, 15.2°±0.2°, 17.6°±0.2°, 20.1°±0.2°, 21.1°±0.2°, 21.7°±0.2°, 24.7°±0.2°, and 25.3°±0.2°.

32) A crystal of di-p-toluenesulfonate dihydrate of a compound represented by Formula (II).

[Chemical Formula 10]

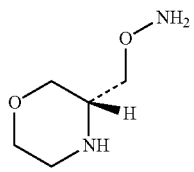

(II)

33) The crystal according to the above item 32), which exhibits X-ray powder diffraction spectrum having peaks at diffraction angles 2θ: 7.3°±0.2°, 17.0°±0.2°, 18.5°±0.2°, 22.6°±0.2°, and 24.0°±0.2°.

34) The crystal according to the above item 32), which exhibits X-ray powder diffraction spectrum having peaks at diffraction angles 2θ: 7.3°±0.2°, 17.0°±0.2°, 18.5°±0.2°, 19.7°±0.2°, 21.7°±0.2°, 22.6°±0.2°, 22.8°±0.2°, 24.0°±0.2°, 24.8°±0.2°, and 29.7°±0.2°.

35) The crystal according to the above item 29), characterized by X-ray powder diffraction spectrum substantially in accordance with FIG. 10.

36) The crystal according to the above item 32), characterized by X-ray powder diffraction spectrum substantially in accordance with FIG. 11.

Moreover, the present invention relates to the following items 1A) to 105A).

1A) A salt of a compound represented by Formula (I):

[Chemical Formula 11]

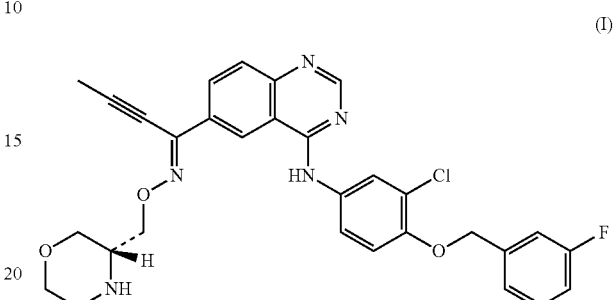

(I)

or a solvate thereof.

2A) The salt or solvate thereof according to the above item 1A), wherein the salt is hydrochloride.

3A) The salt or solvate thereof according to the above item 1A) or 2A), wherein the salt is monohydrochloride.

4A) A crystal of hydrochloride of a compound represented by Formula (I).

[Chemical Formula 12]

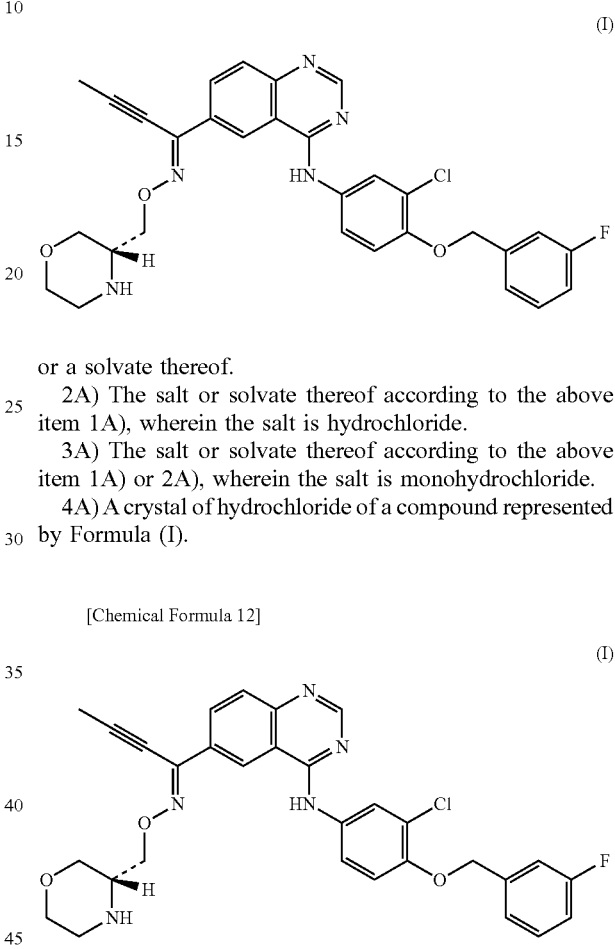

(I)

5A) The crystal according to the above item 4A), wherein the hydrochloride is monohydrochloride.

6A) The crystal according to the above item 5A), which exhibits X-ray powder diffraction spectrum having peaks at diffraction angles 2θ: 8.0°±0.2°, 14.1°±0.2°, 20.6°±0.2°, 21.0°±0.2°, and 25.8°±0.2°.

7A) The crystal according to the above item 5A), which exhibits X-ray powder diffraction spectrum having peaks at diffraction angles 2θ: 6.8°±0.2°, 8.0°±0.2°, 14.1°±0.2°, 17.9°±0.2°, 18.5°±0.2°, 20.6°±0.2°, 21.0°±0.2°, 22.5°±0.2°, 25.8°±0.2°, and 28.4°±0.2°.

8A) The crystal according to the above item 5A), which exhibits X-ray powder diffraction spectrum having peaks at diffraction angles 2θ: 23.9°±0.2°, 25.9°±0.2°, 26.2°±0.2°, 26.7°±0.2°, and 28.4°±0.2°.

9A) The crystal according to the above item 5A), which exhibits X-ray powder diffraction spectrum having peaks at diffraction angles 2θ: 7.9°±0.2°, 9.7°±0.2°, 11.9°±0.2°, 15.8°±0.2°, 18.5°±0.2°, 23.9°±0.2°, 25.9°±0.2°, 26.2°±0.2°, 26.7°±0.2°, and 28.4°±0.2°.

10A) The crystal according to the above item 5A), which exhibits X-ray powder diffraction spectrum having peaks at diffraction angles 2θ: 5.4°±0.2°, 16.3°±0.2°, 21.6°±0.2°, 23.2°±0.2°, and 23.7°±0.2°.

11A) The crystal according to the above item 5A), which exhibits X-ray powder diffraction spectrum having peaks at diffraction angles 2θ: 5.4°±0.2°, 8.9°±0.2°, 11.7°±0.2°, 13.8°±0.2°, 16.3°±0.2°, 20.9°±0.2°, 21.6°±0.2°, 23.2°±0.2°, 23.7°±0.2°, and 26.6°±0.2°.

12A) A pharmaceutical composition comprising the hydrochloride or solvate thereof according to the above item 2A) or 3A).

13A) A pharmaceutical composition comprising the crystal according to any one of the above items 4A) to 11A).

13A') A pharmaceutical composition comprising the crystal according to any one of the above items 4A) to 11A), wherein an amount of an impurity is 2% by weight or less.

13A") The pharmaceutical composition according to the above item 13A'), wherein the impurity is an E isomer of the compound represented by Formula (I).

14A) The salt or solvate thereof according to the above item 1A), wherein the salt is p-toluenesulfonate.

15A) The salt or solvate thereof according to the above item 1A) or 14A), wherein the salt is mono-p-toluenesulfonate.

16A) A crystal of p-toluenesulfonate of a compound represented by Formula (I).

[Chemical Formula 13]

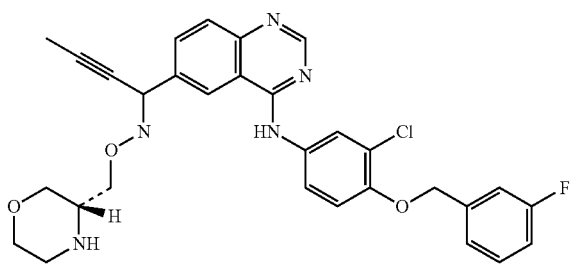

(I)

17A) The crystal according to the above item 16A), wherein the p-toluenesulfonate is mono-p-toluenesulfonate.

18A) The crystal according to the above item 17A), which exhibits X-ray powder diffraction spectrum having peaks at diffraction angles 2θ: 13.7°±0.2°, 15.7°±0.2°, 20.0°±0.2°, 22.7°±0.2°, and 25.3°±0.2°.

19A) The crystal according to the above item 17A), which exhibits X-ray powder diffraction spectrum having peaks at diffraction angles 2θ: 6.1°±0.2°, 6.4°±0.2°, 10.8°±0.2°, 13.7°±0.2°, 15.7°±0.2°, 16.3°±0.2°, 20.0°±0.2°, 22.7°±0.2°, 24.6°±0.2°, and 25.3°±0.2°.

20A) A pharmaceutical composition comprising the p-toluenesulfonate or solvate thereof according to the above item 14A) or 15A).

21A) A pharmaceutical composition comprising the crystal according to any one of the above items 16A) to 19A).

21A') A pharmaceutical composition comprising the crystal according to any one of the above items 16A) to 19A), wherein an amount of an impurity is 2% by weight or less.

21A") The pharmaceutical composition according to the above item 21A'), wherein the impurity is an E isomer of the compound represented by Formula (I).

22A) The pharmaceutical composition according to the above item 12A) or 20A) for use in treatment and/or prophylaxis of cancer.

23A) The pharmaceutical composition according to the above item 13A) or 21A) for use in treatment and/or prophylaxis of cancer.

24A) The pharmaceutical composition according to the above item 22A), wherein the cancer is breast cancer.

25A) The pharmaceutical composition according to the above item 23A), wherein the cancer is breast cancer.

26A) The pharmaceutical composition according to the above item 12A) or 20A), having EGF receptor inhibitory activity and HER2 inhibitory activity.

27A) The pharmaceutical composition according to the above item 13A) or 21A), having EGF receptor inhibitory activity and HER2 inhibitory activity.

28A) A treatment and/or prophylactic agent for cancer, comprising the crystal according to any one of the above items 4A) to 11A).

29A) A treatment and/or prophylactic agent for cancer, comprising the crystal according to any one of the above items 16A) to 19A).

30A) A method for treating and/or preventing cancer, comprising administering a pharmaceutical composition comprising the crystal according to any one of the above items 4A) to 11A).

30A') The method for treating and/or preventing cancer according to the above item 30A), wherein the cancer is breast cancer.

31A) A method for treating and/or preventing cancer, comprising administering a pharmaceutical composition comprising the crystal according to any one of the above items 16A) to 19A).

31A') The method for treating and/or preventing cancer according to the above item 31A), wherein the cancer is breast cancer.

32A) Use of the crystal according to any one of the above items 4A) to 11A) for producing a medicament for treatment and/or prophylaxis of cancer.

32A') The use of the crystal according to the above item 32A), wherein the cancer is breast cancer.

33A) Use of the crystal according to any one of the above items 16A) to 19A) for producing a medicament for treatment and/or prophylaxis of cancer.

33A') The use of crystal according to the above item 33A), wherein the cancer is breast cancer.

34A) The crystal according to any one of the above items 4A) to 11A) for treatment and/or prophylaxis of cancer.

34A') The crystal according to the above item 34A), wherein the cancer is breast cancer.

35A) The crystal according to any one of the above items 16A) to 19A) for treatment and/or prophylaxis of cancer.

35A') The crystal according to the above item 35A), wherein the cancer is breast cancer.

36A) A pharmaceutical composition for oral administration comprising the crystal according to any one of the above items 4A) to 11A).

37A) A pharmaceutical composition for oral administration comprising the crystal according to any one of the above items 16A) to 19A).

38A) The pharmaceutical composition according to the above item 36A), which is a tablet, powder, granule, capsule, pill, film, suspension, emulsion, elixir, syrup, lemonade, spirit, aromatic water, extract, decoction, or tincture.

39A) The pharmaceutical composition according to the above item 37A), which is a tablet, powder, granule, capsule, pill, film, suspension, emulsion, elixir, syrup, lemonade, spirit, aromatic water, extract, decoction, or tincture.

40A) The pharmaceutical composition according to the above item 38A), which is a sugar-coated tablet, film-coated tablet, enteric-coated tablet, sustained-release tablet, troche tablet, sublingual tablet, buccal tablet, chewable tablet, orally disintegrating tablet, dry syrup, soft capsule, microcapsule, or sustained-release capsule.

41A) The pharmaceutical composition according to the above item 39A), which is a sugar-coated tablet, film-coated tablet, enteric-coated tablet, sustained-release tablet, troche tablet, sublingual tablet, buccal tablet, chewable tablet, orally disintegrating tablet, dry syrup, soft capsule, microcapsule, or sustained-release capsule.

42A) A pharmaceutical composition for parenteral administration comprising the crystal according to any one of the above items 4A) to 11A).

43A) A pharmaceutical composition for parenteral administration comprising the crystal according to any one of the above items 16A) to 19A).

44A) The pharmaceutical composition according to the above item 42A), for dermal, subcutaneous, intravenous, intraarterial, intramuscular, intraperitoneal, transmucosal, inhalation, transnasal, ophthalmic, inner ear, or vaginal administration.

45A) The pharmaceutical composition according to the above item 43A), for dermal, subcutaneous, intravenous, intraarterial, intramuscular, intraperitoneal, transmucosal, inhalation, transnasal, ophthalmic, inner ear, or vaginal administration.

46A) The pharmaceutical composition according to the above item 42A) or 44A), which is an injection, infusion, eye drop, nose drop, ear drop, aerosol, inhalation, lotion, impregnation, liniment, mouthwash, enema, ointment, plaster, jelly, cream, patch, cataplasm, external powder, or suppository.

47A) The pharmaceutical composition according to the above item 43A) or 45A), which is an injection, infusion, eye drop, nose drop, ear drop, aerosol, inhalation, lotion, impregnation, liniment, mouthwash, enema, ointment, plaster, jelly, cream, patch, cataplasm, external powder, or suppository.

48A) A pharmaceutical composition for parenteral administration comprising the crystal according to any one of the above items 4A) to 11A).

49A) A pharmaceutical composition for parenteral administration comprising the crystal according to any one of the above items 16A) to 19A).

50A) A compound represented by Formula (II):

[Chemical Formula 14]

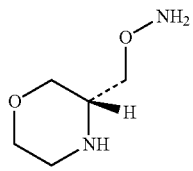

(II)

or a pharmaceutically acceptable salt, or solvate thereof.

51A) The salt or solvate according to the above item 50A), wherein the salt is di-p-toluenesulfonate.

52A) A crystal of di-p-toluenesulfonate of a compound represented by Formula (II).

[Chemical Formula 15]

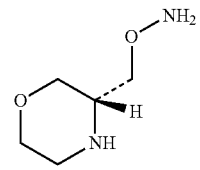

(II)

53A) The crystal according to the above item 52A), which exhibits X-ray powder diffraction spectrum having peaks at diffraction angles 2θ: 6.4°±0.2°, 7.3°±0.2°, 21.1°±0.2°, 24.7°±0.2°, and 25.3°±0.2°.

54A) The crystal according to the above item 52A), which exhibits X-ray powder diffraction spectrum having peaks at diffraction angles 2θ: 6.4°±0.2°, 7.3°±0.2°, 11.4°±0.2°, 15.2°±0.2°, 17.6°±0.2°, 20.1°±0.2°, 21.1°±0.2°, 21.7°±0.2°, 24.7°±0.2°, and 25.3°±0.2°.

55A) A crystal of di-p-toluenesulfonate dihydrate of a compound represented by Formula (II).

[Chemical Formula 16]

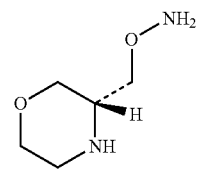

(II)

56A) The crystal according to the above item 55A), which exhibits X-ray powder diffraction spectrum having peaks at diffraction angles 2θ: 7.3°±0.2°, 17.0°±0.2°, 18.5°±0.2°, 22.6°±0.2°, and 24.0°±0.2°.

57A) The crystal according to the above item 55A), which exhibits X-ray powder diffraction spectrum having peaks at diffraction angles 2θ: 7.3°±0.2°, 17.0°±0.2°, 18.5°±0.2°, 19.7°±0.2°, 21.7°±0.2°, 22.6°±0.2°, 22.8°±0.2°, 24.0°±0.2°, 24.8°±0.2°, and 29.7°±0.2°.

58A) The crystal according to the above item 5A), characterized by X-ray powder diffraction spectrum substantially in accordance with FIG. 1.

59A) The crystal according to the above item 5A), characterized by X-ray powder diffraction spectrum substantially in accordance with FIG. 2.

60A) The crystal according to the above item 5A), characterized by X-ray powder diffraction spectrum substantially in accordance with FIG. 3.

61A) The crystal according to the above item 5A), which exhibits X-ray powder diffraction spectrum having peaks at diffraction angles 2θ: 11.3°±0.2°, 17.1°±0.2°, 25.5°±0.2°, 25.8°±0.2°, and 26.4°±0.2°.

62A) The crystal according to the above item 5A), which exhibits X-ray powder diffraction spectrum having peaks at diffraction angles 2θ: 5.3°±0.2°, 11.3°±0.2°, 17.1°±0.2°, 18.8°±0.2°, 21.7°±0.2°, 23.2°±0.2°, 25.5°±0.2°, 25.8°±0.2°, 26.4°±0.2°, and 29.4°±0.2°.

63A) The crystal according to the above item 5A), characterized by X-ray powder diffraction spectrum substantially in accordance with FIG. 12.

64A) The crystal according to the above item 5A), which exhibits X-ray powder diffraction spectrum having peaks at diffraction angles 2θ: 5.1°±0.2°, 9.9°±0.2°, 15.3°±0.2°, 21.4°±0.2°, and 23.3°±0.2°.

65A) The crystal according to the above item 5A), which exhibits X-ray powder diffraction spectrum having peaks at diffraction angles 2θ: 5.1°±0.2°, 5.6°±0.2°, 9.2°±0.2°, 9.9°±0.2°, 14.4°±0.2°, 15.3°±0.2°, 21.4°±0.2°, 22.6°±0.2°, and 23.3°±0.2°.

66A) The crystal according to the above item 5A), characterized by X-ray powder diffraction spectrum substantially in accordance with FIG. 13.

67A) The crystal according to the above item 5A), which exhibits X-ray powder diffraction spectrum having peaks at diffraction angles 2θ: 7.0°±0.2°, 12.3°±0.2°, 16.0°±0.2°, 19.1°±0.2°, and 21.2°±0.2°.

68A) The crystal according to the above item 5A), which exhibits X-ray powder diffraction spectrum having peaks at diffraction angles 2θ: 5.7°±0.2°, 7.0°±0.2°, 11.4°±0.2°, 12.3°±0.2°, 16.0°±0.2°, 17.3°±0.2°, 19.1°±0.2°, 21.2°±0.2°, and 23.0°±0.2°.

69A) The crystal according to the above item 5A), characterized by X-ray powder diffraction spectrum substantially in accordance with FIG. 14.

70A) A crystal of monohydrochloride ethanolate of a compound represented by Formula (I).

71A) The crystal according to the above item 70A), which exhibits X-ray powder diffraction spectrum having peaks at diffraction angles 2θ: 8.3°±0.2°, 8.9°±0.2°, 12.9°±0.2°, 13.7°±0.2°, and 14.7°±0.2°.

72A) The crystal according to the above item 70A), which exhibits X-ray powder diffraction spectrum having peaks at diffraction angles 2θ: 7.6°±0.2°, 8.3°±0.2°, 8.9°±0.2°, 12.9°±0.2°, 13.7°±0.2°, 14.7°±0.2°, 21.1°±0.2°, 21.5°±0.2°, 23.0°±0.2°, and 23.7°±0.2°.

73A) The crystal according to the above item 70A), characterized by X-ray powder diffraction spectrum substantially in accordance with FIG. 15.

82A) The crystal according to the above item 17A), characterized by X-ray powder diffraction spectrum substantially in accordance with FIG. 18.

83A) A crystal of monosulfate of a compound represented by Formula (I).

84A) The crystal according to the above item 83A), which exhibits X-ray powder diffraction spectrum having peaks at diffraction angles 2θ: 6.2°±0.2°, 14.0°±0.2°, 14.5°±0.2°, 16.8°±0.2°, and 22.9°±0.2°.

85A) The crystal according to the above item 83A), which exhibits X-ray powder diffraction spectrum having peaks at diffraction angles 2θ: 6.2°±0.2°, 12.1°±0.2°, 14.0°±0.2°, 14.5°±0.2°, 15.9°±0.2°, 16.2°±0.2°, 16.8°±0.2°, 21.0°±0.2°, 22.9°±0.2°, and 26.9°±0.2°.

86A) The crystal according to the above item 83A), characterized by X-ray powder diffraction spectrum substantially in accordance with FIG. 19.

87A) A crystal of monosulfate monohydrate of a compound represented by Formula (I).

88A) The crystal according to the above item 87A), which exhibits X-ray powder diffraction spectrum having peaks at diffraction angles 2θ: 5.0°±0.2°, 9.9°±0.2°, 13.8°±0.2°, 14.7°±0.2°, and 17.0°±0.2°.

89A) The crystal according to the above item 87A), which exhibits X-ray powder diffraction spectrum having peaks at diffraction angles 2θ: 5.0°±0.2°, 7.4°±0.2°, 9.9°±0.2°, 10.1°±0.2°, 13.8°±0.2°, 14.7°±0.2°, 17.0°±0.2°, and 21.4°±0.2°.

90A) The crystal according to the above item 87A), characterized by X-ray powder diffraction spectrum substantially in accordance with FIG. 20.

91A) A crystal of monophosphate of a compound represented by Formula (I).

92A) The crystal according to the above item 91A), which exhibits X-ray powder diffraction spectrum having peaks at diffraction angles 2θ: 5.1°±0.2°, 6.2°±0.2°, 6.7°±0.2°, 9.8°±0.2°, and 12.3°±0.2°.

93A) The crystal according to the above item 91A), which exhibits X-ray powder diffraction spectrum having peaks at diffraction angles 2θ: 5.1°±0.2°, 6.2°±0.2°, 6.7°±0.2°, 9.8°±0.2°, 12.3°±0.2°, 13.3°±0.2°, 16.6°±0.2°, and 21.1°±0.2°.

94A) The crystal according to the above item 91A), characterized by X-ray powder diffraction spectrum substantially in accordance with FIG. 21.

95A) A crystal of monophosphate dihydrate of a compound represented by Formula (I).

96A) The crystal according to the above item 95A), which exhibits X-ray powder diffraction spectrum having peaks at diffraction angles 2θ: 5.1°±0.2°, 6.5°±0.2°, 9.6°±0.2°, 12.9°±0.2°, and 18.6°±0.2°.

97A) The crystal according to the above item 95A), which exhibits X-ray powder diffraction spectrum having peaks at diffraction angles 2θ: 5.1°±0.2°, 6.5°±0.2°, 9.6°±0.2°, 10.0°±0.2°, 11.9°±0.2°, 12.2°±0.2°, 12.9°±0.2°, 16.9°±0.2°, and 18.6°±0.2°.

98A) The crystal according to the above item 95A), characterized by X-ray powder diffraction spectrum substantially in accordance with FIG. 22.

99A) A crystal of monofumarate of a compound represented by Formula (I).

100A) The crystal according to the above item 99A), which exhibits X-ray powder diffraction spectrum having peaks at diffraction angles 2θ: 8.0°±0.2°, 9.1°±0.2°, 16.1°±0.2°, 19.5°±0.2°, and 19.9°±0.2°.

101A) The crystal according to the above item 99A), which exhibits X-ray powder diffraction spectrum having peaks at diffraction angles 2θ: 5.4°±0.2°, 6.0°±0.2°, 8.0°±0.2°, 9.1°±0.2°, 10.0°±0.2°, 12.3°±0.2°, 14.8°±0.2°, 16.1°±0.2°, 19.5°±0.2°, and 19.9°±0.2°.

102A) The crystal according to the above item 99A), characterized by X-ray powder diffraction spectrum substantially in accordance with FIG. 23.

103A) The crystal according to the above item 99A), which exhibits X-ray powder diffraction spectrum having peaks at diffraction angles 2θ: 5.4°±0.2°, 9.1°±0.2°, 13.3°±0.2°, 13.7°±0.2°, and 18.1°±0.2°.

104A) The crystal according to the above item 99A), which exhibits X-ray powder diffraction spectrum having peaks at diffraction angles 2θ: 5.4°±0.2°, 8.0°±0.2°, 9.1°±0.2°, 13.3°±0.2°, 13.7°±0.2°, 16.4°±0.2°, 17.1°±0.2°, 18.1°±0.2°, 19.9°±0.2°, and 21.8°±0.2°.

105A) The crystal according to the above item 99A), characterized by X-ray powder diffraction spectrum substantially in accordance with FIG. 24.

Effect of the Invention

The present invention provides an acid addition salt of a compound represented by Formula (I) and crystals thereof. The crystals have good stability and solubility, and can be used as an active ingredient for producing a pharmaceutical product.

Also, a pharmaceutical composition containing the crystals of an acid addition salt of a compound represented by Formula (I) of the present invention can be used as an anticancer agent.

Moreover, the present invention provides a compound represented by Formula (II), a pharmaceutically acceptable salt thereof, their solvates, or their crystals. The compound and the like are useful when producing an acid addition salt of a compound represented by Formula (I) and crystals thereof.

A free base of an acid addition salt or a solvate thereof of the compound represented by Formula (I) of the present invention is a compound having usefulness as a medicament. Here, usefulness as a medicament includes good solubility, good metabolical stability, unlikeliness to induce drug-metabolizing enzymes, unlikeliness to inhibit drug-metabolizing enzymes that metabolize other pharmaceutical agents, being a highly orally absorbable compound, unlikeliness to inhibit hERG, low clearance, and/or a sufficiently long half-life to exert medicinal effects.

The acid addition salt or solvate thereof of the compound represented by Formula (I) of the present invention or crystals thereof have usefulness as a medicament. Here, usefulness as a medicament include high solubility in water, high heat stability, low hygroscopicity, high photostability, high solution stability, high storage stability, high coloration stability, high light exposure stability, high stability when light is blocked, a low specific volume, unlikeliness to be electrostatically charged, high condensability, good flowability, high crystallinity, high filtration/centrifugation applicability, high solvent removability, compatibility with industrially advantageous solvents, and high compression-formability into tablets.

Also, the compound in solid form can substantially influence physical properties of the compound, including (1) packaging properties such as molar volume, density, and hygroscopicity, (2) thermodynamic properties such as melting temperature, vapor pressure, and solubility, (3) kinetic properties such as dissolution rate and stability (such as stability against humidity and stability in surroundings under storage conditions), (4) surface properties such as surface area, wettability, interfacial tension, and shape, (5) mechanical properties such as hardness, tensile strength, moldability, handleability, flowability (flow), and blendability (blend), or (6) filterability. Selection and control of a solid form are important particularly for compounds that serve as drugs. Careful selection and control of a solid form can reduce problems involved in production, formulation, or administration of the compound.

BRIEF DESCRIPTION OF DRAWINGS

FIG. 1 shows X-ray powder diffraction pattern of monohydrochloride crystal form I (Form I) of the compound represented by Formula (I). The horizontal axis represents 2θ(°), and the vertical axis represents intensity (Count).

FIG. 2 shows X-ray powder diffraction pattern of monohydrochloride crystal form V (Form V) of the compound represented by Formula (I). The horizontal axis represents 2θ(°), and the vertical axis represents intensity (Count).

FIG. 3 shows X-ray powder diffraction pattern of monohydrochloride crystal form VI (Form VI) of the compound represented by Formula (I). The horizontal axis represents 2θ(°), and the vertical axis represents intensity (Count).

FIG. 4 shows TG/DTA analysis result of monohydrochloride crystal form I (Form I) of the compound represented by Formula (I).

FIG. 5 shows TG/DTA analysis result of monohydrochloride crystal form V (Form V) of the compound represented by Formula (I).

FIG. 6 shows TG/DTA analysis result of monohydrochloride crystal form VI (Form VI) of the compound represented by Formula (I).

FIG. 7 shows DSC analysis result of monohydrochloride crystal form I (Form I) of the compound represented by Formula (I).

FIG. 8 shows DSC analysis result of monohydrochloride crystal form V (Form V) of the compound represented by Formula (I).

FIG. 9 shows DSC analysis result of monohydrochloride crystal form VI (Form VI) of the compound represented by Formula (I).

FIG. 10 shows X-ray powder diffraction pattern of di-p-toluenesulfonate crystal of the compound represented by Formula (II). The horizontal axis represents 2θ(°), and the vertical axis represents intensity (Count).

FIG. 11 shows X-ray powder diffraction pattern of di-p-toluenesulfonate dihydrate crystal of the compound represented by Formula (II). The horizontal axis represents 2θ(°), and the vertical axis represents intensity (Count).

FIG. 12 shows X-ray powder diffraction pattern of monohydrochloride crystal form II (Form II) of the compound represented by Formula (I). The horizontal axis represents 2θ(°), and the vertical axis represents intensity (Count).

FIG. 13 shows X-ray powder diffraction pattern of monohydrochloride crystal form III (Form III) of the compound represented by Formula (I). The horizontal axis represents 2θ(°), and the vertical axis represents intensity (Count).

FIG. 14 shows X-ray powder diffraction pattern of monohydrochloride crystal form VII (Form VII) of the compound represented by Formula (I). The horizontal axis represents 2θ(°), and the vertical axis represents intensity (Count).

FIG. 15 shows X-ray powder diffraction pattern of monohydrochloride ethanolate crystal of the compound represented by Formula (I). The horizontal axis represents 2θ(°), and the vertical axis represents intensity (Count).

FIG. 16 shows X-ray powder diffraction pattern of free base monohydrate crystal of the compound represented by Formula (I). The horizontal axis represents 2θ(°), and the vertical axis represents intensity (Count).

FIG. 17 shows X-ray powder diffraction pattern of free base trihydrate crystal of the compound represented by Formula (I). The horizontal axis represents 2θ(°), and the vertical axis represents intensity (Count).

FIG. 18 shows X-ray powder diffraction pattern of mono-p-toluenesulfonate crystal form I (Form I) of the compound represented by Formula (I). The horizontal axis represents 2θ(°), and the vertical axis represents intensity (Count).

FIG. 19 shows X-ray powder diffraction pattern of monosulfate crystal of the compound represented by Formula (I). The horizontal axis represents 2θ(°), and the vertical axis represents intensity (Count).

FIG. 20 shows X-ray powder diffraction pattern of monosulfate monohydrate crystal of the compound represented by Formula (I). The horizontal axis represents 2θ(°), and the vertical axis represents intensity (Count).

FIG. 21 shows X-ray powder diffraction pattern of monophosphate crystal of the compound represented by Formula (I). The horizontal axis represents 2θ(°), and the vertical axis represents intensity (Count).

FIG. 22 shows X-ray powder diffraction pattern of monophosphate dihydrate crystal form I (Form I) of the compound represented by Formula (I). The horizontal axis represents 2θ(°), and the vertical axis represents intensity (Count).

FIG. 23 shows X-ray powder diffraction pattern of monofumarate crystal form I (Form I) of the compound represented by Formula (I). The horizontal axis represents 2θ(°), and the vertical axis represents intensity (Count).

FIG. 24 shows X-ray powder diffraction pattern of monofumarate crystal form II (Form II) of the compound represented by Formula (I). The horizontal axis represents 2θ(°), and the vertical axis represents intensity (Count).

FIG. 25 shows TG/DTA analysis result of monohydrochloride crystal form II (Form II) of the compound represented by Formula (I).

FIG. 26 shows TG/DTA analysis result of monohydrochloride crystal form III (Form III) of the compound represented by Formula (I).

FIG. 27 shows TG/DTA analysis result of monohydrochloride crystal form VII (Form VII) of the compound represented by Formula (I).

FIG. 28 shows TG/DTA analysis result of monohydrochloride ethanolate crystal of the compound represented by Formula (I).

FIG. 29 shows TG/DTA analysis result of free base monohydrate crystal of the compound represented by Formula (I).

FIG. 30 shows TG/DTA analysis result of free base trihydrate crystal of the compound represented by Formula (I).

FIG. 31 shows TG/DTA analysis result of mono-p-toluenesulfonate crystal form I (Form I) of the compound represented by Formula (I).

FIG. 32 shows TG/DTA analysis result of monosulfate crystal of the compound represented by Formula (I).

FIG. 33 shows TG/DTA analysis result of monosulfate monohydrate crystal of the compound represented by Formula (I).

FIG. 34 shows TG/DTA analysis result of monophosphate crystal of the compound represented by Formula (I).

FIG. 35 shows TG/DTA analysis result of monophosphate dihydrate crystal form I (Form I) of the compound represented by Formula (I).

FIG. 36 shows TG/DTA analysis result of monofumarate crystal form I (Form I) of the compound represented by Formula (I).

FIG. 37 shows TG/DTA analysis result of monofumarate crystal form II (Form II) of the compound represented by Formula (I).

FIG. 38 shows X-ray powder diffraction pattern of dihydrochloride crystal of the compound represented by Formula (I). The horizontal axis represents 2θ(°), and the vertical axis represents intensity (Count).

FIG. 39 shows X-ray powder diffraction pattern of mono-p-toluenesulfonate crystal form II (Form II) of the compound represented by Formula (I). The horizontal axis represents 2θ(°), and the vertical axis represents intensity (Count).

FIG. 40 shows X-ray powder diffraction pattern of monobenzenesulfonate crystal of the compound represented by Formula (I). The horizontal axis represents 2θ(°), and the vertical axis represents intensity (Count).

FIG. 41 shows X-ray powder diffraction pattern of monophosphate dihydrate crystal form II (Form II) of the compound represented by Formula (I). The horizontal axis represents 2θ(°), and the vertical axis represents intensity (Count).

FIG. 42 shows X-ray powder diffraction pattern of monocitrate crystal of the compound represented by Formula (I). The horizontal axis represents 2θ(°), and the vertical axis represents intensity (Count).

FIG. 43 shows X-ray powder diffraction pattern of monotartrate crystal of the compound represented by Formula (I). The horizontal axis represents 2θ(°), and the vertical axis represents intensity (Count).

FIG. 44 shows X-ray powder diffraction pattern of free base crystal of the compound represented by Formula (I). The horizontal axis represents 2θ(°), and the vertical axis represents intensity (Count).

FIG. 45 shows moisture sorption and desorption isotherms of monohydrochloride crystal form I (Form I) of the compound represented by Formula (I). The vertical axis represents the ratio of increased mass to mass at 0% Target % $P/P_0$ [Change In Mass, Unit: %], and the horizontal axis represents relative humidity [Target % $P/P_0$, Unit: %]. The curve plotted with ♦ is a moisture sorption isotherm, and the curve plotted with ■ is a moisture desorption isotherm.

FIG. 46 shows moisture sorption and desorption isotherms of monohydrochloride crystal form V (Form V) of the compound represented by Formula (I). The vertical axis represents the ratio of increased mass to mass at 0% Target % $P/P_0$ [Change In Mass, Unit: %], and the horizontal axis represents relative humidity [Target % $P/P_0$, Unit: %]. The curve plotted with ♦ is a moisture sorption isotherm, and the curve plotted with ■ is a moisture desorption isotherm.

FIG. 47 shows moisture sorption and desorption isotherms of monohydrochloride crystal form VI (Form VI) of the compound represented by Formula (I). The vertical axis represents the ratio of increased mass to mass at 0% Target % $P/P_0$ [Change In Mass, Unit: %], and the horizontal axis represents relative humidity [Target % $P/P_0$, Unit: %]. The curve plotted with ♦ is a moisture sorption isotherm, and the curve plotted with ■ is a moisture desorption isotherm.

FIG. 48 shows moisture sorption and desorption isotherms of monohydrochloride crystal form II (Form II) of the compound represented by Formula (I). The vertical axis represents the ratio of increased mass to mass at 0% Target % $P/P_0$ [Change In Mass, Unit: %], and the horizontal axis represents relative humidity [Target % $P/P_0$, Unit: %]. The curve plotted with ♦ is a moisture sorption isotherm, and the curve plotted with ■ is a moisture desorption isotherm.

FIG. 49 shows moisture sorption and desorption isotherms of mono-p-toluenesulfonate crystal form I (Form I) of the compound represented by Formula (I). The vertical axis represents the ratio of increased mass to mass at 0% Target % $P/P_0$ [Change In Mass, Unit: %], and the horizontal axis represents relative humidity [Target % $P/P_0$, Unit: %]. The curve plotted with ♦ is a moisture sorption isotherm, and the curve plotted with ■ is a moisture desorption isotherm.

FIG. 50 shows moisture sorption and desorption isotherms of monosulfate crystal of the compound represented by Formula (I). The vertical axis represents the ratio of increased mass to mass at 0% Target % $P/P_0$ [Change In Mass, Unit: %], and the horizontal axis represents relative humidity [Target % $P/P_0$, Unit: %]. The curve plotted with ♦ is a moisture sorption isotherm, and the curve plotted with ■ is a moisture desorption isotherm.

FIG. 51 shows TG/DTA analysis result of free base crystal of the compound represented by Formula (I).

FIG. 52 shows moisture sorption and desorption isotherms of free base crystal of the compound represented by Formula (I). The vertical axis represents the ratio of increased mass to mass at 0% Target % $P/P_0$ [Change In Mass, Unit: %], and the horizontal axis represents relative humidity [Target % $P/P_0$, Unit: %]. The curve plotted with ♦ is a moisture sorption isotherm, and the curve plotted with ■ is a moisture desorption isotherm.

FIG. 53 shows X-ray powder diffraction pattern of dibenzenesulfonate of the compound represented by Formula (II). The horizontal axis represents 2θ(°), and the vertical axis represents intensity (Count).

MODE FOR CARRYING OUT THE INVENTION

Hereinafter, the present invention is described by providing embodiments. Throughout the specification, singular forms should be understood as including their plural forms unless indicated otherwise. Accordingly, singular articles (such as "a", "an", and "the" in the case of English) should be understood as including plural concepts unless indicated otherwise. Also, the terms used herein should be understood as being used in their meanings commonly used in the art unless indicated otherwise. Accordingly, unless defined otherwise, all technical terms and scientific terms as used herein have the same meanings as those commonly understood by people having ordinary skill in the art to which the present invention pertains. In the case of contradiction, the present specification (including definitions) controls.

The meanings of the terms used herein are explained below. A term is used to provide the same meaning no matter when it is used alone or used in combination with other terms.

The term of "consisting of" means having only components.

The term of "comprising" means not restricting with components and not excluding undescribed factors.

The "anticancer agent" and "therapeutic agent for cancer" as used herein encompass therapeutic agents for brain tumor (such as glioblastoma), urological cancer (such as bladder cancer and renal cancer), genital cancer (such as prostate cancer, ovarian cancer, and uterine cancer), lymphatic tumor, gastrointestinal cancer (such as stomach cancer, esophageal cancer, large intestine cancer, and colon cancer), throat cancer, lung cancer (such as lung adenocarcinoma, small cell lung cancer, non-small cell lung cancer), pancreatic cancer, breast cancer, head and neck cancer, and thyroid cancer. In particular, the anticancer agent and the therapeutic agent for cancer are preferably used as therapeutic agents for breast cancer, brain tumor, bladder cancer, kidney cancer, prostate cancer, ovarian cancer, uterine cancer, lung cancer, pancreatic cancer, and head and neck cancer.

The present invention encompasses a method for treating or preventing cancer in a mammal in need of treating or preventing cancer, and the method comprising of administering to the mammal a therapeutically effective amount of crystals of an acid addition salt of the compound represented by Formula (I) or a pharmaceutical composition containing the crystals. Cancer to be preferably treated is selected from brain tumor (such as glioblastoma), urological cancer (such as bladder cancer and renal cancer), genital cancer (such as prostate cancer, ovarian cancer, and uterine cancer), lymphatic tumor, gastrointestinal cancer (such as stomach cancer, esophageal cancer, large intestine cancer, and colon cancer), throat cancer, lung cancer (such as lung adenocarcinoma, small cell lung cancer, non-small cell lung cancer), pancreatic cancer, breast cancer, head and neck cancer, and thyroid cancer. More preferable are breast cancer, brain tumor, bladder cancer, kidney cancer, prostate cancer, ovarian cancer, uterine cancer, lung cancer, pancreatic cancer, and head and neck cancer. Even more preferable is breast cancer.

One or more hydrogen, carbon, and/or other atoms of the compound represented by Formula (I) or Formula (II) may be substituted with isotopes of hydrogen, carbon, and/or other atoms, respectively. Examples of such isotopes encompass hydrogen, carbon, nitrogen, oxygen, phosphorus, sulfur, fluorine, iodine, and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$, and $^{36}Cl$, respectively. The compounds represented by Formula (I) or Formula (II) encompass compounds substituted with such isotopes. Isotope-substituted compounds are also useful as pharmaceutical products, and all radiolabeled forms of the compounds represented by Formula (I) or Formula (II) are encompassed. Also, a "radiolabeling method" for producing the "radiolabeled form" is encompassed within the present invention, and the "radiolabeled form" is useful as a research and/or diagnostic tool in metabolic pharmacokinetic studies and binding assays.

The radiolabeled form of the compound represented by Formula (I) or Formula (II) can be prepared by methods well known in the art. For example, a tritium-labeled compound represented by Formula (I) or Formula (II) can be prepared by introducing tritium into a specific compound represented by Formula (I) or Formula (II) by a catalytic dehalogenation reaction using tritium. This method encompasses reacting tritium gas and a precursor, which is obtained by substituting a compound represented by Formula (I) or Formula (II) with a halogen suitably, in the presence of a suitable catalyst such as Pd/C in the presence or absence of a base. For another suitable method for preparing a tritium-labeled compound, "Isotopes in the Physical and Biomedical Sciences, Vol. 1, Labeled Compounds (Part A), Chapter 6 (1987)" can be referred to. A $^{14}C$-labeled compound can be prepared by using a raw material having $^{14}C$ carbon.

Examples of pharmaceutically acceptable salts of the compound represented by Formula (I) or Formula (II) include salts of the compound represented by Formula (I) or Formula (II) and inorganic acids (such as hydrochloric acid, sulfuric acid, nitric acid, carbonic acid, hydrobromic acid, phosphoric acid, and hydroiodic acid) and organic acids (such as formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, and ethanesulfonic acid). In particular, examples include salts of hydrochloric acid, p-toluenesulfonic acid, sulfuric acid, phosphoric acid, fumaric acid, tartaric acid, and methanesulfonic acid. These salts can be formed by commonly performed methods.

Hydrochloride, p-toluenesulfonate, or other pharmaceutically acceptable salts of the compound represented by Formula (I) or pharmaceutically acceptable salts of the compound represented by Formula (II) of the present invention may form solvates (such as hydrates and ethanolates), co-crystals, and/or crystal polymorphs, and the present invention encompasses such various solvates, co-crystals, and crystal polymorphs as well. In the "solvate", any number of solvent molecules (such as water molecules) may be coordinated with hydrochloride, p-toluenesulfonate, or other pharmaceutically acceptable salts of the compound represented by Formula (I) or pharmaceutically acceptable salts of the compound represented by Formula (II). By being left to stand in the atmosphere, hydrochloride, p-toluenesulfonate, or other pharmaceutically acceptable salts of the compound represented by Formula (I) or pharmaceutically acceptable salts of the compound represented by Formula (II) may absorb water, resulting in attachment of adsorbed water or formation of hydrates. Also, recrystallization of hydrochloride, p-toluenesulfonate, or other pharmaceutically acceptable salts of the compound represented by Formula (I) or pharmaceutically acceptable salts of the compound represented by Formula (II) may form crystal polymorphs. The "co-crystal" means that hydrochloride, p-toluenesulfonate, or other pharmaceutically acceptable salts of the compound represented by Formula (I) or pharmaceutically acceptable salts of the compound represented by Formula (II) and counter molecules are present within the same crystal lattice, and may be formed with any number of counter molecules.

Hydrochloride, p-toluenesulfonate, or other pharmaceutically acceptable salts of the compound represented by Formula (I) or solvates thereof of the present invention may form prodrugs, and the present invention encompasses such various prodrugs as well. The prodrug is a derivative of the compound of the present invention having a chemically or metabolically decomposable group, and is a compound that becomes a pharmacologically active compound of the present invention by solvolysis or in vivo under physiological conditions. The prodrug encompasses a compound that is converted into the compound represented by Formula (I) by enzymatic oxidation, reduction, hydrolysis, or the like under physiological conditions in a living body, and a compound that is converted into the compound represented by Formula (I) by hydrolysis due to gastric acid or the like. A method for selecting and a method for producing an appropriate prodrug derivative are described in, for example, "Design of Prodrugs, Elsevier, Amsterdam, 1985". The prodrug may itself have activity.

The compound represented by Formula (I):

[Chemical Formula 17]

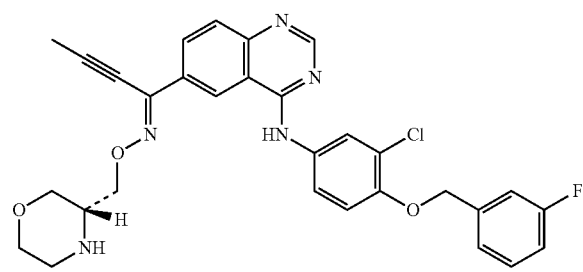

(I)

is an EGF receptor/HER2 dual inhibitor described in Patent Document 1, and a pharmaceutical composition containing the compound is useful for preventing or treating cancer. The compound represented by Formula (I) can be prepared according to the method described in Patent Document 1 or 2.

Specifically, the compound represented by Formula (I) can be produced by reacting the compound represented by the following formula:

[Chemical Formula 18]

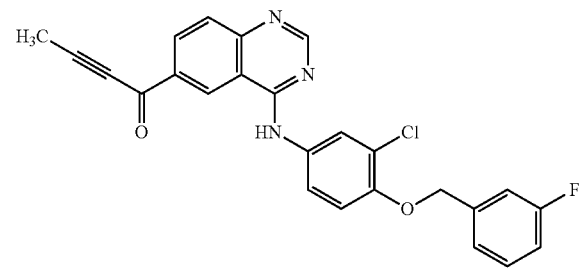

with the compound represented by the following formula:

[Chemical Formula 19]

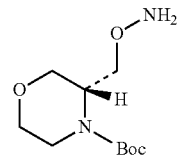

under acidic conditions, and neutralizing the resulting crude product.

Alternatively, the compound represented by Formula (I) can be produced by reacting the compound represented by the following formula:

[Chemical Formula 20]

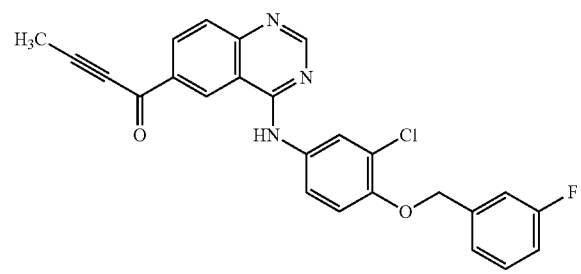

with the compound represented by the following formula:

[Chemical Formula 21]

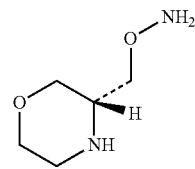

or salt thereof or their solvates under acidic conditions, and neutralizing the resulting crude product.

For example, free base A of compound (I) and free base B of compound (I) can be produced as the compound represented by Formula (I) by the method described in the Examples herein.

Then, the obtained compound represented by Formula (I):

[Chemical Formula 22]

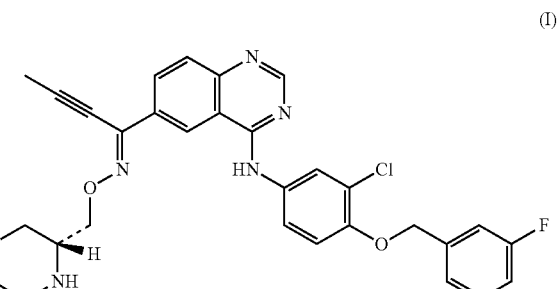

(I)

is dissolved in various organic solvents and crystallized under acidic conditions, and thereby an acid addition salt of the compound represented by Formula (I) or crystals thereof can be produced.

Examples of acids include inorganic acids (such as hydrochloric acid, sulfuric acid, nitric acid, carbonic acid, hydrobromic acid, phosphoric acid, and hydroiodic acid) and organic acids (such as formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, and ethanesulfonic acid). In particular, examples include hydrochloric acid and p-toluenesulfonic acid.

In monohydrochloride of the compound represented by Formula (I), there are Form I, Form II, Form III, Form V, Form VI and Form VII, and ethanolate crystal forms. Also, there are crystal forms of mono-p-toluenesulfonate; monosulfate and monosulfate hydrate; monophosphate and monophosphate hydrate; and monofumarate of the compound represented by Formula (I). These crystal polymorphs can be produced in a differentiated manner according to the type of organic solvent used for crystallization and which of free base A of the compound represented by Formula (I) or free base B of the compound represented by Formula (I) is used as the compound represented by Formula (I).

Monohydrochloride crystals Form I of the compound represented by Formula (I) can be produced by dissolving free base A of the compound represented by Formula (I) in methanol and causing crystallization in the presence of hydrochloric acid.

Monohydrochloride crystals Form II of the compound represented by Formula (I) can be produced by dissolving free base A of the compound represented by Formula (I) in a mixed solvent of methanol and ethyl acetate (methanol: ethyl acetate=1:1) and causing crystallization in the presence of hydrochloric acid.

Monohydrochloride crystals Form III of the compound represented by Formula (I) can be produced by dissolving free base A of the compound represented by Formula (I) in a mixed solvent of methanol and ethyl acetate (methanol: ethyl acetate=1:4) and causing crystallization in the presence of hydrochloric acid.

Monohydrochloride crystals Form V of the compound represented by Formula (I) can be produced by dissolving free base B of the compound represented by Formula (I) in 2-propanol and causing crystallization in the presence of acid.

Monohydrochloride crystals Form VI of the compound represented by Formula (I) can be produced by dissolving free base A of the compound represented by Formula (I) in 2-propanol and causing crystallization in the presence of hydrochloric acid.

Monohydrochloride crystals Form VII of the compound represented by Formula (I) can be produced by dissolving crystal form VI of monohydrochloride of the compound represented by Formula (I) in 1,2-dimethoxyethane and causing crystallization.

Monohydrochloride ethanolate crystals of the compound represented by Formula (I) can be produced by adding monohydrochloride crystal Form I as seed crystals to a mixed solution of ethyl acetate and ethanol.

Free base crystals of the compound represented by Formula (I) can be produced by dissolving free base B of the compound represented by Formula (I) in a mixed solution of hexane and ethyl acetate and causing crystallization.

Mono-p-toluenesulfonate crystal Form I of the compound represented by Formula (I) can be produced by purifying free base A of the compound represented by Formula (I) by an ordinary method, dissolving the free base in ethyl acetate, adding 1 mol/L of a solution of p-toluenesulfonic acid in methanol, and causing crystallization.

Monosulfate crystals of the compound represented by Formula (I) can be produced by dissolving free base A of the compound represented by Formula (I) in acetonitrile, adding 1 mol/L of sulfuric acid in methanol, and causing crystallization.

Monosulfate monohydrate crystals of the compound represented by Formula (I) can be produced by dissolving trihydrate crystals of the compound represented by Formula (I) in a mixed solution of acetonitrile and 2-propanol, adding 0.1 mol/L of sulfuric acid, then concentrating the mixture, further, adding a mixed solution of methanol and water, and shaking and then concentrating the mixture.

Monophosphate crystals of the compound represented by Formula (I) can be produced by dissolving trihydrate crystals of the compound represented by Formula (I) in a mixed solution of acetonitrile and 2-propanol, adding 0.1 mol/L of phosphoric acid, then concentrating the mixture, further, adding a mixed solution of ethanol and water, and shaking and then concentrating the mixture.

Monophosphate dihydrate crystal Form I of the compound represented by Formula (I) can be produced by dissolving trihydrate crystals of the compound represented by Formula (I) in a mixed solution of acetonitrile and 2-propanol, adding 0.1 mol/L of phosphoric acid, then concentrating the mixture, further, adding a mixed solution of methanol and water, and shaking and then concentrating the mixture.

Monofumarate crystal Form I of the compound represented by Formula (I) can be produced by dissolving trihydrate crystals of the compound represented by Formula (I) in a mixed solution of acetonitrile and 2-propanol, adding 0.1 mol/L of a mixed solution of fumaric acid in methanol and water, then concentrating the mixture, further, adding methanol and water, and shaking and then concentrating the mixture.

Monofumarate crystal Form II of the compound represented by Formula (I) can be produced by dissolving trihydrate crystals of the compound represented by Formula (I) in a mixed solution of acetonitrile and 2-propanol, adding 0.1 mol/L of a mixed solution of fumaric acid in methanol and water, then concentrating the mixture, further, adding acetonitrile and water, and shaking and then concentrating the mixture.

Hereinafter, methods for identifying the crystals of the present invention are described.

Unless otherwise noted, the numerical values provided in the description and the claims are approximate values. Numerical values vary due to the equipment calibration, equipment errors, purity of materials, crystal size, and sample size, among other factors.

As used herein, the "crystal" means a substance having an ordered arrangement of atoms, ions, molecules and the like that constitute a solid, and accordingly the substance has periodism and anisotropism. The degree of crystallinity of a crystal form can be determined by various techniques including, for example, X-ray powder diffractometry, moisture sorption desorption, differential scanning calorimetry, thermogravimetry/differential thermal analysis, solution colorimetry, and dissolution properties.

X-Ray Powder Diffraction (XRPD)

In general, crystalline organic compounds consist of a large number of atoms that are arranged in a periodic array in three-dimensional space. The structural periodicity normally manifests physical properties, which can be explicitly distinguished by most spectroscopic probes (e.g., X-ray diffraction, an infrared spectrum, a Raman spectrum and solid state NMR). The X-ray powder diffraction (XRPD) is acknowledged to be one of the most sensitive analytical methods for measuring solid crystallinity. X-rays which are irradiated to crystals are reflected by the crystal lattice planes and mutually interfere. Then, only the diffraction lines in the direction which fulfill the conditions predicted by Bragg's law are intensified and the ordered diffraction lines corresponding to the periodicity of the structure are observed. On the other hand, in the case of amorphous solids, the well-ordered diffraction lines over a long-range are not observed. Amorphous solids usually show non-characteristic broad XRPD patterns, because they do not have the ordered iteration periodicity in the structure, so that the diffraction phenomenon does not occur.

The crystal forms of acid addition salts of the compound represented by Formula (I) disclosed herein preferably have distinguishable X-ray powder diffraction profiles. For example, crystals containing monohydrochloride or mono-p-toluenesulfonate of the compound represented by Formula (I) preferably are distinguishable from other crystal forms according to the presence of characteristic diffraction peaks. The characteristic diffraction peaks as used herein are peaks selected from the observed diffraction patterns. The characteristic diffraction peaks are selected from preferably about 20, more preferably about 10, and most preferably about 5 peaks in a diffraction pattern.

In general, diffraction angles ($2\theta$) in X-ray powder diffraction may have a margin of error within a range of $\pm 0.2°$, the value of a diffraction angle in X-ray powder diffraction should be understood as including values within a range of around $\pm 0.2°$. Therefore, the present invention includes not only crystals whose diffraction angles of the peaks in X-ray powder diffraction perfectly match, but also crystals whose diffraction angles of the peaks match within an error of around $\pm 0.2°$.

In general, it is known that the absolute intensities and the relative intensities of the peaks shown in the Tables and Figures below may vary due to many factors such as selected orientation effects of crystals in the X-ray beam, effect of coarse particle, purity of the material being analyzed or degree of crystallinity of the sample, for example. The peak positions may also shift for variations in sample height. Furthermore, measurements using a different wavelength will result in different shifts according to the Bragg equation ($n\lambda = 2d \sin \theta$). Different XRPD patterns obtained by using such different wavelengths are also within the scope of the present invention.

TG/DTA (Thermogravimetry/Differential Thermal Analysis)

TG/DTA is one of the main measuring methods for thermal analysis, and is a method for measuring the weight and the thermal properties of the substance as an aggregate of an atom(s) and a molecule(s).

TG/DTA is the method for measuring a temperatures or changes in weight and heat capacity over time of a pharmaceutical active ingredient. TG (thermo gravity) and DTA (differential thermal analysis) curve are obtained by plotting the obtained data against temperature or time. TG/DTA curve provides the information about the changes in weight and heat capacity related to decomposition, dehydration, oxidation, reduction, sublimation and evaporation of an active pharmaceutical ingredient.

It is known that the temperature and the weight changes observed in TG/DTA may depend on the heating rate, sample preparation technique and specific device. Therefore, in TG/DTA, a "melting point" means onset temperature which is unaffected by technique for preparing the sample. In identifying a crystal, the melting point as well as the overall pattern is important and may change somewhat depending on a measurement condition and apparatus.

DSC (Differential Scanning Calorimetry)

DSC is one of the main measuring methods for thermal analysis, and is a method for measuring the thermal properties of the substance as an aggregate of an atom(s) and a molecule(s). A differential scanning calorimetry curve can be obtained by measuring temperatures or change of heat capacity over time of an active pharmaceutical ingredient by DSC, and plotting the obtained data to temperatures or times. From a differential scanning calorimetry curve, the information about the onset temperature, melting endothermic maximum and enthalpy of an active pharmaceutical ingredient can be obtained.

As to DSC, it is known that the observed temperature can depend on the rate of temperature change, the sample preparations techniques or the specific devices. Therefore, in DSC, "the melting point" means the onset temperature which is unaffected by technique for preparing the sample. The error span in the onset temperature obtained from a differential scanning calorimetry curve is approximately $\pm 2°$ C. In identifying a crystal, the melting point as well as the overall pattern is important and may change somewhat depending on a measurement condition and apparatus.

(Moisture Sorption-Desorption Isothermal Measurement)

Moisture sorption-desorption isothermal measurement is measuring the weight changes of a subject solid under various relative humidity conditions, and is a method for determining moisture sorption-desorption behaviors.

As a basic measurement method, the relative humidity is increased in increments of 5% or 10% based on the dry weight at 0% Target % $P/P_0$ (relative humidity 0%), and after the weights at respective relative humidities are stabilized, the amount of adsorbed water can be obtained from the weight increased from a reference value. Similarly, it is possible to measure the amount of desorbed water by reducing the relative humidity in increments of 5% or 10% from 100% Target % $P/P_0$.

Sorption and desorption isotherms can be obtained by plotting the weight change values at respective relative humidities. From the results, it is possible to investigate the sorption and desorption phenomena of attached moisture at respective humidities. Also, when anhydride crystals and hydrate crystals undergo mutual crystal transition due to humidity, it is possible to calculate the humidity, at which crystal transition occurs, and the amount of water of crystallization.

Since the sorption and desorption of attached water and water of crystallization are affected by the particle size, degree of crystallinity, crystal habit, and the like, the measurement results may slightly vary.

(Photostability Test)

The photostability test is one of the methods for measuring chemical or physicochemical changes of an active pharmaceutical ingredient or a pharmaceutical preparation caused by light exposure to evaluate properties of a sample with respect to light. In the photostability test, a sample such as an active pharmaceutical ingredient or a pharmaceutical preparation is irradiated with light at a specified output for a certain period of time. Properties of the sample with respect to light can be evaluated by analyzing the impurities and analogous substances, crystal form, color difference, and the like of the sample by scientific techniques (such as high performance liquid chromatography, X-ray crystal diffraction, and colorimetry) when a specified total illuminance is reached. In order to verify that a specified amount of light exposure is attained, the amount of light exposure is managed using a radiometer or a luminometer, and a test is carried out using an actinometric system.

The pharmaceutical composition containing an acid addition salt or crystals of the acid addition salt of the compound represented by Formula (I) of the present invention is highly useful as a therapeutic agent or a prophylactic agent for cancer.

The acid addition salt or crystals of the acid addition salt of the compound represented by Formula (I) of the present invention can be administered to a human patient as-is, or can be administered as a pharmaceutical composition obtained by mixing the crystals with a suitable carrier or excipient. Drug formulation and administration techniques are suitably selected and used by combining pharmaceutical formulations and techniques known to those skilled in the art.

Routes of administration of the acid addition salt or crystals of the acid addition salt of the compound represented by Formula (I) or the pharmaceutical composition containing them of the present invention can include, but are not limited to, oral, rectal, transmucosal or enteral administrations, or intramuscular, subcutaneous, intraspinal, intrathecal, direct intraventricular, intravenous, intravitreal, intraperitoneal, intranasal, intraocular injections. Preferable routes of administration are oral or injection (intramuscular, subcutaneous, intraspinal, intrathecal, intravenous). A particularly preferable route of administration is oral.

The pharmaceutical composition of the present invention can be produced by a production method well known in the art, such as commonly used mixing, dissolution, granulation, sugar coat formation, powderization, emulsification, encapsulation, entrapment, and lyophilization processes.

The acid addition salt or crystals of the acid addition salt of the compound represented by Formula (I) or the pharmaceutical composition containing them of the present invention can be administered by injection using an aqueous solution, preferably a physiologically compatible buffer such as Ringer's solution or physiological saline.

The acid addition salt or crystals of the acid addition salt of the compound represented by Formula (I) or the pharmaceutical composition containing them of the present invention can be transmucosally administered using a penetrant suitable for a barrier to be penetrated. A penetrant that is generally known in the art can be used.

The acid addition salt or crystals of the acid addition salt of the compound represented by Formula (I) or the pharmaceutical composition, in which they are combined with a pharmaceutically acceptable carrier well known in the art, of the present invention can be orally administered. By being combined with such a carrier, the acid addition salt or crystals of the acid addition salt of the compound represented by Formula (I) of the present invention can be administered as a tablet, pill, lozenge, sugar-coated tablet, capsule, solution, gel, syrup, or suspension. A pharmaceutical composition for oral administration can be formed by using a solid excipient, adding another suitable adjuvant if desired, then pulverizing the obtained mixture, and processing the granular mixture to obtain a tablet or a core of a sugar-coated tablet.

Useful excipients are, in particular, fillers such as sugars including lactose, sucrose, mannitol, or sorbitol, cellulose preparations of, for example, corn starch, wheat starch, rice starch, and potato starch, gelatin, tragacanth gum, methylcellulose, hydroxypropyl methylcellulose, and/or sodium carboxymethyl cellulose. If necessary, disintegrators such as agar and alginic acid can be added. A salt such as sodium alginate can be used as well.

Pharmaceutical compositions usable for oral administration include push-fit capsules formed of gelatin, hermetically sealed capsules formed of gelatin and a plasticizer such as glycerol or sorbitol, and the like. Push-fit capsules can contain an active component mixed with a filler such as lactose, a binder such as starch, and/or a lubricant such as talc or magnesium stearate and, if desired, a stabilizer. In soft capsules, crystals of the acid addition salt of the compound represented by Formula (I) of the present invention can be dissolved or suspended in a suitable liquid such as fatty oil, liquid paraffin, or liquid polyethylene glycol. A stabilizer can be added to these formulations as well.

The pharmaceutical composition can also contain a suitable carrier or excipient having a solid or gel phase. Examples of such carriers or excipients include calcium carbonate, calcium phosphate, various sugars, starch, cellulose derivatives, gelatin, polymers such as polyethylene glycol, and the like.

A therapeutically effective amount of the acid addition salt or crystals of the acid addition salt of the compound represented by Formula (I) of the present invention can be initially estimated from a cell culture assay. Then, a large dosage can be formulated for use in animal models such that a circulating level range including IC50 (i.e., a level of the acid addition salt or crystals of the acid addition salt of the compound represented by Formula (I) or the pharmaceutical composition containing them of the present invention, which achieves inhibition of half of the maximal PK activity) determined in a cell culture is achieved. Then, an amount useful in humans can be more precisely determined using such information.

The therapeutic effect of the acid addition salt or crystals of the acid addition salt of the compound represented by Formula (I) or the pharmaceutical composition containing them of the present invention can be measured by a standard pharmaceutical procedure in a cell culture or an experimental animal. For example, the therapeutic effect may be evaluated according to the biological test method described in International Publication No. WO2006/090717. Data obtained from such a cell culture assay and an animal experiment can be used for formulating a dosage range for use in humans. The dosage can be altered according to the form of administration used and the route of administration utilized. A precise route of administering a formulation and dosage can be selected by individual physicians in consideration of patient conditions.

It is also an embodiment of the present invention that the acid addition salt or crystals of the acid addition salt of the compound represented by Formula (I) or the pharmaceutical composition containing them of the present invention can be combined with another pharmaceutical agent for treating a disease and a disorder. For example, the acid addition salt or crystals of the acid addition salt of the compound represented by Formula (I) or the pharmaceutical composition containing them of the present invention can be combined with another anticancer agent or the like. For example, the acid addition salt or crystals of the acid addition salt of the compound represented by Formula (I) or the pharmaceutical composition containing them of the present invention can also be used in combination, or as a mixture, with another anticancer agent. Examples include trastuzumab, microtubule inhibitors [vinorelbine, taxane-based pharmaceutical agents (such as paclitaxel and docetaxel), irinotecan, eribulin mesylate], platinum-based pharmaceutical agents (such as cisplatin, carboplatin, oxaliplatin, and nedaplatin), 5-FU-based pharmaceutical agents (such as capecitabine and 5-fluorouracil), breast cancer hormone therapies, HER2 inhibitors (trastuzumab, pertuzumab, lapatinib tosylate hydrate, neratinib, margetuximab), HER2 antibody conjugate drugs (trastuzumab emtansine (T-DM1), MM-302), HDAC inhibitors (entinostat), PARP inhibitors (talazoparib, niraparib, olaparib, veliparib), immunotherapeutic vaccines (such as nelipepimut-S), CDK4/6 inhibitors (ibrance, ribociclib, abemaciclib), PI3K/mTOR inhibitors (buparlisib, taselisib, everolimus, alpelisib), immune checkpoint inhibitors (such as PD1/PD-L1 inhibitors (nivolumab, atezolizumab, pembrolizumab), and the like. Also, two or more of the above anticancer agents can be used in combination.

The dosage of the acid addition salt or crystals of the acid addition salt of the compound represented by Formula (I) of the present invention also varies according to the disease state, route of administration, age of a patient, or body weight. The dosage is usually 10 to 1600 mg/person/day, preferably 100 to 1200 mg/person/day, and most preferably 200 to 800 mg/person/day in the case of oral administration to an adult.

The present invention is described in more detail by way of the following Examples and Reference Examples. These do not limit the present invention. Concerning numerical values (for example, quantity, temperature, etc.), some errors and deviations should be taken into consideration.

Unless otherwise indicated, % is the weight % of a component and is based on the total weight of a composition, and the pressure is atmospheric pressure or a pressure in the vicinity thereof.

Terms used herein are explained below:
g: gram
L: liter
mg: milligram
mL: milliliter
Boc: tert-butoxycarbonyl
(X-Ray Powder Diffraction Pattern Measurement)
Data of X-ray powder diffraction measurement of the obtained crystals in each Example is obtained according to X-ray powder diffraction analysis method in General tests in Japanese Pharmacopoeia as following conditions.
(Method A)
(Device)
D-8 Discover by Bruker
(Operation Method)
Samples were measured under the following conditions.
Measuring method: Reflection method
Light source: Cu tube
Wavelength used: CuKα ray
Tube current: 40 mA
Tube voltage: 40 kV
Sampling plate: Glass, aluminum
X-ray incident angle: 3-40°
(Method B)
(Device)
MiniFlex 600 by Rigaku
(Operation Method)
Samples were measured under the following conditions.
Measuring method: Reflection method
Light source: Cu tube
Used Wavelength: CuKα ray
Tube current: 15 mA
Tube voltage: 40 kV
Sampling plate: Circular, non-reflective sampling plate
X-ray incident angle: 4-40°
(DSC Measurement)
About 1 mg of the crystals obtained in each Example were weighed, stuffed in a high pressure pan made of gold-plated steal and measured under sealed system. The measurement conditions were as follows.
(Measurement Conditions)
Device: DSC Discovery by TA Instruments
Measurement temperature range: 25° C-250° C.
Rate of temperature increase: 10° C./min
(TG/DTA Measurement)
About 10 mg of the crystals obtained in each Example was weighed, stuffed in aluminum pan and measured under open system. The measurement conditions were as follows.
(Measurement Conditions)
Device: TG/DTA 6300 by Hitachi High-Tech Science
Measurement temperature range: 30° C.-300° C.
Rate of temperature increase: 10° C./min
(NMR Measurement)
In NMR data shown in Examples and Reference Examples, not all measured peaks may be described.
(HPLC Measurement)
(Method A)
Device: Agilent 1290 Infinity
Detection wavelength: 232 nm
Column: ZORBAX SB-C18, 1.8 μm (2.1 mm×30 mm)
Column temperature: around 60° C.
Mobile phase: 0.1% aqueous trifluoroacetic acid solution/acetonitrile mixed solution (gradient from 90:10 to 10:90)
Flow rate: 1.2 mL/min
Injection amount: 1 μL
(Method B)
Device: Shimadzu 2010 Series or Shimadzu 10A VP Series
Column: CAPCELL PAK C18 MGII 3 μm Inner diameter 4.6 mm Length 150 mm
Mobile phase: [A] 10 mM aqueous ammonium acetate solution/[B] acetonitrile-methanol mixed solution (1:1)
Gradient program is shown in Table 1.

TABLE 1

| Time after injection (min) | Mobile phase A | Mobile phase B |
| --- | --- | --- |
| 0 to 40 | 40 | 60 |
| 40 to 60 | 40 → 10 | 60 → 90 |
| 60 to 70 | 10 | 90 |

Flow rate: 1.0 mL/min
Detection wavelength: 225 nm
Injection amount: 10 μL
Column temperature: 35° C.
(Moisture Sorption-Desorption Isothermal Measurement)
Moisture sorption-desorption isothermal measurement was performed on the crystals obtained in each Example. About 10 mg of a sample was weighed onto a sample pan, and measurement was performed. Measurement conditions are as shown below.

Device: DVS Advantage by Surface Measurement Systems Ltd.
Measurement points: from 0% Target % P/P₀ to 95% Target % P/P₀ in increments of 5%, then from 95% Target % P/P₀ to 0% Target % P/P₀ in decrements of 5%
Temperature: 25° C.
(Photostability Measurement)

A photostability test was performed using a photostability tester (model LTL200A5-15WCD) by Nagano Science. A D65 lamp was used as an irradiation source of light, and light was irradiated to a total illuminance of about 1.2 million lx·hr under 4000 lx·hr conditions.

REFERENCE EXAMPLE 1

Synthesis of Free Base A of Compound (I)

[Chemical Formula 23]

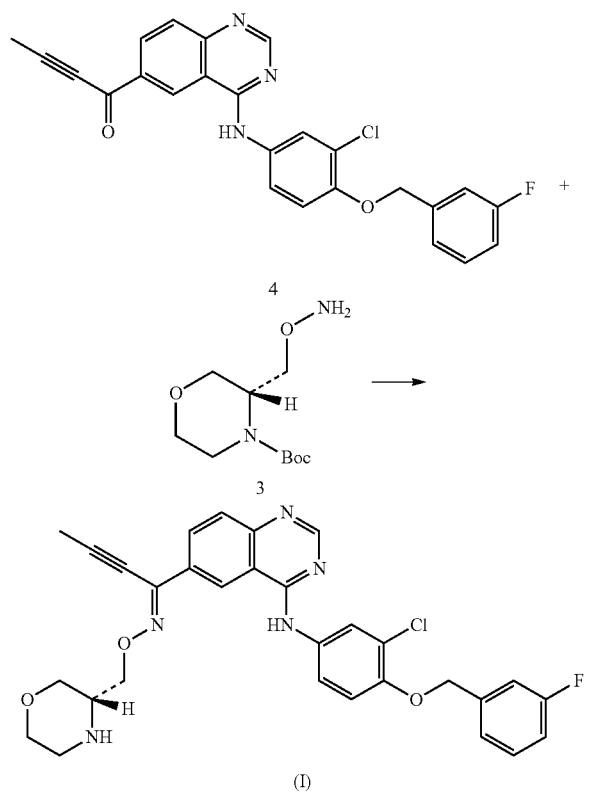

Compound 4 (8.23 g, 18.5 mmol) and Compound 3 (6.43 g, 27.7 mmol) were suspended in dioxane (326 mL), and a 2 mol/L solution (23.3 mL) of methanesulfonic acid in methanol was added. The mixture was stirred at 60° C. for 4 hours, then another portion of 2 mol/L methanesulfonic acid (14.1 mL) in methanol was added, and the mixture was stirred at 60° C. for 17 hours. The reaction solution was diluted with ethyl acetate (815 mL) and water (200 mL), and an aqueous potassium carbonate solution (20.65 g of potassium carbonate, 150 mL of water) was added for extraction. The organic layer was washed with saline (50 mL of brine, 250 mL of water). Then, the organic layer was dried over magnesium sulfate and filtered, then the filtrate was concentrated, and thus free base A (11.83 g) of Compound (I) was obtained as brown oil.

REFERENCE EXAMPLE 2

Synthesis of Free Base B of Compound (I)

Free base A (6.88 g) synthesized using Compound 4 (4.94 g) according to the synthesis method of Reference Example 1 was dissolved in methanol (28 mL), and a 4 mol/L solution (2.5 mL) of hydrochloric acid in ethyl acetate was added. Stirring the mixture at room temperature for 2 hours yielded precipitates. The mixture was diluted with ethyl acetate (50 mL), and methanol was distilled off under reduced pressure. This operation was repeated, and the mixture was further diluted with ethyl acetate (30 mL) and stirred at room temperature for 30 minutes. The resulting solids were filtered, washed with ethyl acetate (30 mL), and dried, and thus monohydrochloride (5.04 g) of Compound (I) was obtained. Then, 3.00 g of the monohydrochloride was suspended in ethyl acetate (50 mL), an aqueous potassium carbonate solution (1.04 g of potassium carbonate, 15 mL of water) was added at 0° C., and the mixture was extracted with ethyl acetate. The extract was washed with brine, dried over anhydrous sodium sulfate, and filtered, and then the filtrate was concentrated under reduced pressure. Diethyl ether (24 mL) and hexane (6 mL) were added to the residue, the resulting solids were washed with a mixed solution of hexane:diethyl ether (1:1), and thus free base B (2.63 g) of Compound (I) was obtained as pale yellow solids.

EXAMPLE 1

Synthesis of Monohydrochloride Crystal Form I of Compound (I)

After free base A (1.18 g) of Compound (I) was dissolved in ethyl acetate (8 mL) and filtered, the filtrate was concentrated under reduced pressure to a half volume, and a 4 mol/L solution (0.42 mL) of hydrochloric acid in ethyl acetate was added. Diethyl ether (2 mL) was added, and the resulting precipitates were filtered and washed with a mixed solution of diethyl ether:ethyl acetate (2:3) and then diethyl ether. Solids (817 mg) collected by filtration were dissolved in methanol (20 mL) under warming, concentrated under reduced pressure to a total amount of 3.6 g, and left to stand at room temperature. Precipitates were filtered, washed with cold methanol and then diethyl ether and dried, and thus monohydrochloride crystal Form I (701 mg) of Compound (I) was obtained as yellow crystals.

$^1$H-NMR (300 MHz, DMSO-d6) δ 2.28 (6H, s), 3.08-3.28 (2H, m), 3.58-3.75 (3H, m), 3.90-3.94 (1H, m), 4.03 (1H, dd, J=12, 2.7 Hz), 4.44 (2H, d, J=5.4 Hz), 5.27 (2H, s), 7.15-7.22 (1H, m), 7.26-7.35 (3H, m), 7.44-7.51 (1H, m), 7.72 (1H, dd, J=9.0, 2.4 Hz), 7.82 (1H, d, J=8.7 Hz), 7.99 (1H, d, J=2.4 Hz), 8.26 (1H, dd, J=8.7, 1.8 Hz), 8.60 (1H, s), 8.88 (1H, d, J=1.5 Hz), 9.29 (1H, s), 10.20 (1H, s).

Elemental analysis:
calculated value: C, 60.41; H, 4.73; Cl, 11.89; F, 3.19; N, 11.74
measured value: C, 60.17; H, 4.79; Cl, 11.62; F, 3.06; N, 11.81

The results of X-ray powder diffraction are shown in FIG. 1 and Table 2. (Measurement conditions: Method A)

TABLE 2

| 2θ |
|---|
| 6.838 |
| 7.982 |

TABLE 2-continued

| 2θ |
|---|
| 14.122 |
| 17.941 |
| 18.451 |
| 20.569 |
| 20.989 |
| 22.528 |
| 25.843 |
| 28.409 |

Diffraction angles of major peaks (2θ) in X-ray powder diffraction spectrum: 8.0°±0.2°, 14.1°±0.2°, 20.6°±0.2°, 21.0°±0.2°, 25.8°±0.2°.

The results of TG/DTA measurement are shown in FIG. 4. The observed onset temperature was about 234° C. The weight loss of about 0.91% was observed on TG.

The results of DSC measurement are shown in FIG. 7. The observed onset temperature was about 239° C.

The results of moisture sorption-desorption isothermal measurement are shown in FIG. 45. In the moisture sorption isothermal measurement, the ratio of the increased mass at 95% Target % $P/P_0$ to the mass at 0% Target % $P/P_0$ was about 0.8. In the moisture desorption isothermal measurement, the ratio at 0% Target % $P/P_0$ was about 0.08.

EXAMPLE 2

Synthesis of Monohydrochloride Crystal Form V of Compound (I)

2-Propanol (5.0 mL) was added to free base B (500 mg) of Compound (I), and the mixture was dissolved under warming at 65° C. After cooling, a 4 mol/L solution (212 μL) of hydrochloric acid in ethyl acetate was added. The mixture was stirred at room temperature for 5 minutes and concentrated under reduced pressure to a total amount of 3.09 g. The resulting precipitates were filtered and washed with cold 2-propanol (3 mL). The obtained solids were dissolved in methanol (13 mL) under warming, and concentrated under reduced pressure to a total amount of 3.03 g. The solution was diluted with ethyl acetate (6.0 mL) and again concentrated under reduced pressure to a total amount of 2.84 g. Precipitates were collected by filtration, washed with cold ethyl acetate (5 mL), and dried, and thus monohydrochloride crystal Form V (382 mg) of Compound (I) was obtained as yellow crystals.

The results of X-ray powder diffraction are shown in FIG. 2 and Table 3. (Measurement conditions: Method A)

TABLE 3

| 2θ |
|---|
| 7.906 |
| 9.734 |
| 11.933 |
| 15.791 |
| 18.532 |
| 23.919 |
| 25.912 |
| 26.208 |
| 26.728 |
| 28.399 |

Diffraction angles of major peaks (2θ) in X-ray powder diffraction spectrum: 23.9°±0.2°, 25.9°±0.2°, 26.2°±0.2°, 26.7°±0.2°, 28.4°±0.2°.

The results of TG/DTA measurement are shown in FIG. 5. The observed onset temperature was about 238° C. The weight loss of about 1.34% was observed on TG.

The results of DSC measurement are shown in FIG. 8. The observed onset temperature was about 234° C.

The results of the moisture sorption-desorption isothermal measurement are shown in FIG. 46. In the moisture sorption isothermal measurement, the ratio of the increased mass at 95% Target % $P/P_0$ to the mass at 0% Target % $P/P_0$ was about 1.7. In the moisture desorption isothermal measurement, the ratio at 0% Target % $P/P_0$ was about 0.05.

EXAMPLE 3

Synthesis of Monohydrochloride Crystal Form VI of Compound (I)

Free base A (1.00 g) of Compound (I) was dissolved in 2-propanol (8.0 mL), then a 4 mol/L solution (318 μL) of hydrochloric acid in ethyl acetate was added, and the mixture was stirred at room temperature for 1 hour and at 0° C. for 1 hour. The mixture was stirred at room temperature for 30 minutes, and then precipitates were collected by filtration. The precipitates were washed with 2-propanol and dried, and thus monohydrochloride crystal Form VI (592 mg) of Compound (I) was obtained as pale yellow crystals.

The results of X-ray powder diffraction are shown in FIG. 3 and Table 4. (Measurement conditions: Method A)

TABLE 4

| 2θ |
|---|
| 5.416 |
| 8.867 |
| 11.707 |
| 13.752 |
| 16.253 |
| 20.854 |
| 21.61 |
| 23.187 |
| 23.718 |
| 26.616 |

Diffraction angles of major peaks (2θ) in X-ray powder diffraction spectrum: 5.4°±0.2°, 16.3°±0.2°, 21.6°±0.2°, 23.2°±0.2°, 23.7°±0.2°.

The results of TG/DTA measurement are shown in FIG. 6. The observed onset temperature was about 225° C. The weight loss of about 0.98% was observed on TG.

The results of DSC measurement are shown in FIG. 9. The observed onset temperature was about 225° C.

The results of the moisture sorption-desorption isothermal measurement are shown in FIG. 47. In the moisture sorption isothermal measurement, the ratio of the increased mass at 95% Target % $P/P_0$ to the mass at 0% Target % $P/P_0$ was about 0.5. In the moisture desorption isothermal measurement, the ratio at 0% Target % $P/P_0$ was about 0.06.

EXAMPLE 4

Synthesis of Monohydrochloride Crystal Form II of Compound (I)

Free base A (50.0 mg) of Compound (I) was dissolved in methanol (100 μL) and ethyl acetate (100 μL), and a 4 mol/L solution (21.2 μL) of hydrochloric acid in ethyl acetate was added. The mixture was stirred at room temperature for 1 hour and then diluted with ethyl acetate (500 μL), and precipitates were collected by filtration. The precipitates were washed with ethyl acetate (500 μL) and dried, and thus monohydrochloride crystal Form II (14.4 mg) of Compound (I) was obtained as colorless crystals.

The results of X-ray powder diffraction are shown in FIG. 12 and Table 5. (Measurement conditions: Method A)

TABLE 5

| 2θ |
|---|
| 5.267 |
| 11.278 |
| 17.07 |
| 18.797 |
| 21.665 |
| 23.196 |
| 25.485 |
| 25.774 |
| 26.447 |
| 29.391 |

Diffraction angles of major peaks (2θ) in X-ray powder diffraction spectrum: 11.3°±0.2°, 17.1°±0.2°, 25.5°±0.2°, 25.8°±0.2°, 26.4°±0.2°.

The results of TG/DTA measurement are shown in FIG. 25. The observed onset temperature was about 210.9° C. No weight loss was observed on TG.

The results of the moisture sorption-desorption isothermal measurement are shown in FIG. 48. In the moisture sorption isothermal measurement, the ratio of the increased mass at 95% Target % P/P$_0$ to the mass at 0% Target % P/P$_0$ was about 0.3. In the moisture desorption isothermal measurement, the ratio at 0% Target % P/P$_0$ was about 0.05.

EXAMPLE 5

Synthesis of Monohydrochloride Crystal Form III of Compound (I)

Free base A (50.0 mg) of Compound (I) was dissolved in methanol (50 μL) and ethyl acetate (200 μL), and a 4 mol/L solution (21.2 μL) of hydrochloric acid in ethyl acetate was added. Solids were precipitated immediately thereafter. The mixture was diluted with ethyl acetate (300 μL), and precipitates were collected by filtration. The precipitates were washed with ethyl acetate (500 μL) and dried, and thus monohydrochloride crystal Form III (25.0 mg) of Compound (I) was obtained as pale yellow crystals.

The results of X-ray powder diffraction are shown in FIG. 13 and Table 6. (Measurement conditions: Method A)

TABLE 6

| 2θ |
|---|
| 5.122 |
| 5.598 |
| 9.224 |
| 9.88 |
| 14.358 |
| 15.33 |
| 21.449 |
| 22.573 |
| 23.332 |

Diffraction angles of major peaks (2θ) in X-ray powder diffraction spectrum: 5.1°±0.2°, 9.9°±0.2°, 15.3°±0.2°, 21.4°±0.2°, 23.3°±0.2°.

The results of TG/DTA measurement are shown in FIG. 26. The observed onset temperature was about 223.9° C. No weight loss was observed on TG.

EXAMPLE 6

Synthesis of Monohydrochloride Crystal Form VII of Compound (I)

1,2-Dimethoxyethane (2 mL) was added to monohydrochloride crystal Form VI (10 mg) of Compound (I), the crystal was dissolved under warming, and then cooled with liquid nitrogen, the resulting precipitates were filtered, and thus monohydrochloride crystal Form VII of Compound (I) was obtained as yellow crystals.

The results of X-ray powder diffraction are shown in FIG. 14 and Table 7. (Measurement conditions: Method A)

TABLE 7

| 2θ |
|---|
| 5.686 |
| 7.008 |
| 11.386 |
| 12.328 |
| 15.95 |
| 17.327 |
| 19.1 |
| 21.234 |
| 22.969 |

Diffraction angles of major peaks (2θ) in X-ray powder diffraction spectrum: 7.0°±0.2°, 12.3°±0.2°, 16.0°±0.2°, 19.1°±0.2°, 21.2°±0.2°.

The results of TG/DTA measurement are shown in FIG. 27. The observed onset temperature was about 171.7° C. The weight loss of about 0.31% was observed on TG.

EXAMPLE 7

Synthesis of Monohydrochloride Ethanolate Crystals of Compound (I)

Compound (IIA) (35.27 g, 74.0 mmol), p-toluenesulfonic acid monohydrate (13.41 g, 80.7 mmol), tetrahydrofuran (150 mL), and water (13 mL) were mixed, then Compound 4 (30.00 g, 67.3 mmol) was added, and stirred for 5 hours at 50° C. After being cooled to room temperature, the mixture was concentrated to 126.8 g, the pH was adjusted to 9.5 with an aqueous sodium hydroxide solution, and the mixture was extracted with ethyl acetate (240 mL×2). The extract was concentrated to 81.5 g, ethyl acetate (240 mL) was added, and the mixture was again concentrated to 79.7 g. Moreover, ethyl acetate (240 mL) was added, the mixture was concentrated to 61.6 g, and ethanol (240 mL) was added. The mixture was heated to 60° C., and monohydrochloride crystal Form I (9 mg) obtained in Example 1 was added as seed crystals, then 5.83 mL of concentrated hydrochloric acid was added to precipitate solids. The mixture was stirred at 25° C. for 2 hours and filtered, and thus monohydrochloride ethanolate crystals (36.31 g, 87.8%) of Compound (I) which is different from the seed crystals were obtained.

The results of X-ray powder diffraction are shown in FIG. 15 and Table 8. (Measurement conditions: Method A)

TABLE 8

| 2θ |
|---|
| 7.629 |
| 8.33 |
| 8.909 |
| 12.889 |
| 13.688 |

TABLE 8-continued

| 2θ |
|---|
| 14.716 |
| 21.133 |
| 21.451 |
| 22.965 |
| 23.709 |

Diffraction angles of major peaks (2θ) in X-ray powder diffraction spectrum: 8.3°±0.2°, 8.9°±0.2°, 12.9°±0.2°, 13.7°±0.2°, 14.7°±0.2°.

The results of TG/DTA measurement are shown in FIG. 28. The observed onset temperature was about 231° C. The weight loss of about 1.01% was observed on TG.

EXAMPLE 8

Synthesis of mono-p-toluenesulfonate Crystal Form I of Compound (I)

Using Compound 4 (1.01 g) as a starting material, free base A (1.42 g) synthesized according to Reference Example 1 was purified by silica gel chromatography (chloroform:methanol=100:1 to 95:5), and the fraction of the target product was concentrated under reduced pressure. The residue was dissolved in acetone and concentrated under reduced pressure, and diethyl ether (4 mL) and hexane (1 mL) were added. The resulting solids were filtered and washed with a mixed solution of hexane:diethyl ether (1:1) and hexane, and thus a free base (981 mg) was obtained. Then, 112 mg of the free base was dissolved in ethyl acetate (1 mL), and a 1 mol/L solution (190 μL) of p-toluenesulfonic acid in methanol was added. Ethyl acetate (2 mL) was added, and the mixture was stirred for 1 hour at room temperature. The resulting solids were collected by filtration, washed with ethyl acetate and diethyl ether, and dried, and thus mono-p-toluenesulfonate crystal Form I (136 mg) of Compound (I) was obtained as colorless crystals.

$^1$H-NMR (300 MHz, DMSO-d6) δ 2.29 (6H, s), 3.14-3.30 (2H, m), 3.52-3.81 (3H, m), 3.88-3.89 (1H, m), 4.00-4.08 (1H, m), 4.41 (2H, d, J=5.5 Hz), 5.28 (2H, s), 7.11 (2H, d, J=7.9 Hz), 7.15-7.24 (1H, m), 7.26-7.36 (3H, m), 7.45-7.52 (3H, m), 7.68 (1H, dd, J=8.8, 2.6 Hz), 7.83 (1H, d, J=8.8 Hz), 7.95 (1H, d, J=2.5 Hz), 8.27 (1H, dd, J=8.8, 1.7 Hz), 8.61 (1H, s), 8.77 (1H, d, J=1.7 Hz), 8.90 (1H, s), 10.11 (1H, s).

Elemental analysis:
calculated value: C, 60.69; H, 4.82; Cl, 4.84; F, 2.59; N, 9.56; S, 4.38
measured value: C, 60.45; H, 4.79; Cl, 4.47; F, 2.42; N, 9.46; S, 4.11

The results of X-ray powder diffraction are shown in FIG. 18 and Table 9. (Measurement conditions: Method A)

TABLE 9

| 2θ |
|---|
| 6.096 |
| 6.376 |
| 10.75 |
| 13.744 |
| 15.689 |
| 16.259 |
| 20.049 |
| 22.717 |

TABLE 9-continued

| 2θ |
|---|
| 24.587 |
| 25.347 |

Diffraction angles of major peaks (2θ) in X-ray powder diffraction spectrum: 13.7°±0.2°, 15.7°±0.2°, 20.0°±0.2°, 22.7°±0.2°, 25.3°±0.2°.

The results of TG/DTA measurement are shown in FIG. 31. The observed onset temperature was about 208.5° C. No weight loss was observed on TG.

The results of the moisture sorption-desorption isothermal measurement are shown in FIG. 49. In the moisture sorption isothermal measurement, the ratio of the increased mass at 95% Target % P/P$_0$ to the mass at 0% Target % P/P$_0$ was about 1.4. In the moisture desorption isothermal measurement, the ratio at 0% Target % P/P$_0$ was about 0.12.

EXAMPLE 9

Synthesis of Monosulfate Crystals of Compound (I)

Free base A (50.0 mg) of Compound (I) was dissolved in acetonitrile (400 μL), and a 1 mol/L solution (84.8 μL) of sulfuric acid in methanol was added. Acetonitrile (1 mL) was added, the mixture was stirred at 0° C., and the resulting solids were collected by filtration and washed with cold acetonitrile. Solids were dried, and yellow crystals (15.1 mg) were obtained. These were used as seed crystals.

Free base A (100 mg) of Compound (I) was dissolved in acetonitrile (400 μL), and a 1 mol/L solution (179 μL) of sulfuric acid in methanol and a small amount of the seed crystals prepared above were added. Acetonitrile (1 mL) was added, and the mixture was stirred at 0° C. The resulting solids were collected by filtration, washed with cold acetonitrile, and dried, and thus monosulfate crystals (47.9 mg) of Compound (I) were obtained.

$^1$H-NMR (400 MHz, DMSO-d6) δ 2.30 (3H, s), 3.12-3.24 (1H, m), 3.24-3.32 (1H, m), 3.62-3.90 (3H, m), 3.93 (1H, d, J=11.4 Hz), 4.05 (1H, d, J=11.4 Hz), 4.49-4.52 (2H, m), 5.32 (2H, s), 7.16-7.22 (1H, m), 7.30-7.39 (3H, m), 7.45-7.52 (1H, m), 7.65-7.70 (1H, m), 7.91 (1H, d, J=2.0 Hz), 8.00 (1H, d, J=8.8 Hz), 8.47 (1H, d, J=8.8 Hz), 8.95 (1H, s), 9.28 (1H, s), 9.53 (1H, s), 9.64 (1H, s), 12.11 (1H, s).

Elemental analysis:
calculated value: C, 54.08; H, 4.66; Cl, 5.32; F, 2.85; N, 10.51; S, 4.33 (0.9H$_2$SO$_4$ 1.0H$_2$O)
measured value: C, 54.11; H, 4.78; Cl, 5.68; F, 2.65; N, 10.06; S, 4.32

The results of X-ray powder diffraction are shown in FIG. 19 and Table 10. (Measurement conditions: Method A)

TABLE 10

| 2θ |
|---|
| 6.202 |
| 12.065 |
| 13.963 |
| 14.459 |
| 15.894 |
| 16.168 |
| 16.785 |
| 21.032 |
| 22.889 |
| 26.89 |

Diffraction angles of major peaks (2θ) in X-ray powder diffraction spectrum: 6.2°±0.2°, 14.0°±0.2°, 14.5°±0.2°, 16.8°±0.2°, 22.9°±0.2°.

The results of TG/DTA measurement are shown in FIG. 32. The observed onset temperature was about 190.5° C. No weight loss was observed on TG.

The results of the moisture sorption-desorption isothermal measurement are shown in FIG. 50. In the moisture sorption isothermal measurement, the ratio of the increased mass at 95% Target % $P/P_0$ to the mass at 0% Target % $P/P_0$ was about 3.3. In the moisture desorption isothermal measurement, the ratio at 0% Target % $P/P_0$ was about 0.13.

EXAMPLE 10

Synthesis of Monosulfate Monohydrate Crystals of Compound (I)

Trihydrate crystals (3 mg) of the free base of Compound (I) produced by the method described in Reference Example 5 were dissolved in a mixed solution (0.15 mL) of acetonitrile:2-propanol (1:1), 0.1 mol/L sulfuric acid (0.056 mL) was added, and then the mixture was concentrated under reduced pressure. A mixed solution (0.3 mL) of methanol:water (95:5) was added, the mixture was shaken at 15° C. for 1 hour and then concentrated under reduced pressure, and thus monosulfate monohydrate crystals of Compound (I) were obtained.

The results of X-ray powder diffraction are shown in FIG. 20 and Table 11. (Measurement conditions: Method A)

TABLE 11

| 2θ |
|---|
| 5.01 |
| 7.365 |
| 9.937 |
| 10.127 |
| 13.789 |
| 14.659 |
| 16.986 |
| 21.401 |

Diffraction angles of major peaks (2θ) in X-ray powder diffraction spectrum: 5.0°±0.2°, 9.9°±0.2°, 13.8°±0.2°, 14.7°±0.2°, 17.0°±0.2°.

The results of TG/DTA measurement are shown in FIG. 33. The weight loss of about 4.49% was observed on TG.

EXAMPLE 11

Synthesis of Monophosphate Crystals of Compound (I)

Trihydrate crystals (3 mg) of the free base of Compound (I) were dissolved in a mixed solution (0.15 mL) of acetonitrile:2-propanol (1:1), 0.1 mol/L phosphoric acid (0.056 mL) was added, and then the mixture was concentrated under reduced pressure. A mixed solution (0.3 mL) of ethanol:water (95:5) was added, the mixture was shaken at 15° C. for 1 hour and then concentrated under reduced pressure, and thus monophosphate crystals of Compound (I) were obtained.

The results of X-ray powder diffraction are shown in FIG. 21 and Table 12. (Measurement conditions: Method A)

TABLE 12

| 2θ |
|---|
| 5.139 |
| 6.205 |

TABLE 12-continued

| 2θ |
|---|
| 6.688 |
| 9.829 |
| 12.294 |
| 13.315 |
| 16.566 |
| 21.091 |

Diffraction angles of major peaks (2θ) in X-ray powder diffraction spectrum: 5.1°±0.2°, 6.2°±0.2°, 6.7°±0.2°, 9.8°±0.2°, 12.3°±0.2°.

The results of TG/DTA measurement are shown in FIG. 34. The observed onset temperature was about 188.1° C. The weight loss of about 1.76% was observed on TG.

EXAMPLE 12

Synthesis of Monophosphate Dihydrate Crystal Form I of Compound (I)

Trihydrate crystals (3 mg) of the free base of Compound (I) were dissolved in a mixed solution (0.15 mL) of acetonitrile:2-propanol (1:1), 0.1 mol/L of phosphoric acid (0.056 mL) was added, and then the mixture was concentrated under reduced pressure. A mixed solution (0.3 mL) of methanol:water (95:5) was added, the mixture was shaken at 15° C. for 1 hour and then concentrated under reduced pressure, and thus monophosphate dihydrate crystal Form I of Compound (I) was obtained.

The results of X-ray powder diffraction are shown in FIG. 22 and Table 13. (Measurement conditions: Method A)

TABLE 13

| 2θ |
|---|
| 5.071 |
| 6.518 |
| 9.625 |
| 10.047 |
| 11.934 |
| 12.177 |
| 12.937 |
| 16.866 |
| 18.625 |

Diffraction angles of major peaks (2θ) in X-ray powder diffraction spectrum: 5.1°±0.2°, 6.5°±0.2°, 9.6°±0.2°, 12.9°±0.2°, 18.6°±0.2°.

The results of TG/DTA measurement are shown in FIG. 35. No weight loss was observed on TG.

EXAMPLE 13

Synthesis of Monofumarate Crystal Form I of Compound (I)

Trihydrate crystals (3 mg) of the free base of Compound (I) were dissolved in a mixed solution (0.15 mL) of acetonitrile:2-propanol (1:1), a 0.1 mol/L solution (0.056 mL) of fumaric acid in methanol:water (1:1) was added, and then the mixture was concentrated under reduced pressure. A mixed solution (0.3 mL) of methanol:water (95:5) was added, the mixture was shaken at 15° C. for 1 hour and then concentrated under reduced pressure, and thus monofumarate crystal Form I of Compound (I) was obtained.

The results of X-ray powder diffraction are shown in FIG. 23 and Table 14. (Measurement conditions: Method A)

TABLE 14

| 2θ |
|---|
| 5.443 |
| 5.971 |
| 7.984 |
| 9.058 |
| 10.043 |
| 12.306 |
| 14.752 |
| 16.131 |
| 19.511 |
| 19.864 |

Diffraction angles of major peaks (2θ) in X-ray powder diffraction spectrum: 8.0°±0.2°, 9.1°±0.2°, 16.1°±0.2°, 19.5°±0.2°, 19.9°±0.2°.

The results of TG/DTA measurement are shown in FIG. 36. The observed onset temperature was about 191.3° C. No weight loss was observed on TG.

EXAMPLE 14

Synthesis of Monofumarate Crystal Form II of Compound (I)

Trihydrate crystals (3 mg) of the free base of Compound (I) were dissolved in a mixed solution (0.15 mL) of acetonitrile:2-propanol (1:1), a 0.1 mol/L solution (0.056 mL) of fumaric acid in methanol:water (1:1) was added, and then the mixture was concentrated under reduced pressure. A mixed solution (0.3 mL) of acetonitrile:water (95:5) was added, the mixture was shaken at 15° C. for 1 hour and then concentrated under reduced pressure, and thus monofumarate crystal Form II of Compound (I) was obtained.

The results of X-ray powder diffraction are shown in FIG. 24 and Table 15. (Measurement conditions: Method A)

TABLE 15

| 2θ |
|---|
| 5.444 |
| 8.031 |
| 9.065 |
| 13.304 |
| 13.717 |
| 16.429 |
| 17.112 |
| 18.051 |
| 19.886 |
| 21.834 |

Diffraction angles of major peaks (2θ) in X-ray powder diffraction spectrum: 5.4°±0.2°, 9.1°±0.2°, 13.3°±0.2°, 13.7°±0.2°, 18.1°±0.2°.

The results of TG/DTA measurement are shown in FIG. 37. The observed onset temperature was about 195.6° C. The weight loss of about 1.42% was observed on TG.

REFERENCE EXAMPLE 3

Synthesis of Free Base Crystals of Compound (I)

Free base B (50.0 mg) of Compound (I) was suspended in hexane (1 mL) and ethyl acetate (0.7 mL) and dissolved under warming. The mixture was left to stand at room temperature, then the resulting solids were collected by filtration and dried, and thus free base crystals (39.9 mg) of Formula (I) were obtained as colorless crystals.

$^1$H-NMR (400 MHz, DMSO-d6) δ 2.28 (3H, s), 2.74-2.83 (2H, m), 3.09-3.30 (3H, m), 3.68 (1H, d, J=10.6 Hz), 3.82 (1H, d, J=10.6 Hz), 4.10-4.22 (2H, m), 5.28 (2H, s), 7.19 (1H, t, J=8.2 Hz), 7.25-7.38 (3H, m), 7.45-7.52 (1H, m), 7.71 (1H, d, J=8.8 Hz), 7.81 (1H, d, J=8.8 Hz), 7.99 (1H, s), 8.22 (1H, d, J=8.8 Hz), 8.61 (1H, s), 8.76 (1H, s).

The results of X-ray powder diffraction are shown in FIG. 44 and Table 16. (Measurement conditions: Method A)

TABLE 16

| 2θ |
|---|
| 5.428 |
| 13.891 |
| 16.224 |
| 17.18 |
| 19.513 |
| 20.383 |
| 23.334 |
| 23.628 |
| 24.939 |
| 28.012 |

Diffraction angles of major peaks (2θ) in x-ray powder diffraction spectrum: 5.4°±0.2°, 13.9°±0.2°, 17.2°±0.2°, 20.4°±0.2°, 24.9°±0.2°.

The results of TG/DTA measurement are shown in FIG. 51. The observed onset temperature was about 134.1° C. No weight loss was observed on TG.

The results of the moisture sorption-desorption isothermal measurement are shown in FIG. 52. In the moisture sorption isothermal measurement, the ratio of the increased mass at 95% Target % P/P$_0$ to the mass at 0% Target % P/P$_0$ was about 1.0. In the moisture desorption isothermal measurement, the ratio at 0% Target % P/P$_0$ was about 0.16.

REFERENCE EXAMPLE 4

Synthesis of Monohydrate Crystals of Free Base of Compound (I)

Seed crystals of Free base of Compound (I) were added to the ethyl acetate extract of Example 25 while being stirred at 15° C. until the crystals did not dissolve any more. Large amounts of precipitated crystals were collected by filtration, and thus monohydrate crystals of the free base of Compound (I) were obtained.

Moisture value: 3.23% (Theoretical value of monohydrate: 3.12%)

The results of X-ray powder diffraction are shown in FIG. 16 and Table 17. (Measurement conditions: Method A)

TABLE 17

| 2θ |
|---|
| 6.045 |
| 8.307 |
| 11.758 |
| 12.097 |
| 16.61 |
| 20.056 |
| 25.487 |
| 26.087 |
| 27.368 |

Diffraction angles of major peaks (2θ) in X-ray powder diffraction spectrum: 6.0°±0.2°, 8.3°±0.2°, 20.1°±0.2°, 25.5°±0.2°, 26.1°±0.2°.

The results of TG/DTA measurement are shown in FIG. 29. The weight loss of about 2.27% was observed on TG.

REFERENCE EXAMPLE 5

Synthesis of Trihydrate Crystals of Free Base of Compound (I)

Crystals precipitated when concentrating the extract of Example 25 were collected by filtration and subjected to through-flow drying, and thus trihydrate crystals of the free base of Compound (I) were obtained.
Moisture value: 9.87% (Theoretical value of trihydrate: 8.8%)
The results of X-ray powder diffraction are shown in FIG. 17 and Table 18. (Measurement conditions: Method A)

TABLE 18

| 2θ |
|---|
| 5.919 |
| 8.735 |
| 10.92 |
| 11.742 |
| 13.811 |
| 21.249 |
| 23.55 |
| 24.689 |
| 25.4 |
| 27.297 |

Diffraction angles of major peaks (2θ) in X-ray powder diffraction spectrum: 5.9°±0.2°, 8.7°±0.2°, 10.9°±0.2°, 24.7°±0.2°, 25.4°±0.2°.
The results of TG/DTA measurement are shown in FIG. 30. The weight loss of about 11.2% was observed on TG.

REFERENCE EXAMPLE 6

Synthesis of Dihydrochloride Crystals of Compound (I)

First, to 16 g of the ethanol solution (about 400 g) containing the free base (about 50 g) of Compound (I), the monohydrochloride crystal Form I (2.5 mg) obtained in Example 1 was added, and then 0.838 g (2.5 eq) of concentrated hydrochloric acid was added. The mixture was stirred for 2 hours, then the precipitated solids were collected by filtration, and thus dihydrochloride crystals of Compound (I) were obtained.
Elemental analysis:
  calculated value: C, 57.59; H, 4.64; Cl, 15.87; F, 3.04; N, 11.19 (1.8HCl salt)
  measured value: C, 57.99; H, 5.51; Cl, 16.74; F, 2.86; N, 11.47
The results of X-ray powder diffraction are shown in FIG. 38. (Measurement conditions: Method A)

REFERENCE EXAMPLE 7

Synthesis of mono-p-toluenesulfonate Crystal Form II of Compound (I)

Free base A (50.0 mg) of Compound (I) was dissolved in acetonitrile (500 μL), and a 1 mol/L solution (84.8 μL) of p-toluenesulfonic acid in methanol was added. The mixture was stirred at room temperature for 2 hours, acetonitrile (500 μL) was added, the mixture was further stirred for 1 hour and diluted with ethyl acetate, and the resulting solids were collected by filtration. The solids were dried, and thus mono-p-toluenesulfonate crystal Form II (29.7 mg) of Compound (I) was obtained as colorless crystals.
The results of X-ray powder diffraction are shown in FIG. 39. (Measurement conditions: Method A)

REFERENCE EXAMPLE 8

Synthesis of Monobenzenesulfonate Crystals of Compound (I)

Trihydrate crystals (3 mg) of the free base of Compound (I) were dissolved in a mixed solution (0.15 mL) of acetonitrile:2-propanol (1:1), a 0.1 mol/L aqueous solution (0.056 mL) of benzenesulfonic acid was added, and then the mixture was concentrated under reduced pressure. A mixed solution (0.3 mL) of methanol:water (95:5) was added, the mixture was shaken at 15° C. for 1 hour and then concentrated under reduced pressure, and thus monobenzenesulfonate crystals of Compound (I) were obtained.
The results of X-ray powder diffraction are shown in FIG. 40. (Measurement conditions: Method A)

REFERENCE EXAMPLE 9

Synthesis of Monophosphate Dihydrate Crystal Form II of Compound (I)

Trihydrate crystals (3 mg) of the free base of Compound (I) were dissolved in a mixed solution (0.15 mL) of acetonitrile:2-propanol (1:1), 0.1 mol/L phosphoric acid (0.056 mL) was added, and then the mixture was concentrated under reduced pressure. A mixed solution (0.3 mL) of methyl acetate:water (95:5) was added, the mixture was shaken at 15° C. for 1 hour and then concentrated under reduced pressure, and thus monophosphate dihydrate crystal Form II of Compound (I) was obtained.
The results of X-ray powder diffraction are shown in FIG. 41. (Measurement conditions: Method A)

REFERENCE EXAMPLE 10

Synthesis of Monocitrate Crystals of Compound (I)

Trihydrate crystals (3 mg) of the free base of Compound (I) were dissolved in a mixed solution (0.15 mL) of acetonitrile:2-propanol (1:1), a 0.1 mol/L aqueous solution (0.056 mL) of citric acid was added, and then the mixture was concentrated under reduced pressure. A mixed solution (0.3 mL) of methanol:water (95:5) was added, the mixture was shaken at 15° C. for 1 hour and then concentrated under reduced pressure, and thus monocitrate crystals of Compound (I) were obtained.
The results of X-ray powder diffraction are shown in FIG. 42. (Measurement conditions: Method A)

REFERENCE EXAMPLE 11

Synthesis of Monotartrate Crystals of Compound (I)

Trihydrate crystals (3 mg) of the free base of Compound (I) were dissolved in a mixed solution (0.15 mL) of acetonitrile:2-propanol (1:1), a 0.1 mol/L aqueous solution (0.056 mL) of tartaric acid was added, and then the mixture was concentrated under reduced pressure. A mixed solution (0.3 mL) of methanol:water (95:5) was added, the mixture was shaken at 15° C. for 1 hour and then concentrated under reduced pressure, and thus monotartarate crystals of Compound (I) were obtained.

The results of X-ray powder diffraction are shown in FIG. 43. (Measurement conditions: Method A)

EXAMPLE 15

(Results of XRPD Measurement)

A compound having a structure similar to that of Compound (I) of the present application is disclosed as Compound (VI-1) in Example 2 of Patent Document 2. Compound (VI-1) is described as being obtained as dihydrochloride crystals.

[Chemical Formula 24]

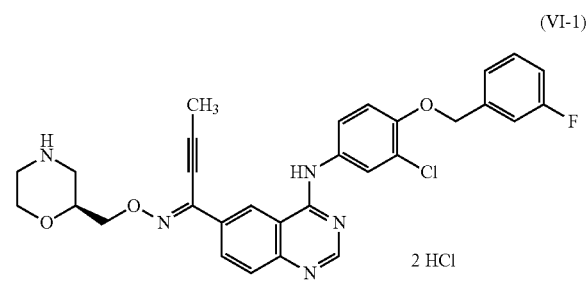

(VI-1)

2 HCl

Next, the pKa values of nitrogen atoms having basicity of the free bases of Compound (VI-1) described in Patent Document 2 and Compound (I) described in the present application are shown. In order to calculate the pKa values, ACD/Labs (Technical Computing Solution ACD/Labs, by Fujitsu) was used.

[Chemical Formula 25]

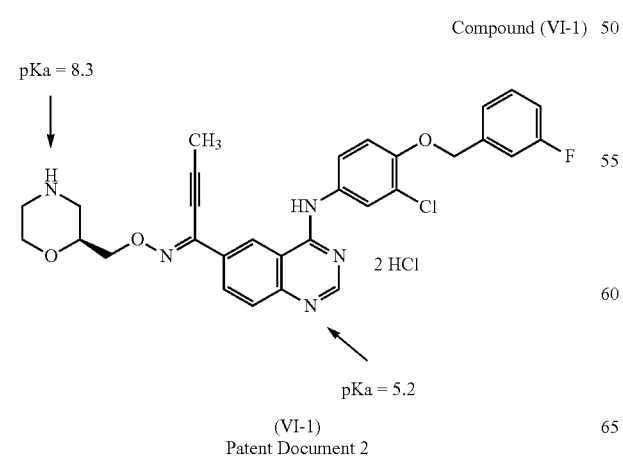

Compound (VI-1)
pKa = 8.3

2 HCl pKa = 5.2

(VI-1)
Patent Document 2

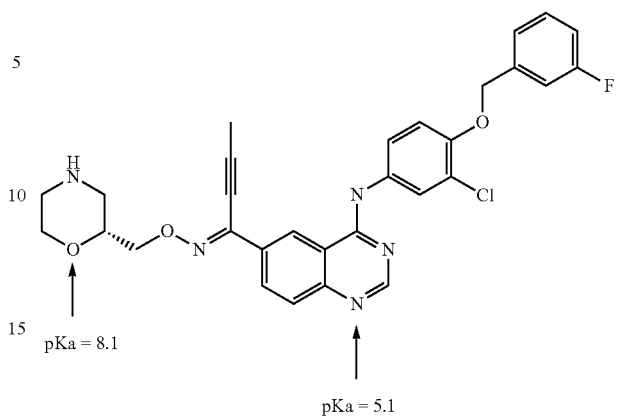

Free base of Compound (I)

pKa = 8.1 pKa = 5.1

As is clear from above, the respective pKa values of the basic nitrogen atoms of the morpholine moieties and the basic nitrogen atoms of the quinazoline moieties show nearly the same values.

Generally, it is said that a salt can be formed when the difference between the pKa values of a base and a counter (for example, hydrochloric acid) is 3 or greater. Since hydrochloric acid has a pKa value of −6, the free base of Compound (I) described in the present application can also form dihydrochloride (References; Recent Progress in Physicochemical Characterization and Formulation Technologies for Poorly Soluble Drugs, 2010, pp. 111-121; Structure, solubility, screening, and synthesis of molecular salts, JOURNAL OF PHARMACEUTICAL SCIENCES, VOL. 96, NO. 5, MAY 2007).

Here, dihydrochloride crystals of Compound (I) prepared according to Reference Example 6 exhibited a broad peak as shown in FIG. 38, and it was thus found that dihydrochloride crystals of Compound (I) have low crystallinity.

In general, low crystallinity crystals are known to have poor physical stability, poor chemical stability, and such features, and it is said that the handling of such an active pharmaceutical ingredient is difficult (Reference; Recent Progress in Physicochemical Characterization and Formulation Technologies for Poorly Soluble Drugs, 2010, pp. 215-216). For example, in the case of using low crystallinity crystals as an active ingredient, they may transition to crystals that have good crystallinity when synthesis is carried out in a large scale. Also, due to poor stability, they are not suitable for long-term storage.

Various crystals of monohydrochloride of Compound (I) described in Examples 1 to 7 are crystals having good crystallinity as shown in FIGS. 1 to 3 and FIGS. 12 to 15, and it is an unexpected effect that forming Compound (I) into monohydrochloride provides crystal polymorphs suitable for an active pharmaceutical ingredient.

Also, it was found that mono-p-toluenesulfonate crystal Form II, monobenzenesulfonate crystals, monophosphate dihydrate crystal Form II, monocitrate crystals, and monotartrate crystals of Compound (I) described in Reference Examples 7 to 11 exhibit broad peaks as shown in FIGS. 39 to 43 and have low crystallinity.

From above, it was found that only low crystallinity crystals were obtained from not only dihydrochloride of Compound (I) but also some of the salts obtained by addition of one acid molecule but, on the other hand, monohydrochloride crystals of Compound (I) in any crystal form have good crystallinity and are in crystal forms suitable for use as an active pharmaceutical ingredient of a drug.

EXAMPLE 16

(Test of Solubility in Water for Injection)
1. Preparation of Calibration Curve

First, 5 mg of monohydrochloride crystal Form I of Compound (I) was precisely weighed and dissolved in a mixed solution of acetonitrile:water (1:1), and thus a 500 µg/mL solution was obtained. The obtained solution was diluted with a mixed solution of acetonitrile:water (1:1) such that the concentrations of the compound were 5 and 50 µg/mL. Accordingly, a standard calibration curve was prepared according to HPLC measurement conditions (Method A). The same operation was carried out for monohydrochloride crystal Form II, monohydrochloride crystal Form V, monohydrochloride crystal Form VI, mono-p-toluenesulfonate crystal Form I, and free base crystals.

2. Preparation of Sample Solution

First, 1 mg of monohydrochloride crystal Form I of Compound (I) was precisely weighed and transferred to a vial having a volume of 4 mL. Then, 1 mL of water (water for injection) was added, and the mixture was stirred at 37° C. for 1 hour. After being stirred, this suspension was filtered, and the peak area was measured under HPLC measurement conditions (Method A) using a solution obtained by diluting the filtrate two-fold with a mixed solution of acetonitrile:water (1:1) as a sample. The concentration was calculated using the peak area and the calibration curve prepared above. The same operation was carried out for monohydrochloride crystal Form II, monohydrochloride crystal Form V, monohydrochloride crystal Form VI, mono-p-toluenesulfonate crystal Form I, and free base crystals.

(Results)

The respective solubilities of the monohydrochloride crystal Form I, monohydrochloride crystal Form II, monohydrochloride crystal Form V, monohydrochloride crystal Form VI, mono-p-toluenesulfonate crystal Form I, and free base crystals of Compound (I) in water for injection are shown in Table 19.

In general, the solubility of a pharmaceutical agent is deeply involved in disposition, and an active pharmaceutical ingredient is desired to have high solubility. Accordingly, it was found that the monohydrochloride crystal Form I, monohydrochloride crystal Form II, monohydrochloride crystal Form V, monohydrochloride crystal Form VI, and mono-p-toluenesulfonate crystal Form I of Compound (I) have high solubilities, and are in crystal forms suitable for use as an active pharmaceutical ingredient of a drug.

EXAMPLE 17

(Test of Solubility in Organic Solvent)

The monohydrochloride crystal Form I, monohydrochloride crystal Form V, and free base crystals of Compound (I) were each suspended in 2-propanol, acetone, and ethyl acetate, and stirred at 22° C. for 4 hours, and the concentrations of supernatants were measured (HPLC: Method B).
(Results) Solubilities in 2-propanol, acetone, and ethyl acetate are shown in Table 20.

TABLE 20

| Sample | Concentration (% by weight) | | |
| --- | --- | --- | --- |
|  | 2-Propanol | Acetone | Ethyl acetate |
| Monohydrochloride crystal Form I | 0.03 | 0.08 | 0.01 |
| Monohydrochloride crystal Form V | 0.01 | 0.02 | 0.00 |
| Free base crystal | 0.49 | 8.1 | 3.3 |

As is clear from Table 20, it can be understood that the concentrations (% by weight) of the free base crystals of Compound (I) in various organic solvents are high (about 0.5% by weight to about 8% by weight), showing high solubility, but, on the other hand, the monohydrochloride crystal Form I and the monohydrochloride crystal Form V of Compound (I) barely dissolve in various organic solvents (both 0.1% by weight or less). That is to say, when synthesizing Compound (I) as described in Reference Example 1 above or Example 18 or 25 below, if the produced Compound (I) has high solubility in organic solvents, the ratio of the product precipitated from organic solvents is small, and the yield is reduced. Accordingly, it was found that the monohydrochloride crystal Form I and the monohydrochloride crystal Form V of Compound (I) are in crystal forms suitable for use as an active pharmaceutical ingredient of a drug.

TABLE 19

|  | Free base crystal | Monohydrochloride crystal Form I | Monohydrochloride crystal Form II | Monohydrochloride crystal Form V | Monohydrochloride crystal Form VI | Mono-p-toluenesulfonate crystal Form I |
| --- | --- | --- | --- | --- | --- | --- |
| Water for injection | N.D. | 34.5 | 56.0 | 14.0 | 12.9 | 26.6 |

(N.D.: Not Detected, Unit: µg/mL)

As is clear from the above table, the free base crystals of Compound (I) was not dissolved in water for injection at all but, on the other hand, the monohydrochloride crystal Form I, monohydrochloride crystal Form II, monohydrochloride crystal Form V, monohydrochloride crystal Form VI, and mono-p-toluenesulfonate crystal Form I of Compound (I) showed high solubilities in water for injection.

EXAMPLE 18

(Purification Effect by Crystallization)

Purification effects of the free base crystals, monohydrochloride crystal Form I, and monohydrochloride crystal Form VI of Compound (I) crystallized from an ethyl acetate solution of Compound (I) were compared respectively.

[Chemical Formula 26]

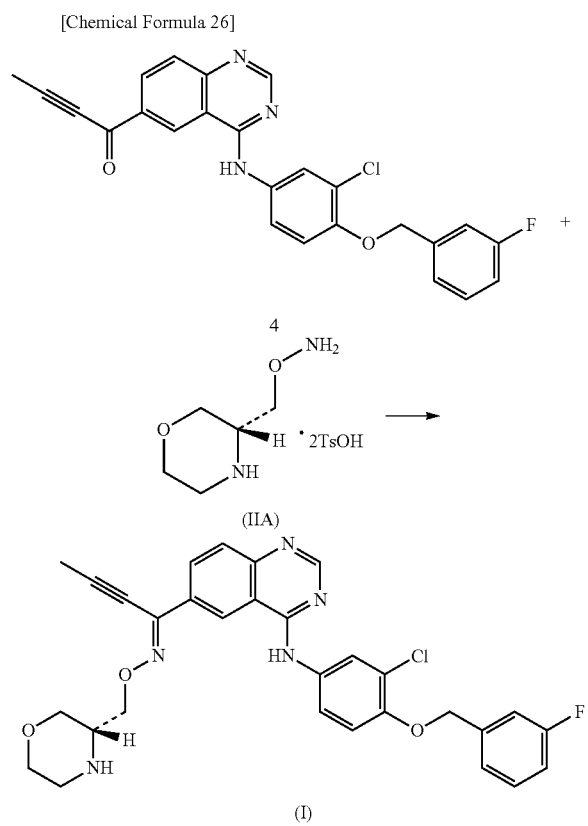

(Step 1) Synthesis of Ethyl Acetate Solution of Compound (I)

Compound 4 (30.04 g, 67.4 mmol) was dissolved in N-methylpyrrolidone (70.86 g) and tetrahydrofuran (18.68 g), added to a slurry of Compound (IIA) (36.85 g, 77.3 mmol), p-toluenesulfonic acid monohydrate (15.37 g, 80.8 mmol), tetrahydrofuran (53.41 g), and water (5.40 g), and stirred at 57° C. for 5 hours. After the mixture was cooled to room temperature, Compound 4 (0.25 g) was added. Thereafter, the pH was adjusted to 9.0 with an aqueous sodium hydroxide solution, followed by extraction with ethyl acetate (651.52 g). The extract was concentrated to 107.39 g, ethyl acetate (162.40 g) was added, and thus an ethyl acetate solution (269.76 g) of Compound (I) was obtained.

(Step 2-1) Synthesis of Free Base Crystals of Compound (I)

The ethyl acetate solution (89.92 g) of Compound (I) was concentrated to 22.97 g, heptane (17.67 g) and ethyl acetate (13.27 g) were added, then the mixture was heated to 60° C., and thus solids were precipitated. Ethyl acetate (12.31 g) was added, the mixture was cooled to room temperature, heptane (41.26 g) and ethyl acetate (6.0 g) were added, and the mixture was concentrated to 49.70 g. Heptane (49.83 g) and ethyl acetate (27.0 g) were added, the mixture was left to stand overnight and then filtered, and thus free base crystals (10.91 g, 86.7%) of Compound (I) were obtained.

(Step 2-2) Synthesis of Monohydrochloride Crystal Form I of Compound (I)

Water (0.13 g) and 2-propanol (16.26 g) were added to the ethyl acetate solution (40.72 g) of Compound (I), and the mixture was heated to 45° C. Seed crystals (225.7 mg) of crystal Form I was added, and then the pH was adjusted to 4.07 with 35% hydrochloric acid. The mixture was stirred at 25° C. for about 30 minutes and then filtered, and thus monohydrochloride crystal Form I (5.50 g, 90.6%) of Compound (I) was obtained.

(Step 2-3) Synthesis of Monohydrochloride Crystal Form VI of Compound (I)

2-Propanol (7.85 g) was added to the ethyl acetate solution (45.20 g) of Compound (I), and the mixture was heated to 60° C. The pH was adjusted to 3.5 with 35% hydrochloric acid, then the mixture was stirred at 25° C. for about 30 minutes and filtered, and thus monohydrochloride crystal Form VI (5.84 g, 86.7%) of Compound (I) was obtained.

The qualities of the free base crystals, monohydrochloride crystal Form I, and monohydrochloride crystal Form VI of Compound (I) obtained by the above synthesis methods were evaluated using HPLC (HPLC: Method B).

TABLE 21

| Sample | Retention time | | | | |
|---|---|---|---|---|---|
| | Impurity A 20 min | Impurity B 21 min | E isomer 38 min | Compound (I) 44 min | Impurity C 62 min |
| Pre-crystallization solution (Ethyl acetate solution) | 0.31 | 0.12 | 6.26 | 89.38 | 0.74 |
| Free base crystal | 0.12 | 0.05 | 1.29 | 97.81 | 0.67 |
| Monohydrochloride crystal Form I | 0.16 | 0.03 | 1.00 | 98.44 | 0.27 |
| Monohydrochloride crystal Form VI | 0.02 | N.D. | 0.80 | 99.17 | N.D. |

(N.D.: Not Detected, Unit: Area %)

When the purities of the respective crystals obtained above are compared, as is clear from Table 21, it can be understood that in order of monohydrochloride crystal Form VI, monohydrochloride crystal Form I, and free base crystals, the ratio of the peak area% of Compound (I) is larger (about 99.2%, about 98.4%, and about 97.8%, respectively), and the amount of various impurities contained is smaller. Accordingly, it was found that when performing crystallization from a pre-crystallization solution (an ethyl acetate solution) containing large amounts of impurities, it is possible to remove various impurities and obtain crystals having a higher purity by obtaining crystals as monohydrochloride crystal Form VI or monohydrochloride crystal Form I than obtaining crystals as free base crystals.

In general, for crystals containing large amounts of impurities, it is necessary to repeat the recrystallization step to increase the purity of the crystals. When the recrystallization step is repeated, the amount of crystals elute into the mother liquor is increased, thus resulting in a reduced yield. Depending on the impurity, the ratio of the impurity removed by the recrystallization step is small, and therefore it is often the case that the purity cannot be increased by repeating the recrystallization step a practical number of times.

Accordingly, it can be said that the monohydrochloride crystal Form VI and the monohydrochloride crystal Form I of Compound (I) are in crystal forms suitable for scale-up synthesis because high-purity crystals can be obtained by single crystallization. That is to say, it was found that the monohydrochloride crystal Form VI and the monohydrochloride crystal Form I of Compound (I) are in crystal forms suitable for use as an active pharmaceutical ingredient of a drug.

EXAMPLE 19

(Water Sorption-Desorption Isothermal Measurement)

Table 22 shows the ratios of increased moisture mass of the monohydrochloride crystal Form I, monohydrochloride crystal Form V, monohydrochloride crystal Form VI, free base crystals, mono-p-toluenesulfonate crystals, and monosulfate crystals of Compound (I).

TABLE 22

| | Ratio of increased mass |
|---|---|
| Monohydrochloride crystal Form I | About 0.8% |
| Monohydrochloride crystal Form II | About 0.3% |
| Monohydrochloride crystal Form V | About 1.7% |
| Monohydrochloride crystal Form VI | About 0.5% |
| Mono-p-toluenesulfonate crystal Form I | About 1.4% |
| Free base crystal | About 1.0% |
| Monosulfate crystal | About 3.3% |

As is clear from Table 22, it was found that the monosulfate crystals of Compound (I) exhibited a moisture increase of about 3.3% but, on the other hand, the ratios of moisture increase of the monohydrochloride crystal Form I, monohydrochloride crystal Form II, monohydrochloride crystal Form V, monohydrochloride crystal Form VI, and mono-p-toluenesulfonate crystal Form I of compound (I) were small.

In general, it is considered that salt crystals are more likely to be influenced by moisture absorption, and absorptivity is said to vary depending on the type of salt (Reference: Recent Progress in Physicochemical Characterization and Formulation Technologies for Poorly Soluble Drugs, 2010, pp. 117-118). Also, crystals that are likely to adsorb water undergo deliquescence and like a phenomenon, and it is difficult to handle such crystals. Moreover, such crystals are not suitable for long-term storage and are rarely selected as an active pharmaceutical ingredient. Accordingly, it was found that the monohydrochloride crystal Form I, monohydrochloride crystal Form II, monohydrochloride crystal Form V, monohydrochloride crystal Form VI, and mono-p-toluenesulfonate crystal Form I of Compound (I) are in crystal forms suitable for use as an active pharmaceutical ingredient of a drug because the ratios of moisture increase are small.

EXAMPLE 20

(Light Exposure Test)

Table 23 shows the results of a light exposure test of the monohydrochloride crystal Form I, monohydrochloride crystal Form II, monohydrochloride crystal Form V, monohydrochloride crystal form VI, and mono-p-toluenesulfonate crystal Form I of Compound (I). The quality evaluations of the respective crystals were carried out using HPLC (Method B).

TABLE 23

| | E isomer (Retention time 38 minutes)* | | |
|---|---|---|---|
| Sample | Dark control | Light exposed sample | Increased amount |
| Monohydrochloride crystal Form I | 0.63 | 4.41 | 3.78 |
| Monohydrochloride crystal Form II | 1.44 | 1.21 | −0.23 |
| Monohydrochloride form crystal V | 0.13 | 1.19 | 1.06 |
| Monohydrochloride form crystal VI | 1.16 | 1.80 | 0.64 |
| Free base crystal | N.D. | 2.59 | 2.59 |
| Mono-p-toluenesulfonate crystal Form I | 0.10 | 32.86 | 32.76 |

(The unit is area %. *Concerning other peaks, changes due to light exposure are barely recognized.)

As shown in Table 23, when the monohydrochloride crystal Form I, monohydrochloride crystal Form II, monohydrochloride crystal Form V, and monohydrochloride crystal Form VI of Compound (I) were subjected to a light exposure test, conversion from a Z isomer to an E isomer was barely observed, or an increase was only as much as about 3.8%. On the other hand, it was found that the photostability of the mono-p-toluenesulfonate crystal Form I of Compound (I) is poor because the E isomer was increased about 33% after light exposure.

In general, crystals having poor photostability undergo decomposition and like a phenomenon due to light, and unacceptable changes may occur due to light exposure. Also, such crystals require utmost attention to the storage method, and it is difficult to handle such crystals.

Accordingly, it was found that the monohydrochloride crystal Form I, monohydrochloride crystal Form II, monohydrochloride crystal Form V, and monohydrochloride crystal Form VI of Compound (I) are in crystal forms suitable for use as an active pharmaceutical ingredient of a drug because light stability under light exposure conditions is good.

EXAMPLE 21

Synthesis of Compound (IIA)

[Chemical Formula 27]

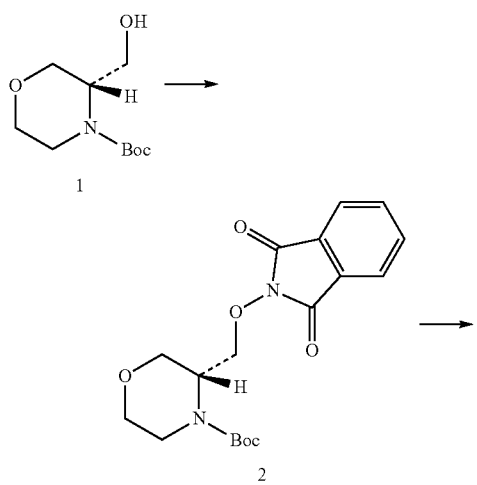

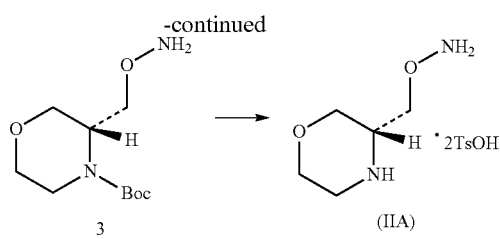

Triphenylphosphine (20.3 g, 77.3 mmol), diisopropyl azodicarboxylate (16.6 g, 81.8 mmol), Compound 1 (14.0 g, 64.4 mmol), and N-hydroxyphthalimide (4.2 g, 70.9 mmol) were stirred at 5 to 15° C. for 2 hours in tetrahydrofuran (98 mL) and toluene (77 mL), and thus a preparation solution for Compound 2 was obtained. A 35% aqueous monomethyl-hydrazine solution (9.3 g, 70.9 mmol) was added thereto, the mixture was stirred at 15° C. for 2 hours, and thus a preparation solution for Compound 3 was obtained. The preparation solution for Compound 3 was concentrated to 114 g and stirred at 0° C. for 2 hours. Precipitated insoluble material was filtered, and toluene (56 mL) was added to the filtrate. This toluene solution was added to a solution of p-toluenesulfonic acid monohydrate (28.2 g, 148.1 mmol) in tetrahydrofuran (42 mL), and the mixture was stirred at 50° C. for 2 hours. Moreover, the mixture was cooled to 0° C., stirred for 2 hours, and filtered, and thus compound (IIA) (27.2 g, yield 88.4%) was obtained.

$^1$H-NMR (CD$_3$OD) δ: 7.67-7.73 (4H, m), 7.20-7.26 (4H, m), 4.92 (5H, bs), 4.30-4.34 (2H, m), 3.91-4.03 (2H, m), 3.63-3.79 (3H, m), 3.18-3.38 (2H, m), 2.36 (6H, s).

The results of X-ray powder diffraction are shown in FIG. 10 and Table 24. (Measurement conditions: Method A)

TABLE 24

| 2θ |
|---|
| 6.396 |
| 7.256 |
| 11.427 |
| 15.232 |
| 17.646 |
| 20.135 |
| 21.05 |
| 21.748 |
| 24.72 |
| 25.315 |

Diffraction angles of major peaks (2θ) in X-ray powder diffraction spectrum: 6.4°±0.2°, 7.3°±0.2°, 21.1°±0.2°, 24.7°±0.2°, 25.3°±0.2°.

EXAMPLE 22

Compound (IIA) (31.2 mg) was left to stand in a high humidity environment, and thus dihydrate (33.8 mg) of Compound (IIA) was obtained.

The results of X-ray powder diffraction are shown in FIG. 11 and Table 25. (Measurement conditions: Method A)

TABLE 25

| 2θ |
|---|
| 7.315 |
| 17.043 |
| 18.451 |
| 19.701 |

TABLE 25-continued

| 2θ |
|---|
| 21.702 |
| 22.578 |
| 22.804 |
| 24.024 |
| 24.776 |
| 29.691 |

Diffraction angles of major peaks (2θ) in X-ray powder diffraction spectrum: 7.3°±0.2°, 17.0°±0.2°, 18.5°±0.2°, 22.6°±0.2°, 24.0°±0.2°.

REFERENCE EXAMPLE 12

Synthesis of Compound (II')

[Chemical Formula 28]

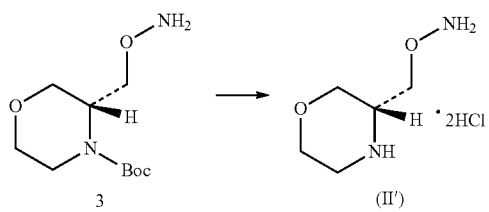

Ethyl acetate (8 mL) was added to Compound 3 (4.12 g, 17.7 mmol), and the mixture was stirred. When 4 mol/L a solution (16 mL) of hydrochloric acid in ethyl acetate was added, white solids were precipitated. Ethyl acetate (8 mL) was added, and then the mixture was stirred for about 4 hours at room temperature. Highly hygroscopic Compound (II') were collected by filtration.

$^1$H-NMR (DMSO-d6) δ: 9.60-11.50 (4H, bs), 4.20-4.31 (2H, m), 3.86-3.93 (2H, m), 3.21-3.77 (4H, m), 3.01-3.10 (1H, m).

The obtained compound absorbed moisture and deliquesced, and therefore it was not possible to perform measurements such as X-ray powder diffraction.

REFERENCE EXAMPLE 13

Synthesis of Compound (II″)

[Chemical Formula 29]

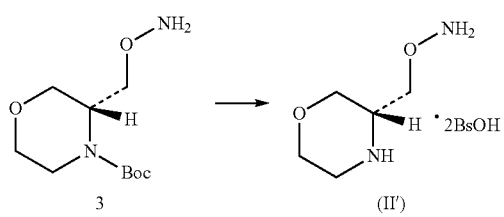

Benzenesulfonic acid (78.57 mg) and tetrahydrofuran (0.2 mL) were stirred at 50° C., and a tetrahydrofuran (0.2 mL) solution of Compound 3 (51.54 mg, 0.222 mmol) was added dropwise. After about 20 minutes, cooling the mixture to room temperature caused solids to precipitate. Then, 0.15 mL of tetrahydrofuran was added, and the mixture was stirred at 50° C. for 10 minutes and cooled to 10° C. Solids were collected by filtration in a nitrogen atmosphere, and thus 57.3 mg of highly hygroscopic Compound (II″) was obtained.

$^1$H-NMR (CD$_3$OD) δ: 7.84-7.87 (4H, m), 7.45-7.47 (6H, m), 4.34-4.36 (2H, m), 3.98-4.08 (2H, m), 3.71-3.80 (3H, m), 3.28-3.41 (2H, m).

The results of X-ray powder diffraction are shown in FIG. 53 and Table 26. (Measurement condition: Method B)

TABLE 26

| 2θ |
| --- |
| 5.600 |
| 8.020 |
| 16.260 |
| 18.000 |
| 19.020 |
| 22.220 |
| 23.160 |
| 24.400 |
| 24.500 |
| 25.520 |

Diffraction angles of major peaks (2θ) in X-ray powder diffraction spectrum: 5.6°±0.2°, 8.0°±0.2°, 18.0°±0.2°, 19.0°±0.2°, 24.5°±0.2°.

EXAMPLE 23

(Results of XRPD Measurement)

The crystals of Compound (II′) described in Reference Example 12 have deliquescing properties and have low crystallinity. Also, as shown in FIG. 53, the crystals of Compound (II″) described in Reference Example 13 show low intensity peaks and have low crystallinity. As described in Example 15 above, it is difficult to handle low crystallinity crystals. On the other hand, it was found that the crystals of Compound (IIA) and the dihydrate crystals of Compound (IIA) described in Examples 21 and 22 are crystals having good crystallinity as shown in FIGS. 10 and 11, and are in crystal forms that can be selected as an intermediate of an active pharmaceutical ingredient.

EXAMPLE 24

(Results of Stability Test)

The crystals of Compound (IIA) obtained in Example 21 were heated at 50° C. for 8 hours and measured NMR data. As a result, compared with the peaks before heating, no changes to the peaks were observed, and it was thus found that the crystals of Compound (IIA) are highly stable crystals.

EXAMPLE 25

Synthesis of Monohydrochloride Crystal Form VI of Compound (I)

[Chemical Formula 30]

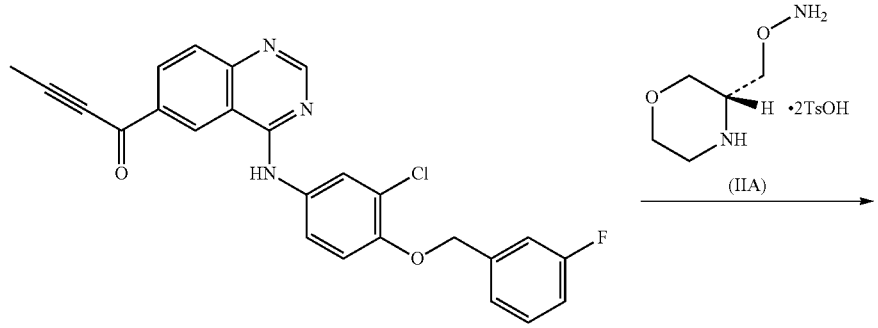

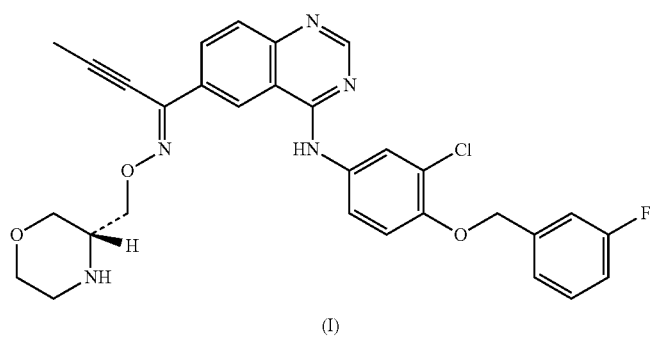

Compound 4 (97.01 g, 217.6 mmol) dissolved in N-methylpyrrolidone (223 mL) and tetrahydrofuran (116 mL) was mixed with Compound (IIA) (119.25 g, 250.2 mmol), p-toluenesulfonic acid monohydrate (49.67 g, 261.1 mmol), tetrahydrofuran (194 mL), and water (17 mL), and the mixture was stirred at 57° C. for 5 hours. After the mixture was cooled to room temperature, the pH was adjusted to 9.0 with an aqueous sodium hydroxide solution, followed by extraction with ethyl acetate (776 mL). The extract was concentrated to 357 mL, ethyl acetate (582 mL) was added, and thus 882.12 g of a dilution was obtained.

2-Propanol (10 mL) was added to 44.11 g of the dilution, and the mixture was heated to 60° C. After the pH was adjusted to 4.3 with 35% hydrochloric acid, the mixture was stirred at 25° C. for 4 hours and filtered, and thus monohydrochloride crystal Form VI (5.6 g, 86.8%) of Compound (I) was obtained.

The following Formulation Examples are mere examples and do not intend to limit the scope of the invention in any way.

FORMULATION EXAMPLE 1

Tablet

An acid addition salt or crystals of the acid addition salt of the compound represented by Formula (I) of the present invention, lactose, and calcium stearate are mixed. The mixture is crushed, granulated, and dried to form granules having a suitable size. Next, calcium stearate is added, and the mixture is compression-molded to form tablets.

FORMULATION EXAMPLE 2

Capsule

An acid addition salt or crystals of the acid addition salt of the compound represented by Formula (I) of the present invention, lactose, and calcium stearate are uniformly mixed to make a powdered drug in a powdery or fine granule form. Capsule shells are filled therewith to form capsules.

FORMULATION EXAMPLE 3

Granule

An acid addition salt or crystals of the acid addition salt of the compound represented by Formula (I) of the present invention, lactose, and calcium stearate are uniformly mixed. After being compression-molded, the mixture is pulverized, classified, and sieved to form granules having a suitable size.

FORMULATION EXAMPLE 4

Orally Disintegrating Tablet

An acid addition salt or crystals of the acid addition salt of the compound represented by Formula (I) of the present invention and crystalline cellulose are mixed, granulated, and then tableted to form orally disintegrating tablets.

FORMULATION EXAMPLE 5

Dry Syrup

An acid addition salt or crystals of the acid addition salt of the compound represented by Formula (I) of the present invention and lactose are mixed, pulverized, classified, and sieved to form a dry syrup having a suitable size.

FORMULATION EXAMPLE 6

Inhalant

An acid addition salt or crystals of the acid addition salt of the compound represented by Formula (I) of the present invention and lactose are mixed and finely pulverized to thereby form an inhalant.

INDUSTRIAL APPLICABILITY

Hydrochloride or crystals of the hydrochloride as well as mono-p-toluenesulfonate or crystals of the mono-p-toluenesulfonate of the compound represented by Formula (I), which are the present invention, are useful as active pharmaceutical ingredients. Also, a pharmaceutical composition containing hydrochloride or crystals of the hydrochloride or mono-p-toluenesulfonate or crystals of the mono-p-toluenesulfonate of the compound represented by Formula (I) is extremely useful as a therapeutic agent or a prophylactic agent for cancer.

In addition, the compound represented by Formula (II), a pharmaceutically acceptable salt thereof, or their solvates are useful intermediates when producing hydrochloride or crystals of the hydrochloride of the compound represented by Formula (I).

The invention claimed is:

1. A crystal of hydrochloride of a compound represented by Formula (I):

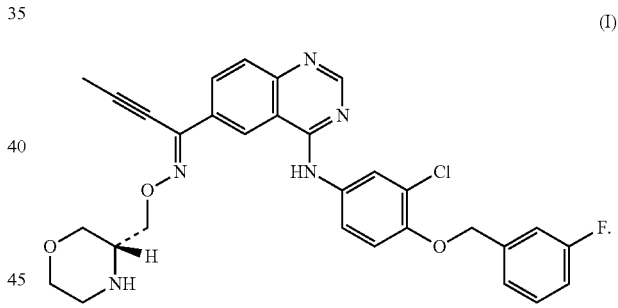

2. The crystal according to claim 1, wherein the hydrochloride is monohydrochloride.

3. The crystal according to claim 2, which exhibits X-ray powder diffraction spectrum having peaks at diffraction angles 2θ: 8.0°±0.2°, 14.1°±0.2°, 20.6°±0.2°, 21.0°±0.2°, and 25.8°±0.2°.

4. The crystal according to claim 2, which exhibits X-ray powder diffraction spectrum having peaks at diffraction angles 2θ: 6.8°±0.2°, 8.0°±0.2°, 14.1°±0.2°, 17.9°±0.2°, 18.5°±0.2°, 20.6°±0.2°, 21.0°±0.2°, 22.5°±0.2°, 25.8°±0.2°, and 28.4°±0.2°.

5. The crystal according to claim 2, which exhibits X-ray powder diffraction spectrum having peaks at diffraction angles 2θ: 23.9°±0.2°, 25.9°±0.2°, 26.2°±0.2°, 26.7°±0.2°, and 28.4°±0.2°.

6. The crystal according to claim 2, which exhibits X-ray powder diffraction spectrum having peaks at diffraction angles 2θ: 7.9°±0.2°, 9.7°±0.2°, 11.9°±0.2°, 15.8°±0.2°, 18.5°±0.2°, 23.9°±0.2°, 25.9°±0.2°, 26.2°±0.2°, 26.7°±0.2°, and 28.4°±0.2°.

7. The crystal according to claim 2, which exhibits X-ray powder diffraction spectrum having peaks at diffraction angles 2θ: 5.4°±0.2°, 16.3°±0.2°, 21.6°±0.2°, 23.2°±0.2°, and 23.7°±0.2°.

8. The crystal according to claim 2, which exhibits X-ray powder diffraction spectrum having peaks at diffraction angles 2θ: 5.4°±0.2°, 8.9°±0.2°, 11.7°±0.2°, 13.8°±0.2°, 16.3°±0.2°, 20.9°±0.2°, 21.6°±0.2°, 23.2°±0.2°, 23.7°±0.2°, and 26.6°±0.2°.

9. A pharmaceutical composition comprising the crystal according to claim 1 and a pharmaceutically acceptable carrier.

10. A crystal of p-toluenesulfonate of a compound represented by Formula (I):

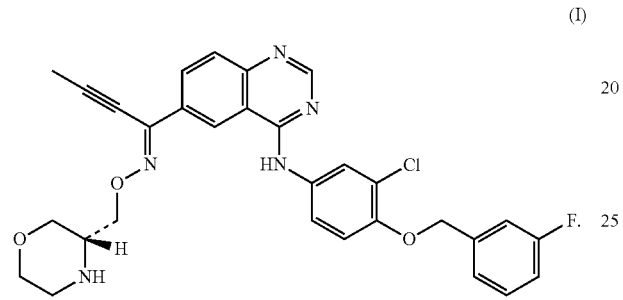

11. The crystal according to claim 10, wherein the p-toluenesulfonate is mono-p-toluenesulfonate.

12. The crystal according to claim 11, which exhibits X-ray powder diffraction spectrum having peaks at diffraction angles 2θ: 13.7°±0.2°, 15.7°±0.2°, 20.0°±0.2°, 22.7°±0.2°, and 25.3°±0.2°.

13. The crystal according to claim 11, which exhibits X-ray powder diffraction spectrum having peaks at diffraction angles 2θ: 6.1°±0.2°, 6.4°±0.2°, 10.8°±0.2°, 13.7°±0.2°, 15.7°±0.2°, 16.3°±0.2°, 20.0°±0.2°, 22.7°±0.2°, 24.6°±0.2°, and 25.3°±0.2°.

14. A pharmaceutical composition comprising the crystal according to claim 10 and a pharmaceutically acceptable carrier.

15. A compound represented by Formula (II):

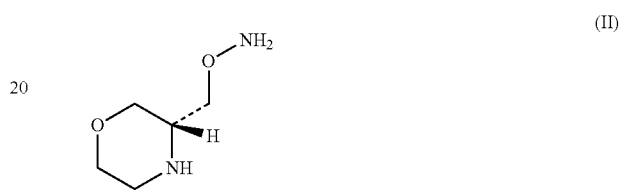

or a pharmaceutically acceptable salt, or solvate thereof.

16. The salt or solvate according to claim 15, wherein the salt is di-p-toluenesulfonate.

* * * * *